(12) United States Patent
Skowerski et al.

(10) Patent No.: US 9,371,345 B2
(45) Date of Patent: Jun. 21, 2016

(54) METATHESIS CATALYSTS CONTAINING ONIUM GROUPS

(71) Applicant: Apeiron Synthesis S.A., Wroclaw (PL)

(72) Inventors: Krzysztof Skowerski, Wroclaw (PL); Lukasz Gulajski, Wroclaw (PL); Michal Bieniek, Wroclaw (PL); Stefan Czarnocki, Wroclaw (PL); Grzegorz Szczpaniak, Wroclaw (PL); Celina Wierzbicka, Wroclaw (PL)

(73) Assignee: Apeiron Synthesis S.A., Wroclaw (PL)

( * ) Notice: Subject to any disclaimer, the term of this patent is extended or adjusted under 35 U.S.C. 154(b) by 0 days.

(21) Appl. No.: 14/730,623

(22) Filed: Jun. 4, 2015

(65) Prior Publication Data

US 2015/0274763 A1    Oct. 1, 2015

Related U.S. Application Data

(62) Division of application No. 13/779,602, filed on Feb. 27, 2013.

(60) Provisional application No. 61/603,790, filed on Feb. 27, 2012.

(51) Int. Cl.

| C07F 15/00 | (2006.01) |
|---|---|
| B01J 31/22 | (2006.01) |
| C07C 209/68 | (2006.01) |
| C07D 307/28 | (2006.01) |
| C07C 29/32 | (2006.01) |
| C07C 29/56 | (2006.01) |
| C07C 67/333 | (2006.01) |
| C08G 61/08 | (2006.01) |

(52) U.S. Cl.
CPC ......... *C07F 15/0046* (2013.01); *B01J 31/2204* (2013.01); *B01J 31/2273* (2013.01); *B01J 31/2278* (2013.01); *B01J 31/2295* (2013.01); *C07C 29/32* (2013.01); *C07C 29/56* (2013.01); *C07C 67/333* (2013.01); *C07C 209/68* (2013.01); *C07D 307/28* (2013.01); *C08G 61/08* (2013.01); *B01J 2231/543* (2013.01); *B01J 2531/821* (2013.01); *B01J 2531/825* (2013.01); *B01J 2531/96* (2013.01); *B01J 2540/42* (2013.01); *B01J 2540/64* (2013.01); *C07B 2200/09* (2013.01); *C07C 2101/10* (2013.01); *C08G 2261/3324* (2013.01); *C08G 2261/418* (2013.01)

(58) Field of Classification Search
CPC .................................................. C07F 15/0046
See application file for complete search history.

(56) References Cited

U.S. PATENT DOCUMENTS

| 6,867,303 B2 | 3/2005 | Grela |
| 8,288,558 B2 | 10/2012 | Arlt et al. |
| 2010/0087644 A1 | 4/2010 | Mauduit et al. |

FOREIGN PATENT DOCUMENTS

| CN | 101684075 | 3/2010 |
| WO | WO2008/065187 | 6/2008 |
| WO | WO2011079439 | 12/2009 |
| WO | WO2011079799 | 7/2011 |
| WO | WO2013/127880 | 9/2013 |

OTHER PUBLICATIONS

Balof et al. "Olefin metathesis catalysts bearing a pH-responsive NHC ligand: a feasible approach to catalyst separation from RCM products" Dalton Transactions, 2008, pp. 5791-5799.*
Jordan et al. "Small-Molecule N-Heterocyclic-Carbene-Containing Olefin-Metathesis Catalysts for Use in Water" Angewante Chemie International Edition, 2007, vol. 46, pp. 5152-5155.*
Ahn et al., A convenient method for the efficient removal of ruthenium byproducts generated during olefin metathesis reactions. Organic Letters, 3(9): 1411-1413 (2001 ).
Balskus et al., Intercalation of multiple carbon atoms between the carbonyls of alphadiketones. J. Org. Chem., 66, pp. 6695-6704 (2001 ).

(Continued)

*Primary Examiner* — Joseph Kosack
(74) *Attorney, Agent, or Firm* — K&L Gates LLP; Brent A. Johnson; Louis C. Cullman

(57) ABSTRACT

Disclosed herein is a general method for the preparation of complexes containing a quaternary onium group in an inert ligand. Some of these complexes may be represented by formula 1:

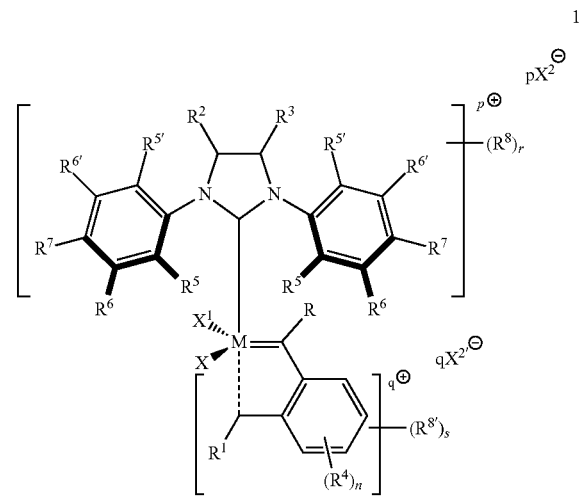

Methods for the preparation of complexes of formula 1, the preparation of intermediates and the use of complexes of formula 1 in metathesis reactions and a method for conducting an olefin metathesis reaction are also described.

8 Claims, No Drawings

(56) References Cited

OTHER PUBLICATIONS

Burtscher et al., Aqueous olefin metathesis. Angew. Chem. Int., 48, pp. 442-454 (2009).

Chen et al., Novel imidazolium ion-tagged Ru-carbene complexes:synthesis and applications for olefin metathesis in ionic liquid. Tetrahedron, vol. 65, pp. 3397-3403 (2009).

Clavier et al., Ionic liquid anchored "boomerang" catalysts bearing saturated and unsaturated NHCs. recyclability in biphasic media for cross-metathesis. Organometallics, vol. 27, pp. 2287-2292 (2007).

Clavier et al., Ring-closing metathesis in biphasic BMI-PF6 ionic liquid/toulene medium: a powerful recyclable and environmentally friendly process. Chem. Commun., pp. 2282-2283 (2004).

Clavier et al., Sustainable concepts in olefin metathesis. Angew. Chem. Int., 46, pp. 6786-6801 (2007).

Conrad et al., Highly efficient Ru-pseudohalide catalysts for olefin metathesis. J. Am. Chem. Soc., 127, pp. 11882-11883 (2005).

Consorti et al., On the imobilization of ruthenium metathesis catalysts in imidazolium ionic liquids. Organometallics, vol. 28, pp. 4527-4533 (2009).

Grela et al., A good bargain: an inexpensive, air-stable ruthenium metathesis catalyst derived from alpha-asarone. Eur. J. Org. Chem., pp. 963-966 (2003).

Gulajski et al., A Highly Active Aqueous Olefin Metathesis Catalyst Bearing a Quaternary Ammonium Group, ChemSusChem 2008, 1:103-109.

Kirschning et al., Highly active ammonium-tagged olefin-metathesis catalyst for simplified purification. Synlett, No. 17, pp. 2692-2696 (2008).

Michrowska et al, A green catalyst for green chemistry: Synthesis and application of an olefin metathesis catalyst bearing a quaternary ammonium group. Green Chem., 2006, 8:685-688.

Michrowska et al., A simple and practical phase-separation approach to the recycling of a homogeneous metathesis catalyst. Chem. Commun., pp. 841-843 (2006).

Paquetie et al., A convenient method for removing all highly-colored byproducts generated during olefin metathesis reactions. Organic Letters, vol. 2, No. 9, pp. 1259-1261 (2000).

Partial International Search Report for PCT/EP2013/053697 filed on Feb. 27, 2013.

Rix et al., Activated pyridinium-tagged ruthenium complexes as efficient catalysts for ringclosing metathesis. Journal of Organometallic Chemistry 691: 5397-5405 (2006).

Rix et al., Highly recoverable pyridinium-tagged Hoveyda-Grubbs pre-catalyst for olefin metathesis. Design of the boomrang ligand toward the optimal compromise between activity and reusability. Chem. Commun., pp. 3771-3773, (2007).

Yao et al., An ionic liquid-tagged second generation Hoveyda-Grubbs ruthenium carbene complex as highly reactive and recyclable catalyst for ring-closing metathesis of di-, triand tetrasubstituted dienes. Journal of Organometallic Chemistry, vol. 690, No. 15, pp. 3577-3584 (2005).

\* cited by examiner

METATHESIS CATALYSTS CONTAINING ONIUM GROUPS

CROSS-REFERENCE TO RELATED APPLICATIONS

This application is a divisional of U.S. application Ser. No. 13/779,602, filed Feb. 27, 2013, which claims priority to U.S. Provisional Patent Application No. 61/603,790, filed Feb. 27, 2012 and Polish Patent Application No. P.398247, filed Feb. 27, 2012, all of which are incorporated by reference herein in their entireties.

SUMMARY

This disclosure relates to a general method for the preparation of complexes containing a quaternary onium group in an inert ligand which complexes are widely used as pre(catalysts) in metathesis reactions. This disclosure also relates to new metal complexes, and their method of preparation and use in metathesis reactions. The disclosure also relates to intermediates used in the preparation of these complexes, and methods of conducting metathesis reactions.

In recent years, tremendous progress has been made in the field of olefin metathesis. The development of new, more stable and active olefin metathesis catalysts (such as A and B) led to a significant increase in the area of possible applications of this transformation.

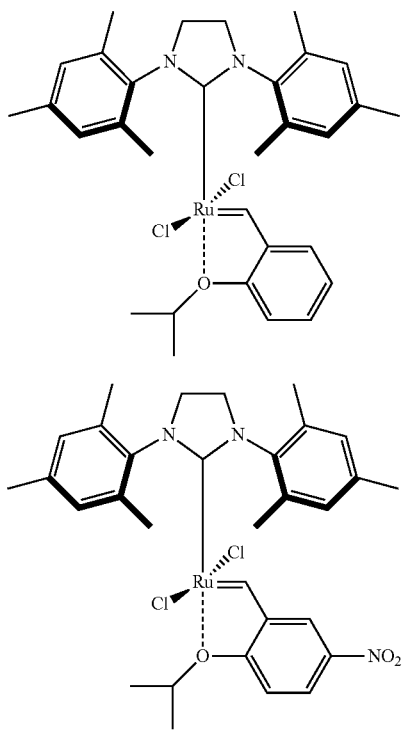

A significant problem with using metathesis catalysts in the industry (mainly pharmaceutical) is removal of contamination containing heavy metal from the product. The development of practical, efficient and economically advantageous methods of metal removal can support further implementation of metathesis technology.

There are several classic methods of removing by-products containing heavy metal. Various "scavengers" were used for this purpose, or catalysts were designed with an increased affinity to silica. None of the existing methods appear to be universal either due to too little or too much scavenger activity (resulting in a prolonged purification stage or side reactions), or insufficient affinity of catalysts for an adsorbent.

In order to develop a simple method of removing metals from the postreaction mixture, catalysts containing polar ammonium groups were synthesized. Although a simple filtration of the postreaction mixture through silica gel can reduce the heavy metal content in the product, the method is not adequate to meet the requirements of the pharmaceutical industry. Additionally, there has been little research activity related to (pre)catalysts having onium groups in an inert ligand, likely because of the difficulty in the synthesis of such complexes. Furthermore, catalysts which contain an onium group in a N-heterocyclic carbene ligand (NHC) are known, which may be as a result of unique difficulties occurring during the synthesis by means of classical methods.

Another significant problem is the lack of effective and active catalysts for a metathesis reaction carried out in water. Such a transformation may be of great importance in the synthesis of compounds of biological activity.

It was surprisingly discovered that complexes containing an quaternary onium group in an inert ligand can be prepared in a simple and efficient manner. Therefore, some embodiments include a method of preparation of complexes containing an quaternary onium group in an inert ligand in the course of a reaction of a relevant complex with an alkylating reagent. Some embodiments include, in addition to new metal complexes acting as pre(catalysts) of a metathesis reaction, a method of their preparation and their use in a metathesis reaction.

The complexes described herein (referred to herein as "the complexes") have an analogous effectiveness and/or activity in metathesis reactions to certain catalysts known in the prior art. The complexes allow products with a very low content of metal to be obtained following the application of simple and cheap methods for treatment of the postreaction mixture. Furthermore, the complexes are characterized by good solubility and high stability in pure water, and exhibit high activity and/or effectiveness in metathesis reactions carried out in water.

Some embodiments include a method of synthesis of complexes of formula 15. In such a method, a complex of formula 10 is subjected to a reaction with an alkylating reagent of formula $R^8X^2$.

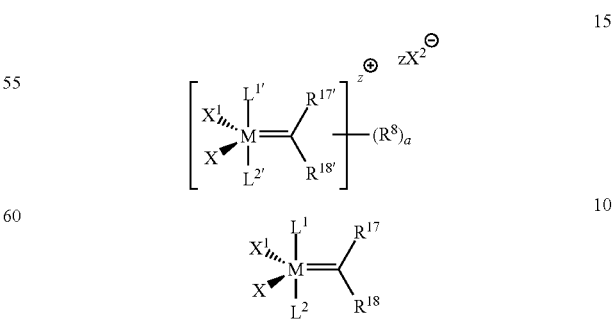

With respect to formula 15, $L^{1'}$ is an inert ligand.
With respect to formula 15, $L^{2'}$ is an inert ligand.

With respect to formula 15, at least one of $L^{1'}$ and $L^{2'}$ is substituted with at least one quaternary ammonium, including a $C_{4-20}N_{1-2}$ quaternary ammonium, a $C_{4-10}N$ quaternary ammonium, a $C_{4-20}N_2$ quaternary ammonium, or a $C_{4-20}NO$ quaternary ammonium, and/or a phosphonium group, such as a $C_{4-20}P_{1-2}$ phosphonium, a $C_{4-10}P$ phosphonium, or a $C_{4-20}P_2$ phosphonium. In some embodiments, at least one of $L^{1'}$ and $L^{2'}$ is substituted with a $-(CH_2)_{0-4}N^+(C_{1-3}H_{3-7})_3$ group, a

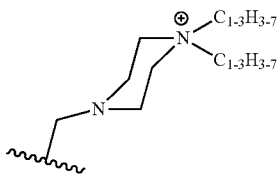

group, a

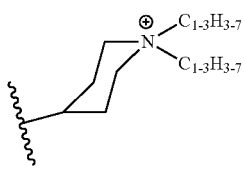

group, or a

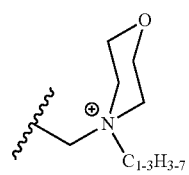

group.

In some embodiments, at least one of $L^{1'}$ and $L^{2'}$ is substituted with a $-CH_2N^+(CH_3)_3$ group.

In some embodiments, at least one of $L^{1'}$ and $L^{2'}$ is substituted with

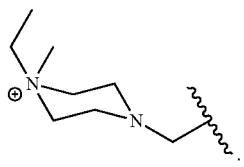 [SMILES: *CN1CC[N+](C)(CC)CC1]

In some embodiments, at least one of $L^{1'}$ and $L^{2'}$ is substituted with

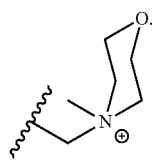

In some embodiments, at least one of $L^{1'}$ and $L^{2'}$ is substituted with

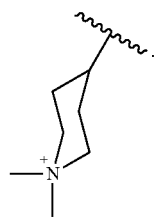

With respect to formula 10 or 15, M is ruthenium or osmium.

With respect to formula 10 or 15, X is an anionic ligand. In some embodiments, X is $F^-$, $Cl^-$, $Br^-$, or $I^-$. In some embodiments, X is $Cl^-$.

With respect to formula 10 or 15, $X^1$ is an anionic ligand. In some embodiments, $X^1$ is $F^-$, $Cl^-$, $Br^-$, or $I^-$. In some embodiments, $X^1$ is $Cl^-$.

With respect to formula 10 or 15, or the alkylating reagent of formula $R^8X^2$, $X^2$ is an anionic ligand. In some embodiments, $X^2$ is $F^-$, $Cl^-$, $Br^-$, or $I^-$. In some embodiments, $X^2$ is $Cl^-$.

With respect to formula 15, $R^8$ is $-C_{1-20}$ alkyl (including $C_{1-3}$ alkyl, $C_{1-6}$ alkyl, $C_{1-12}$ alkyl, etc.), $-C_{3-8}$ cycloalkyl, $-C_{2-20}$ alkenyl, $-C_{2-20}$ alkynyl group. Each of these groups may be optionally substituted with a group such as a halogen atom, $-C_{5-10}$ aryl (such as phenyl or naphthyl), $-C(=O)-C_{1-6}$ alkyl (such as acetyl, propionyl, butyryl, etc.), $-C(=O)-O-C_{1-6}$ alkyl, $-C(=O)-N(C_{1-6}$ alkyl$)_2$, $-C(=O)-N-(C_{1-6}$ alkyl$)-O-C_{1-6}$ alkyl, $-C(=O)-C_{5-10}$ aryl, $-C(=O)-O-C_{5-10}$ aryl, $-C(=O)-N(C_{5-10}$ aryl$)_2$, $-C(=O)-N-(C_{5-10}$ aryl$)-O-C_{5-10}$ aryl group, etc. Examples of $C_{1-6}$ alkyl for any of the groups above include methyl, ethyl, propyl, isopropyl, n-butyl, isobutyl, t-butyl, pentyl groups, hexyl groups, etc.

With respect to formula 15, $R^{17'}$ is H, $-C_{1-20}$ alkyl, $-C_{2-20}$ alkenyl, $-C_{2-20}$ alkynyl or $-C_{5-10}$ aryl group. Each of these groups (except H) may be optionally substituted. In some embodiments, at least one of the substituents is a quaternary ammonium, including a $C_{4-20}N_{1-2}$ quaternary ammonium, a $C_{4-10}N$ quaternary ammonium, a $C_{4-20}N_2$ quaternary ammonium, or a $C_{4-20}NO$ quaternary ammonium, and/or a phosphonium group, such as a $C_{4-20}P_{1-2}$ phosphonium, a $C_{4-10}P$ phosphonium, or a $C_{4-20}P_2$ phosphonium. In some embodiments, the quaternary ammonium is a $-(CH_2)_{0-4}N^+(C_{1-3}H_{3-7})_3$ group, a

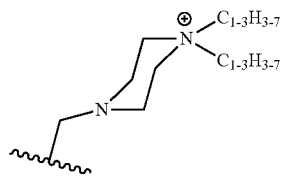

group, a

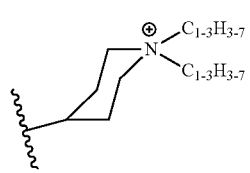

group, or a

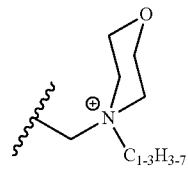

group.

In some embodiments, $R^{17'}$ has a —$CH_2N^+(CH_3)_3$ substituent, meaning that —$C_{1-20}$ alkyl, —$C_{2-20}$ alkenyl, —$C_{2-20}$ alkynyl or —$C_{5-10}$ aryl group has a —$CH_2N^+(CH_3)_3$ substituent.

In some embodiments, $R^{17'}$ has a

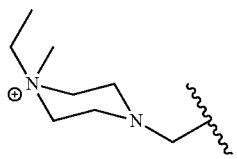 [SMILES: *CN1CC[N+](C)(CC)CC1]

substituent.

In some embodiments, $R^{17'}$ has a

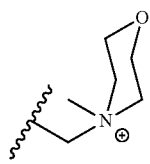 [SMILES: *C[N+]1(C)CCOCC1]

substituent.

In some embodiments, $R^{17'}$ has a

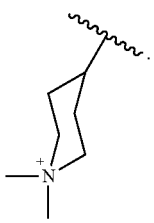

substituent.

With respect to formula 15, $R^{18'}$ is a phenyl or vinyl substituent, or —$C=C(CH_3)_2$. Each of these groups may be optionally substituted. In some embodiments, at least one of the substituents is a quaternary ammonium, including a $C_{4-20}N_{1-2}$ quaternary ammonium, a $C_{4-10}N$ quaternary ammonium, a $C_{4-20}N_2$ quaternary ammonium, or a $C_{4-20}NO$ quaternary ammonium, and/or a phosphonium group, such as a $C_{4-20}P_{1-2}$ phosphonium, a $C_{4-10}P$ phosphonium, or a $C_{4-20}P_2$ phosphonium. In some embodiments, the quaternary ammonium is a —$(CH_2)_{0-4}N^+(C_{1-3}H_{3-7})_3$ group, a

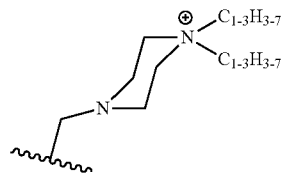

group, a

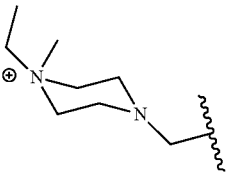 [SMILES: *CN1CC[N+](C)(CC)CC1]

group, or a

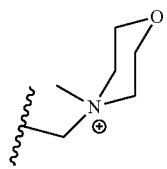

group.

In some embodiments, $R^{18'}$ has a —$CH_2N^+(CH_3)_3$ substituent, meaning that a phenyl, vinyl, or —$C=C(CH_3)_2$ has a —$CH_2N^+(CH_3)_3$ substituent.

In some embodiments, $R^{18'}$ has a

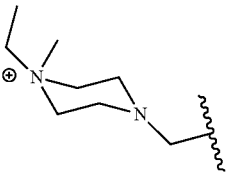 [SMILES: *CN1CC[N+](C)(CC)CC1]

substituent.

In some embodiments, $R^{18'}$ has a

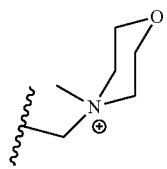

substituent.

In some embodiments, $R^{18'}$ has a

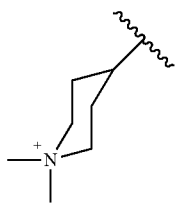

substituent.

With respect to formula 15, $R^{17'}$ and $R^{18'}$ may be optionally linked together to form a cyclic or polycyclic system that is aliphatic or aromatic.

With respect to formula 15, $R^{17'}$ and $R^{18'}$, together with a carbon atom connecting them, can optionally be a 3-phenyl-1H-indene-1-ylide substituent.

With respect to formula 15, $R^{17'}$ and/or $R^{18'}$ may be optionally linked to $L^1$ or $L^2$ to form a bidentate ligand.

With respect to formula 15, a is 1, 2, 3, 4, 5, 6 or 7.

With respect to formula 15, z is 1, 2, 3, 4, 5, 6 or 7.

With respect to formula 10, $L^1$ is an inert ligand.

With respect to formula 10, $L^2$ is an inert ligand.

With respect to formula 10, at least one of $L^1$ and $L^2$ contains independently at least one $X^2$ substituent or is independently substituted with aliphatic and/or aromatic and/or heterocyclic alkylamino or alkylphosphine. In some embodiments, the alkylamino may include a $C_{3-20}N_{1-2}$ amino, a $C_{3-10}N$ amino, a $C_{3-20}N_2$ amino, or a $C_{3-20}NO$ amino. In some embodiments, the alkylphosphine may include a $C_{3-20}P_{1-2}$ phosphine, a $C_{4-10}P$ phosphine, or a $C_{4-20}P_2$ phosphine. In some embodiments, at least one of $L^1$ and $L^2$ is substituted with a $-(CH_2)_{0-4}N(C_{1-3}H_{3-7})_2$ group, a

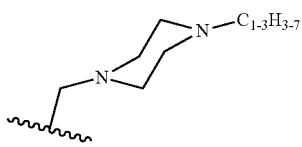

group, a

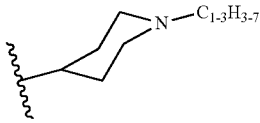

group, or a

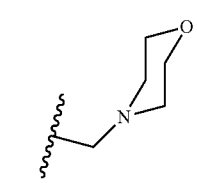 [SMILES: *CN1CCOCC1]

group.

In some embodiments, at least one of $L^1$ and $L^2$ is substituted with a $CH_2N(CH_3)_2$ group.

In some embodiments, at least one of $L^1$ and $L^2$ is substituted with

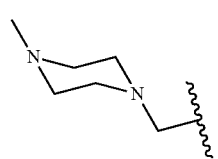

In some embodiments, at least one of $L^1$ and $L^2$ is substituted with

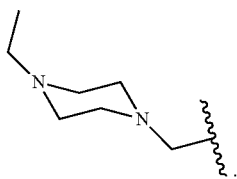 [SMILES: *CN1CCN(CC)CC1]

In some embodiments, at least one of $L^1$ and $L^2$ is substituted with

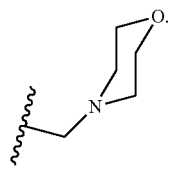 [SMILES: *CN1CCOCC1]

In some embodiments, at least one of $L^1$ and $L^2$ is substituted with

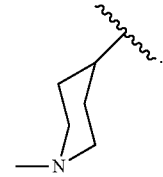 [SMILES: *C1CCN(C)CC1]

With respect to formula 10, $R^{17}$ is H, $-C_{1-20}$ alkyl, $-C_{2-20}$ alkenyl, $-C_{2-20}$ alkynyl or a $-C_{5-10}$ aryl group. Each of these groups, except H, is optionally substituted. In some embodiments, at least one substituent is $X^2$ or an aliphatic and/or aromatic and/or heterocyclic alkylamino or alkylphosphine. In some embodiments, the alkylamino may include a $C_{3-20}N_{1-2}$ amino, a $C_{3-10}N$ amino, a $C_{3-20}N_2$ amino, or a $C_{3-20}NO$ amino. In some embodiments, the alkylphosphine may include a $C_{3-20}P_{1-2}$ phosphine, a $C_{4-10}P$ phosphine, or a $C_{4-20}P_2$ phosphine.

In some embodiments, $R^{17}$ has a $-(CH_2)_{0-4}N(C_{1-3}H_{3-7})_2$ substituent, a

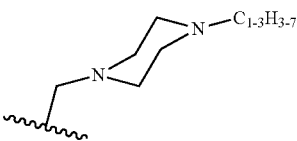

substituent, a

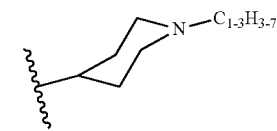

substituent, or a

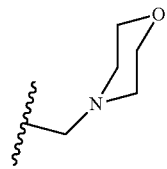

substituent, meaning that —$C_{1-20}$ alkyl, —$C_{2-20}$ alkenyl, —$C_{2-20}$ alkynyl or —$C_{5-10}$ aryl has one of these substituents.

In some embodiments, $R^{17}$ has a —$CH_2N(CH_3)_2$ substituent.

In some embodiments, $R^{17}$ has a

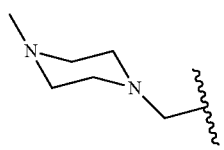 [SMILES: *CN1CCN(C)CC1]

substituent.

In some embodiments, $R^{17}$ has a

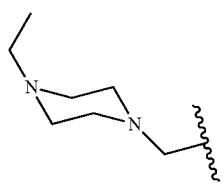 [SMILES: *CN1CCN(CC)CC1]

substituent.

In some embodiments, $R^{17}$ has a

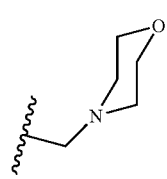

substituent.

In some embodiments, $R^{17}$ has a

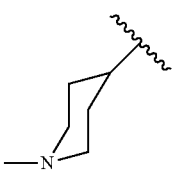 [SMILES: *C1CCN(C)CC1]

substituent.

With respect to formula 10, $R^{18}$ is a phenyl, vinyl, or —C=C(CH$_3$)$_2$. Each of these is optionally substituted. In some embodiments, at least one substituent is $X^2$ or an aliphatic and/or aromatic and/or heterocyclic alkylamino or alkylphosphine. In some embodiments, the alkylamino may include a $C_{3-20}N_{1-2}$ amino, a $C_{3-10}N$ amino, a $C_{3-20}N_2$ amino, or a $C_{3-20}NO$ amino. In some embodiments, the alkylphosphine may include a $C_{3-20}P_{1-2}$ phosphine, a $C_{4-10}P$ phosphine, or a $C_{4-20}P_2$ phosphine.

In some embodiments, $R^{18}$ has a —$(CH_2)_{0-4}N(C_{1-3}H_{3-7})_2$ substituent, a

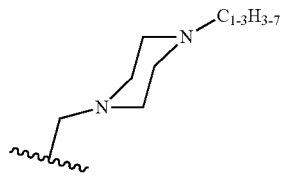

substituent, a

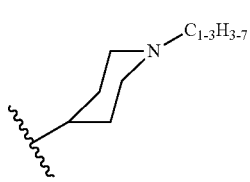

substituent, or a

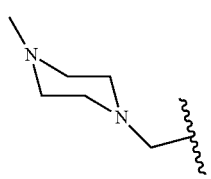 [SMILES: *CN1CCN(C)CC1]

substituent, meaning that —$C_{1-20}$ alkyl, —$C_{2-20}$ alkenyl, —$C_{2-20}$ alkynyl or —$C_{5-10}$ aryl has one of these substituents, In some embodiments, $R^{18}$ has a —$CH_2N(CH_3)_2$ substituent.

In some embodiments, $R^{18}$ has a

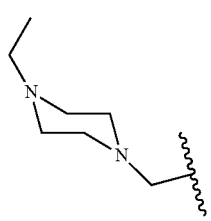 [SMILES: *CN1CCN(CC)CC1]

substituent.

In some embodiments, $R^{18}$ has a substituent.

In some embodiments, $R^{18}$ has a

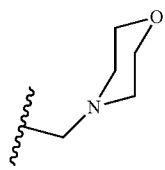

substituent.

In some embodiments, $R^{18}$ has a

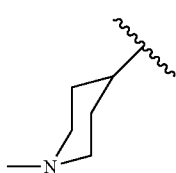

substituent.

With respect to formula 10, $R^{17}$ and $R^{18}$ may also be optionally linked together to form a cyclic or polycyclic system that is aliphatic or aromatic; $R^{17}$ and/or $R^{18}$ may also be optionally linked to $L^1$ or $L^2$ to form a bidentate ligand; and/or $R^{17}$ and $R^{18}$, together with a carbon atom connecting them, can optionally be a 3-phenyl-1H-indene-1-ylide substituent.

With respect to the alkylating reagent of formula $R^8X^2$, R is —$C_{1-20}$ alkyl (such as methyl, ethyl, propyl, isopropyl, n-butyl, isobutyl, t-butyl, pentyl groups, hexyl groups, etc.), —$C_{3-8}$ cycloalkyl, —$C_{2-20}$ alkenyl, —$C_{2-20}$ alkynyl group. Each of these groups are optionally substituted with halogen atoms, —$C_{5-10}$ aryl, —C(=O)—$C_{1-6}$ alkyl, —C(=O)—O—$C_{1-6}$ alkyl, —C(=O)—N($C_{1-6}$alkyl)$_2$, —C(=O)—N—($C_{1-6}$ alkyl)-O—$C_{1-6}$ alkyl, —C(=O)—$C_{5-10}$ aryl, —C(=O)—O—$C_{5-10}$aryl, —C(=O)—N($C_{5-10}$ aryl)$_2$, or —C(=O)—N—($C_{5-10}$ aryl)-O—$C_{5-10}$ aryl.

Some embodiments include a method of synthesis of complexes of formula 17. In this method, a complex of formula 10 is subjected to a reaction with compound $TR^{19}(R^{19'})(R^{19''})$.

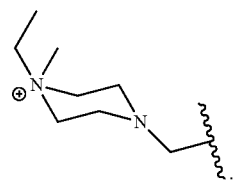 [SMILES: *CN1CC[N+](C)(CC)CC1]

With respect to formula 17, $L^{1'}$ is an inert ligand.
With respect to formula 17, $L^{2'}$ is an inert ligand.
With respect to formula 17, at least one of $L^{1'}$ and $L^{2'}$ is substituted with at least one quaternary ammonium, including a $C_{4-20}N_{1-2}$ quaternary ammonium, a $C_{4-10}N$ quaternary ammonium, a $C_{4-20}N_2$ quaternary ammonium, or a $C_{4-20}NO$ quaternary ammonium, and/or a phosphonium group, such as a $C_{4-20}P_{1-2}$ phosphonium, a $C_{4-10}P$ phosphonium, or a $C_{4-20}P_2$ phosphonium. In some embodiments, at least one of $L^{1'}$ and $L^{2'}$ is substituted with a —$(CH_2)_{0-4}N^+(C_{1-3}H_{3-7})_3$ group, a

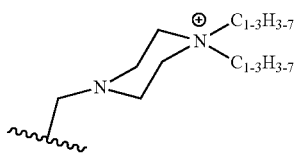

group, a

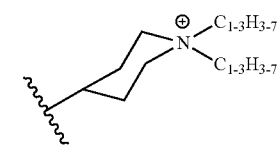

group, or a

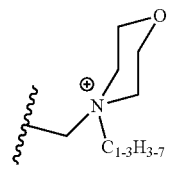

group,

In some embodiments, at least one of $L^{1'}$ and $L^{2'}$ is substituted with a —$CH_2N^+(CH_3)_3$ group.

In some embodiments, at least one of $L^{1'}$ and $L^{2'}$ is substituted with

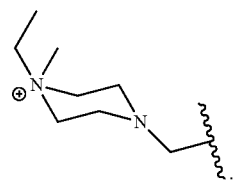 [SMILES: *CN1CC[N+](C)(CC)CC1]

In some embodiments, at least one of $L^{1'}$ and $L^{2'}$ is substituted with

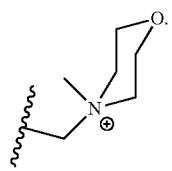 [SMILES: *C[N+]1(C)CCOCC1]

In some embodiments, at least of one of $L^{1'}$ and $L^{2'}$ is substituted with

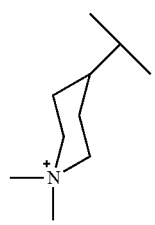

With respect to formula 10 or 17, M is ruthenium or osmium.

With respect to formula 10 or 17, X is an anionic ligand. In some embodiments, X is $F^-$, $Cl^-$, $Br^-$, or $I^-$. In some embodiments, X is $Cl^-$.

With respect to formula 10 or 17, $X^1$ is an anionic ligand. In some embodiments, $X^1$ is $F^-$, $Cl^-$, $Br^-$, or $I^-$. In some embodiments, $X^1$ is $Cl^-$.

With respect to formula 17, $X^2$ is an anionic ligand. In some embodiments, $X^2$ is $F^-$, $Cl^-$, $Br^-$, or $I^-$. In some embodiments, $X^2$ is $Cl^-$.

With respect to formula 17, $R^{17'}$ is H, $-C_{1-20}$ alkyl, $-C_{2-20}$ alkenyl, $-C_{2-20}$ alkynyl or $-C_{5-10}$ aryl group. Each of these groups (except H) may be optionally substituted with a quaternary ammonium, including a $C_{4-20}N_{12}$ quaternary ammonium, a $C_{4-10}N$ quaternary ammonium, a $C_{4-20}N_2$ quaternary ammonium, or a $C_{4-20}NO$ quaternary ammonium, and/or a phosphonium group, such as a $C_{4-20}P_{1-2}$ phosphonium, a $C_{4-10}P$ phosphonium, or a $C_{4-20}P_2$ phosphonium. In some embodiments, the quaternary ammonium is a $-(CH_2)_{0-4}N^+(C_{1-3}H_{3-7})_3$ group, a

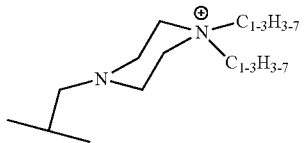

group, a

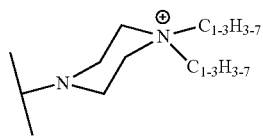

group, or a

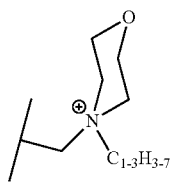

group,

In some embodiments, $R^{17'}$ has a $-CH_2N^+(CH_3)_3$ substituent, meaning that $-C_{1-20}$ alkyl, $-C_{2-20}$ alkenyl, $-C_{2-20}$ alkynyl, $-C_{5-10}$ aryl has a $-CH_2N^+(CH_3)_3$ substituent.

In some embodiments, $R^{17'}$ has a

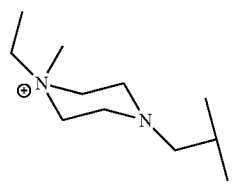

substituent.

In some embodiments, $R^{17'}$ has a

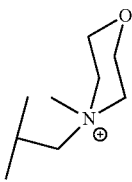

substituent.

In some embodiments, $R^{17'}$ has a

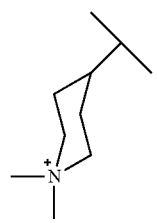

substituent.

With respect to formula 17, $R^{18'}$ is a phenyl or vinyl substituent, or $-C=C(CH_3)_2$. Each of these groups is optionally substituted. In some embodiments, at least one substituent is a quaternary ammonium, including a $C_{4-20}N_{1-2}$ quaternary ammonium, a $C_{4-10}N$ quaternary ammonium, a $C_{4-20}N_2$ quaternary ammonium, or a $C_{4-20}NO$ quaternary ammonium, and/or a phosphonium group, such as a $C_{4-20}P_{1-2}$ phosphonium, a $C_{4-10}P$ phosphonium, or a $C_{4-20}P_2$ phosphonium. In some embodiments, the quaternary ammonium is a $-(CH_2)_{0-4}N^+(C_{1-3}H_{3-7})_3$ group, a

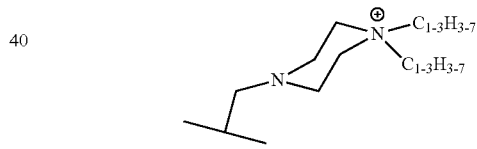

group, a

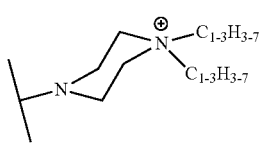

group, or a

group.

In some embodiments, $R^{18'}$ has a —CH$_2$N$^+$(CH$_3$)$_3$ substituent, meaning theta phenyl, vinyl, or —C=C(CH$_3$)$_2$ has a —CH$_2$N$^+$(CH$_3$)$_3$ substituent.

In some embodiments, $R^{18'}$ has a

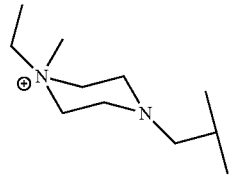

substituent

In some embodiments, $R^{18'}$ has a

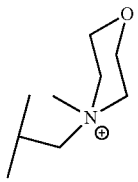

substituent.

In some embodiments, $R^{18'}$ is

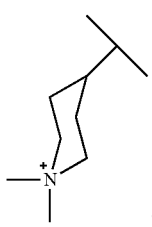

With respect to formula 17, $R^{17'}$ and $R^{18'}$ may be optionally linked together to form a cyclic or polycyclic system that is aliphatic or aromatic.

With respect to formula 17, $R^{17'}$ and $R^{18'}$, together with a carbon atom connecting them, can optionally be a 3-phenyl-1H-indene-1-ylide substituent.

With respect to formula 17, $R^{17'}$ and/or $R^{18'}$ may be optionally linked to $L^1$ or $L^2$ to form a bidentate ligand.

With respect to formula 17, a is 1, 2, 3, 4, 5, 6 or 7.

With respect to formula 17, z is 1, 2, 3, 4, 5, 6 or 7.

With respect to formula 17 or compound TR$^{19}$(R$^{19'}$)(R$^{19''}$), T is N or P.

With respect to formula 17 or compound TR$^{19}$(R$^{19'}$)(R$^{19''}$), $R^{19}$ is H, —C$_{1-6}$ alkyl (such as methyl, ethyl, propyl, isopropyl, n-butyl, isobutyl, t-butyl, pentyl isomers, hexyl isomers, etc), aryl (such as phenyl, naphthyl, etc.), or a C$_{4-10}$ heterocyclic group.

With respect to formula 17 or compound TR$^{19}$(R$^{19'}$)(R$^{19''}$), $R^{19'}$ is H, —C$_{1-6}$ alkyl (such as methyl, ethyl, propyl, isopropyl, n-butyl, isobutyl, t-butyl, pentyl isomers, hexyl isomers, etc.), —C$_{5-10}$ aryl (such as phenyl, naphthyl, etc.), or a C$_{4-10}$ heterocyclic group.

With respect to formula 17 or compound TR$^{19}$(R$^{19'}$)(R$^{19''}$), $R^{19''}$ is H, alkyl (such as methyl, ethyl, propyl, isopropyl, n-butyl, isobutyl, t-butyl, pentyl isomers, hexyl isomers, etc.), —C$_{5-10}$ aryl (such as phenyl, naphthyl, etc.), or a C$_{4-10}$ heterocyclic group.

With respect to formula 10, $L^1$ is an inert ligand.

With respect to formula 10, $L^2$ is an inert ligand.

With respect to formula 10, at least one of $L^1$ and $L^2$ contains independently at least one $X^2$ substituent, or is independently substituted with aliphatic and/or aromatic and/or heterocyclic alkylamino or alkylphosphine. In some embodiments, the alkylamino may include a C$_{3-20}$N$_{1-2}$ amino, a C$_{3-10}$N amino, a C3-20N2 amino, or a C3-20NO amino. In some embodiments, the alkylphosphine may include a C3-20P1-2 phosphine, a C4-10P phosphine, or a C4-20P2 phosphine. In some embodiments, at least one of $L^1$ and $L^2$ is substituted with a —(CH2)0-4N(C1-3H3-7)2 group, a

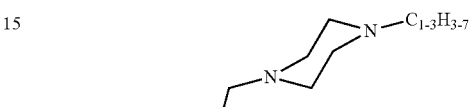

group, a

group, or a

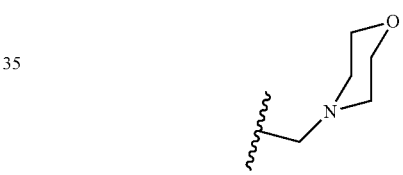

group.

In some embodiments, at least one of L1 and L2 is substituted with a —CH2N(CH3)2 group.

In some embodiments, at least one of $L^1$ and $L^2$ is substituted with

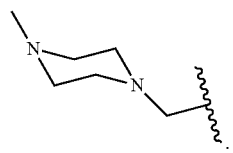 [SMILES: *CN1CCN(C)CC1]

In some embodiments, at least one of $L^1$ and $L^2$ is substituted with

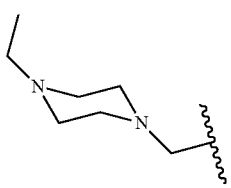

In some embodiments, at least one of $L^1$ and $L^2$ is substituted with

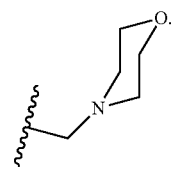 [SMILES: *CN1CCOCC1]

In some embodiments, at least one of $L^1$ and $L^2$ is substituted with

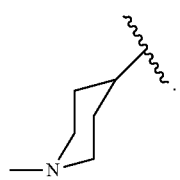 [SMILES: *C1CCN(C)CC1]

With respect to formula 10, $R^{17}$ is H, —$C_{1-20}$ alkyl, —$C_{2-20}$ alkenyl, —$C_{2-20}$ alkynyl or a —$C_{5-10}$ aryl group. Each of these groups, except H, is optionally substituted. In some embodiments, at least one substituent is $X^2$ or an aliphatic and/or aromatic and/or heterocyclic alkylamino or alkylphosphine. In some embodiments, the alkylamino may include a $C_{3-20}N_{1-2}$ amino, a $C_{3-10}N$ amino, a $C_{3-20}N_2$ amino, or a $C_{3-20}NO$ amino. In some embodiments, the alkylphosphine may include a $C_{3-20}P_{1-2}$ phosphine, a $C_{4-10}P$ phosphine, or a $C_{4-20}P_2$ phosphine.

In some embodiments, $R^{17}$ has a —$(CH_2)_{0-4}N(C_{1-3}H_{3-7})_2$ substituent, a

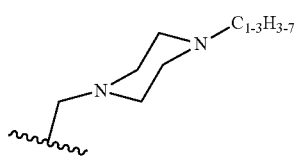

substituent, a

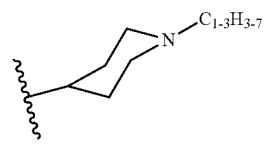

substituent, or a

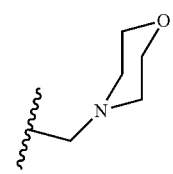

substituent, meaning that —$C_{1-20}$ alkyl, —$C_{2-20}$ alkenyl, —$C_{2-20}$ alkynyl or —$C_{5-10}$ aryl has one of these substituents.

In some embodiments, $R^{17}$ has a —$CH_2N(CH_3)_2$ substituent.

In some embodiments, $R^{17}$ has a

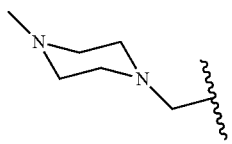 [SMILES: *CN1CCN(C)CC1]

substituent.

In some embodiments, $R^{17}$ has a

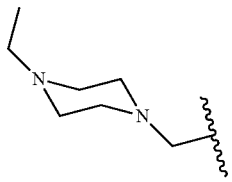 [SMILES: *CN1CCN(CC)CC1]

substituent.

In some embodiments, $R^{17}$ has a

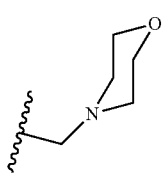 [SMILES: *CN1CCOCC1]

substituent.

In some embodiments, $R^{17}$ has a

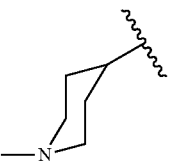 [SMILES: *C1CCN(C)CC1]

substituent.

With respect to formula 10, $R^{18}$ is a phenyl, vinyl, or —C=C(CH$_3$)$_2$. Each of these groups is optionally substituted. In some embodiments, at least one substituent is $X^2$ or an aliphatic and/or aromatic and/or heterocyclic alkylamino or alkylphosphine. In some embodiments, the alkylamino may include a $C_{3-20}N_{1-2}$ amino, a $C_{3-10}N$ amino, a $C_{3-20}N_2$ amino, or a $C_{3-20}NO$ amino. In some embodiments, the alkylphosphine may include a $C_{3-20}P_{1-2}$ phosphine, a $C_{4-10}P$ phosphine, or a $C_{4-20}P_2$ phosphine.

In some embodiments, $R^{18}$ has a —$(CH_2)_{0-4}N(C_{1-3}H_{3-7})_2$ substituent, a

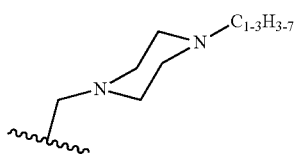

substituent, a

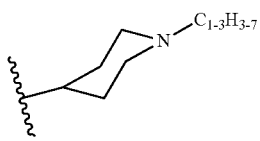

substituent, or a

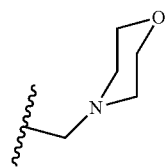 [SMILES: *CN1CCOCC1]

substituent, meaning that —$C_{1-20}$ alkyl, —$C_{2-20}$ alkenyl, —$C_{2-20}$ alkynyl or —$C_{5-10}$ aryl has one of these substituents.

In some embodiments, $R^{18}$ has a —$CH_2N(CH_3)_7$ substituent.

In some embodiments, $R^{18}$ has a

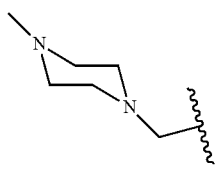 [SMILES: *CN1CCN(C)CC1]

substituent.

In some embodiments, $R^{18}$ has a

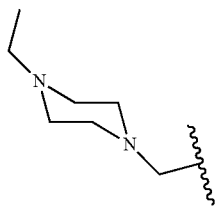 [SMILES: *CN1CCN(CC)CC1]

substituent.

In some embodiments, $R^{18}$ has a

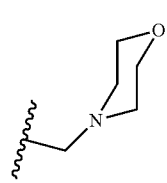 [SMILES: *CN1CCOCC1]

substituent.

In some embodiments, $R^{18}$ has a

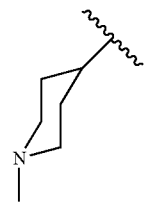

substituent.

With respect to formula 10, $R^{17}$ and $R^{18}$ may also be optionally linked together to form a cyclic or polycyclic system that is aliphatic or aromatic; $R^{17}$ and/or $R^{18}$ may also be optionally linked to $L^1$ or $L^2$ to form a bidentate ligand; and/or $R^{17}$ and $R^{18}$, together with a carbon atom connecting them, can optionally be a 3-phenyl-1H-indene-1-ylide substituent.

In some embodiments. $L^1$ in the complex of general formula 10 is defined by formula 9.

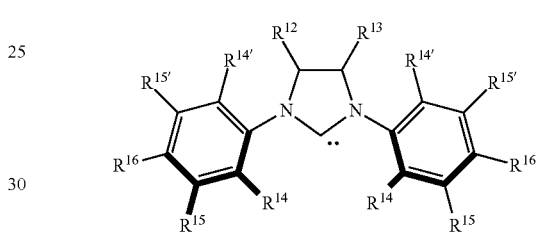

9

In some embodiments. $L^2$ is an inert ligand, wherein group 9 and/or $L^2$ contain at least one $X^2$ substituent or are substituted with at least one aliphatic and/or aromatic and/or heterocyclic alkylamino or alkylphosphine.

In some embodiments, a complex of general formula 10 is defined by general formula 14

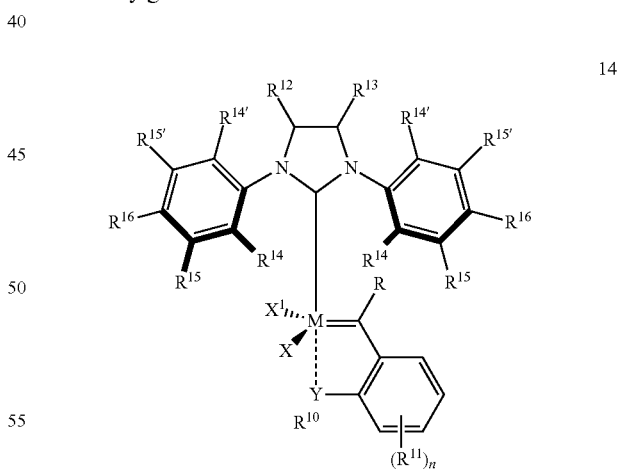

14

With respect to formula 14, M is ruthenium or osmium. In some embodiments, M is ruthenium.

With respect to formula 14, X and $X^1$ are, independently, inert ligands.

In some embodiments, X is Cl or I. In some embodiments, X is Cl. In some embodiments, X is I.

In some embodiments, both X and $X^1$ are Cl or I. In some embodiments, both X and $X^1$ are Cl. In some embodiments, both X and $X^1$ are I.

With respect to formula 14, Y is O, S, N or P. In some embodiments, Y is O.

With respect to formula 14, R is H, —$C_{1-20}$ alkyl, —$C_{2-20}$ alkenyl, —$C_{2-20}$ alkynyl or —$C_{3-10}$ aryl group. In some embodiments, R is H.

With respect to formula 14, $R^{10}$ is —$C_{1-20}$ alkyl, —$C_{5-10}$ aryl, —$C_{1-20}$ alkoxy, —$C_{5-10}$ aryloxy, —$C_{1-20}$ alkylamino, —$C_{1-20}$ protonated alkylamino, —$C_{1-20}$ alkylammonium, —$C_{1-12}$ alkylthiol, —$CH_2C(=O)$—$C_{1-6}$ alkyl, —$CH_2C(=O)$—O—$C_{1-6}$ alkyl, —$CH_2C(=O)$—$N(C_{1-6}$ alkyl$)_2$, —$CH_2C(=O)$—N—$(C_{1-6}$alkyl)-O—$C_{1-6}$ alkyl, —$CH_2C(=O)$—$C_{5-10}$ aryl, —$CH_2C(=O)$—O—$C_{5-10}$ aryl, —$CH_2C(=O)$—$N(C_{5-10}$ aryl$)_2$, —$CH_2C(=)$—N—$(C_{5-10}$ aryl)-O—$C_{5-10}$ aryl, —$C_{1-20}$ alkylphosphino, —$C_{1-20}$ alkylphosphonium, —$C_{4-10}$ heterocyclic, —$C_{4-10}$ quaternized heterocyclic group. Each of the groups listed above can be optionally substituted with —$C_{1-20}$ alkyl, —$C_{5-10}$ aryl, or a —$C_{4-10}$ heterocyclic group.

In some embodiments, $R^{10}$ is $C_{1-6}$ alkyl, such as $CH_3$, $C_2H_5$, $C_3H_7$, $C_4H_9$, etc.; or $C_{1-20}$ alkylamine, such as $C_{3-20}N_{1-2}H_{8-44}$, $C_{3-10}NH_{8-24}$, $C_{3-20}N_2H_{8-44}$, or $C_{3-20}NOH_{8-44}$, etc.

In some embodiments, $R^{10}$ is $C_{1-3}$ alkyl, —$(CH_2)_{0-4}N(C_{1-3}H_{3-7})_2$, In some embodiments, $R^{10}$ is isopropyl.

In some embodiments, $R^{10}$ is

With respect to formula 14, each $R^{11}$ is independently halogen, —$C_{1-20}$ alkyl, —$C_{1-20}$ haloalkyl, —$C_{2-20}$ alkenyl, —$C_{2-20}$ alkynyl, —$C_{5-10}$ aryl, —$C_{1-20}$ alkoxy, —$C_{2-20}$ alkenyloxy, —$C_{2-20}$ alkynyloxy, —$C_{5-10}$ aryloxy, —$C_{1-20}$ alkoxy carbonyl, —$C_{1-20}$-alkylamino, —$C_{1-20}$ protonated alkylamino, —$C_{1-20}$ alkylammonium, amino, protonated amino, —$C_{4-10}$ heterocyclic, —$C_{4-10}$ quaternized heterocyclic, —$C_{1-20}$ alkylphosphino, —$C_{1-20}$ alkylphosphonium, —$C_{1-20}$ alkylthiol, nitro, carboxyl, amido, sulfonamido, or —$C_{1-20}$ perhaloalkyl. Each of the groups listed above, except halogen, nitro, and carboxyl, is optionally substituted with —$C_{1-20}$ alkyl, —$C_{1-20}$ haloalkyl, —$C_{1-20}$ perhaloalkyl, —$C_{5-10}$ aryl, or a —$C_{4-10}$ heterocyclic group.

In some embodiments, $R^{11}$ is nitro; $C_{1-6}$ alkyl, such as $CH_3$, $C_2H_5$, $C_3H_7$, $C_4H_9$, etc.; or —$C_{1-20}$ alkylamine, such as $C_{1-20}N_{1-2}H_{3-42}$, $C_{1-10}NH_{3-22}$, $C_{2-20}N_2H_{7-44}$, or $C_{2-20}NOH_{6-44}$, etc.

In some embodiments, $R^{11}$ is nitro, —$(CH_2)_{0-4}N(C_{1-3}H_{3-7})_2$,

In some embodiments, $R^{11}$ is nitro, —$CH_2N(CH_3)_2$, —$NHCOCH_2N(CH_3)_2$,

In some embodiments, $R^4$ is nitro.

In some embodiments, $R^{11}$ is

In some embodiments, $R^{11}$ is —$CH_2N(CH_3)_2$.

In some embodiments, $R^{11}$ is —$NHCOCH_2N(CH_3)_2$.

With respect to formula 14, n is 0, 1, 2, 3, or 4. In some embodiments, n is 0. In some embodiments, n is 1.

With respect to formula 9 or 14, $R^{12}$ is H, —$C_{1-6}$ alkyl, —$C_{1-6}$ haloalkyl, —$C_{5-10}$ aryl, —$C_{1-20}$ alkylamino, —$C_{1-20}$ alkylphosphino, or —$C_{4-10}$ heterocyclic group. Each of the groups above, except H, is optionally substituted with —$C_1$, alkyl, —$C_{1-6}$ alkylamino or a —$C_{4-10}$ heterocyclic group.

In some embodiments, $R^{12}$ is H; $C_{1-6}$ alkyl, such as $CH_3$, $C_2H_5$, $C_3H_7$, $C_4H_9$, etc.; or —$C_{1-20}$ alkylamine, such as $C_{1-20}N_{1-2}H_{3-42}$, $C_{1-10}NH_{3-22}$, $C_{2-20}N_2H_{7-44}$, or $C_{2-20}NOH_{6-44}$, etc.

In some embodiments. $R^{12}$ is H, $C_{1-3}$ alkyl, $-(CH_2)_{0-4}N(C_{1-3}H_{3-7})_2$,

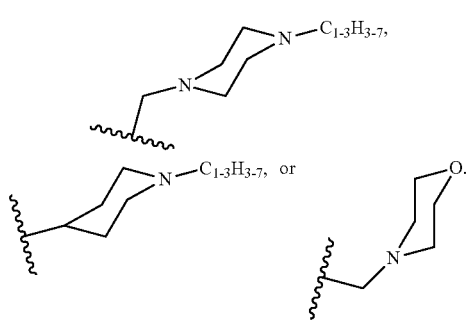

In some embodiments, $R^{12}$ is H.

With respect to formula 9 or 14, $R^{13}$ is H, $-C_{1-6}$ alkyl, $-C_{1-6}$ haloalkyl, $-C_{5-10}$ aryl, $-C_{1-20}$ alkylamino, $-C_{1-20}$ alkylphosphino, or $-C_{4-10}$ heterocyclic group. Each of the groups above, except H, is optionally substituted with $-C_{1-6}$ alkyl, $-C_{1-6}$ alkylamino or a $-C_{4-10}$ heterocyclic group.

In some embodiments, $R^{13}$ is H; $C_{1-6}$ alkyl, such as $CH_3$, $C_2H_5$, $C_3H_7$, $C_4H_9$, etc.; or $-C_{1-20}$ alkylamine, such as $C_{1-20}N_{1-2}H_{3-42}$, $C_{1-10}NH_{3-22}$, $C_{2-20}N_2H_{7-44}$, or $C_{2-20}NOH_{6-44}$, etc.

In some embodiments. $R^{13}$ is H, $C_{1-3}$ alkyl, $-(CH_2)_{0-4}N(C_{1-3}H_{3-7})_2$,

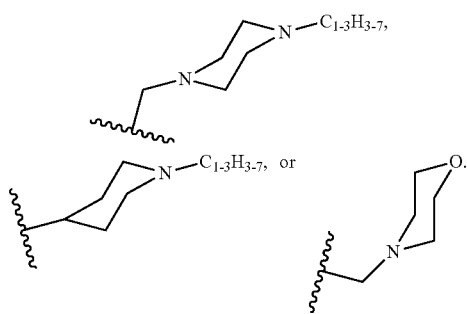

In some embodiments, $R^{13}$ is H, $-CH_2N(CH_3)_2$, $-NHCOCH_2N(CH_3)_2$,

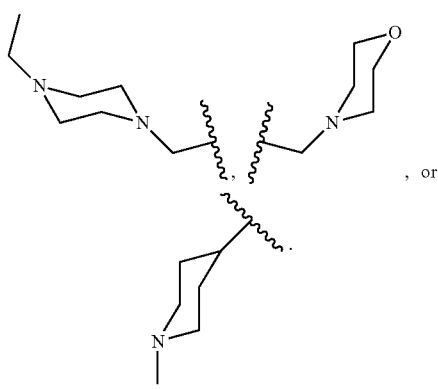

In some embodiments, $R^{13}$ is H.
In some embodiments, $R^{13}$ is $-CH_2N(CH_3)_2$.

In some embodiments, $R^{13}$ is

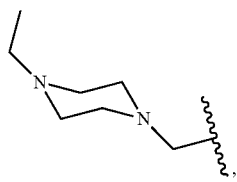 [SMILES: *CN1CCN(CC)CC1]

With respect to formula 9 or 14, each $R^{14}$ is independently H, $-C_{1-6}$ alkyl, $-C_{1-6}$ haloalkyl, $-C_{5-10}$ aryl, $-C_{1-20}$ alkylamino, $-C_{1-20}$ alkylphosphino, or $-C_{4-10}$ heterocyclic group. Each of the groups above, except H, is optionally substituted with $-C_{1-6}$ alkyl, $-C_{1-6}$ alkylamino or a $-C_{4-10}$ heterocyclic group.

In some embodiments, each $R^{14}$ is independently H; $C_{1-6}$ alkyl, such as $CH_3$, $C_2H_5$, $C_3H_7$, $C_4H_9$, etc.; or $-C_{1-20}$ alkylamine, such as $C_{1-20}N_{1-2}H_{3-42}$, $C_{1-10}NH_{3-22}$, $C_{2-20}N_2H_{7-44}$, or $C_{2-20}NOH_{6-44}$, etc.

In some embodiments, each $R^{14}$ is independently H, $C_{1-4}$ alkyl, $-(CH_2)_{0-4}N(C_{1-3}H_{3-7})_2$,

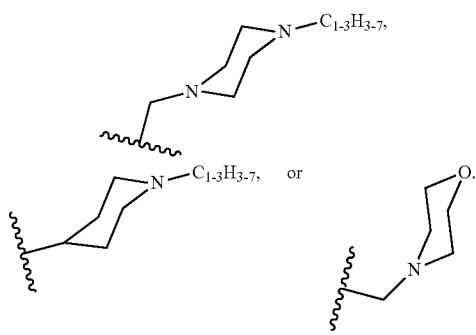

In some embodiments, at least one $R^{14}$ is methyl.
In some embodiments, both $R^{14}$ are methyl.
In some embodiments, at least one $R^{14}$ is isopropyl.
In some embodiments, both $R^{14}$ are isopropyl.

With respect to formula 9 or 14, each $R^{14'}$ is independently H, $-C_{1-6}$ alkyl, $-C_{1-6}$ haloalkyl, $-C_{5-10}$ aryl, $-C_{1-20}$ alkylamino, $-C_{1-20}$ alkylphosphino, or $-C_{4-10}$ heterocyclic group. Each of the groups above, except H, is optionally substituted with $-C_{1-6}$ alkyl, $-C_{1-6}$ alkylamino or a $-C_{4-10}$ heterocyclic group.

In some embodiments, each $R^{14'}$ is independently H; $C_{1-6}$ alkyl, such as $CH_3$, $C_2H_5$, $C_3H_7$, $C_4H_9$, etc.; or $-C_{1-20}$ alkylamine, such as $C_{1-20}N_{1-2}H_{3-42}$, $C_{1-10}NH_{3-22}$, $C_{2-20}N_2H_{7-44}$, or $C_{2-20}NOH_{6-44}$, etc.

In some embodiments, each $R^{14'}$ is independently H, $C_{1-4}$ alkyl, $-(CH_2)_{0-4}N(C_{1-3}H_{3-7})_2$,

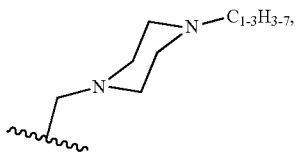

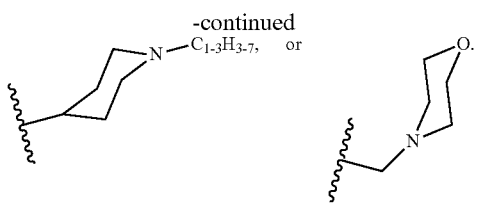

In some embodiments, at least one $R^{14'}$ is methyl.
In some embodiments, both $R^{14'}$ are methyl.
In some embodiments, at least one $R^{14'}$ is isopropyl.
In some embodiments, both $R^{14'}$ are isopropyl.
In some embodiments, both $R^{14}$ and both $R^{14'}$ are methyl.
In some embodiments, both $R^{14}$ and both $R^{14'}$ are isopropyl.

With respect to formula 9 or 14, each $R^{15}$ is independently H, —$C_{1-6}$ alkyl, —$C_{1-6}$ haloalkyl, —$C_{5-10}$ aryl, —$C_{1-20}$ alkylamino, —$C_{1-20}$ alkylphosphino, or —$C_{4-10}$ heterocyclic group. Each of the groups above, except H, is optionally substituted with —$C_{1-6}$ alkyl, —$C_{1-6}$ alkylamino or a —$C_{4-10}$ heterocyclic group.

In some embodiments, each $R^{15}$ is independently H; $C_{1-6}$ alkyl, such as $CH_3$, $C_2H_5$, $C_3H_7$, $C_4H_9$, etc.; or —$C_{1-20}$ alkylamine, such as $C_{1-20}N_{1-2}H_{3-42}$, $C_{1-10}NH_{3-22}$, $C_{2-20}N_2H_{7-44}$, or $C_{2-20}NOH_{6-44}$, etc.

In some embodiments, each $R^{15}$ is independently H, $C_{1-4}$ alkyl, —$(CH_2)_{0-4}N(C_{1-3}H_{3-7})_2$,

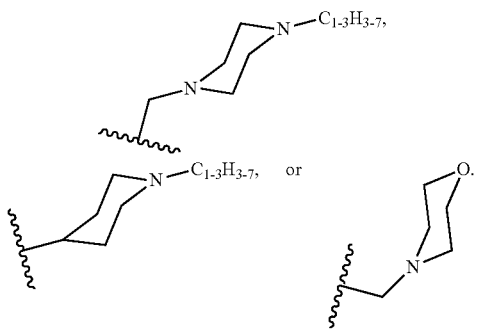

In some embodiments, at least one $R^{15}$ is H.
In some embodiments, both $R^{15}$ are H.

With respect to formula 9 or 14, each $R^{15'}$ is independently H, —$C_{1-6}$ alkyl, —$C_{1-6}$ haloalkyl, —$C_{5-10}$ aryl, —$C_{1-20}$ alkylamino, —$C_{1-20}$ alkylphosphino, or —$C_{4-10}$ heterocyclic group. Each of the groups above, except H, is optionally substituted with —$C_{1-6}$ alkyl, —$C_{1-6}$ alkylamino or a —$C_{4-10}$ heterocyclic group.

In some embodiments, each $R^{15'}$ is independently H; $C_{1-6}$ alkyl, such as $CH_3$, $C_2H_5$, $C_3H_7$, $C_4H_9$, etc.; or —$C_{1-20}$ alkylamine, such as $C_{1-20}N_{1-2}H_{3-42}$, $C_{1-10}NH_{3-22}$, $C_{2-20}N_2H_{7-44}$, or $C_{2-20}NOH_{6-44}$, etc.

In some embodiments, each $R^{15'}$ is independently H, $C_{1-4}$ alkyl, —$(CH_2)_{0-4}N(C_{1-3}H_{3-7})_2$,

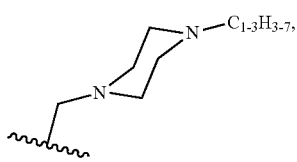

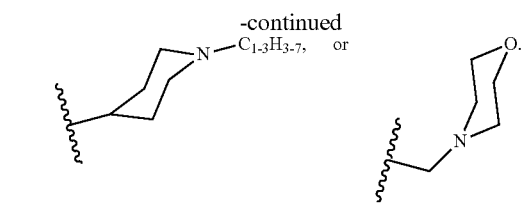

In some embodiments, at least one $R^{15'}$ is H.
In some embodiments, both $R^{15'}$ are H.
In some embodiments, both $R^{15}$ and both $R^{15'}$ are H.

With respect to formula 9 or 14, each $R^{16}$ is independently H, —$C_{1-6}$ alkyl, —$C_{1-6}$ haloalkyl, —$C_{5-10}$ aryl, —$C_{1-20}$ alkylamino, —$C_{1-20}$ alkylphosphino, or —$C_{4-10}$ heterocyclic group. Each of the groups above, except H, is optionally substituted with —$C_{1-6}$ alkyl, —$C_{1-6}$ alkylamino or a —$C_{4-10}$ heterocyclic group.

In some embodiments, each $R^{16}$ is independently H; $C_{1-6}$ alkyl, such as $CH_3$, $C_2H_5$, $C_3H_7$, $C_4H_9$, etc.; or —$C_{1-20}$ alkylamine, such as $C_{1-20}N_{1-2}H_{3-42}$, $C_{1-10}NH_{3-2}$, $C_{2-20}N_2H_{7-44}$, or $C_{2-20}NOH_{6-44}$, etc.

In some embodiments, each $R^{16}$ is independently H, $C_{1-3}$ alkyl, —$(CH_2)_{0-4}N(C_{1-3}H_{3-7})_2$,

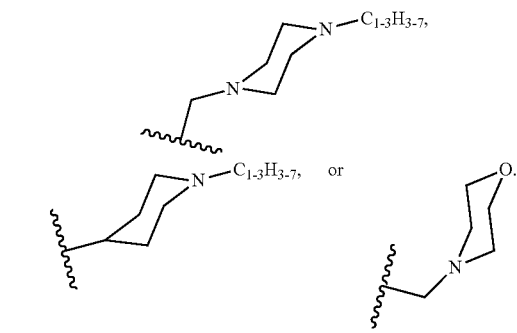

In some embodiments, $R^{16}$ is H, $C_{1-3}$ alkyl, —$CH_2N(CH_3)_2$, —$NHCOCH_2N(CH_3)_2$,

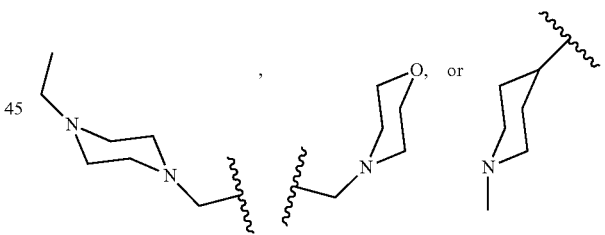

In some embodiments, at least one $R^{16}$ is H.
In some embodiments, both $R^{16}$ are H.
In some embodiments, at least one $R^{16}$ is methyl.
In some embodiments, both $R^{16}$ are methyl.
In some embodiments, at least one $R^{16}$ is

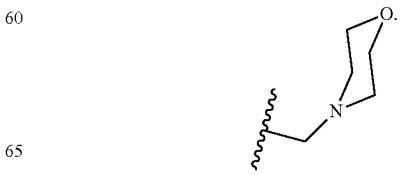

In some embodiments, both $R^{16}$ are

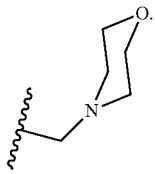 [SMILES: *CN1CCOCC1]

With respect to formula 9 or 14, $R^{12}$ and $R^{13}$, as well as $R^{14}$ and $R^{15}$, as well as $R^{14'}$ and $R^{15'}$ may be optionally linked together to form a substituted or unsubstituted, fused —$C_{4-8}$ carbocyclic ring, or a substituted or unsubstituted, fused aromatic ring.

In some embodiments, a complex of general formula 15 is defined by general formula 1

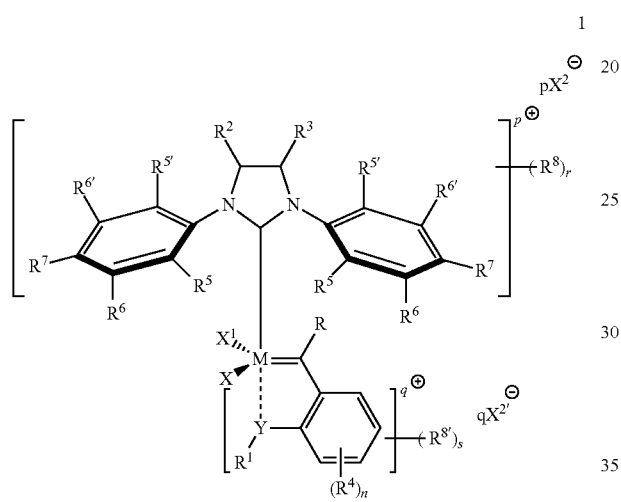

1

With respect to formula 1, M is ruthenium or osmium. In some embodiments, M is ruthenium.

With respect to formula 1, X, $X^1$, $X^2$ and $X^{2'}$ are, independently, an inert ligand.

In some embodiments, X is Cl or I. In some embodiments, X is Cl. In some embodiments, X is I.

In some embodiments, both X and $X^1$ are Cl or I. In some embodiments, both X and $X^1$ are Cl. In some embodiments, both X and $X^1$ are I.

In some embodiments, $X^2$ is Cl or I. In some embodiments, $X^2$ is Cl. In some embodiments, $X^2$ is I.

In some embodiments, $X^{2'}$ is Cl or I. In some embodiments, $X^{2'}$ is Cl. In some embodiments, $X^{2'}$ is I.

With respect to formula 1, Y is O, S, N, or P. In some embodiments, Y is O.

With respect to formula 1, R is H, —$C_{1-20}$ alkyl, —$C_{2-20}$ alkenyl, —$C_{2-20}$ alkynyl or —$C_{5-10}$ aryl group. In some embodiments, R is H.

With respect to formula 1, $R^1$ is —$C_{1-20}$ alkyl, $C_{3-8}$ cycloalkyl, —$C_{2-20}$ alkenyl, —$C_{2-20}$ alkynyl, —$C_{5-10}$ aryl, —$C_{1-20}$ alkoxy, —$C_{2-20}$ alkenyloxy, —$C_{2-20}$ alkynyloxy, —$C_{5-10}$ aryloxy, —$C_{1-20}$ alkoxycarbonyl, —$C_{1-20}$ alkylamino, —$C_{1-20}$ alkylphosphino, —$C_{1-20}$ alkylthiol, —$C_{1-20}$ alkylammonium, —$C_{1-20}$ alkylphosphonium, —$C_{1-20}$ alkylsulfonyl, —$C_{1-20}$ alkylosulfinyl, —$CH_2C(=O)$—$C_{1-6}$ alkyl, —$CH_2C(=O)$—O—$C_{1-6}$ alkyl, —$CH_2C(=O)$—N($C_{1-6}$ alkyl)$_2$, —$CH_2C(=O)$—N—($C_{1-6}$ alkyl)-O—$C_{1-6}$ alkyl, —$CH_2C(=O)$—$C_{5-10}$ aryl, —$CH_2C(=O)$—O—$C_{5-10}$ aryl, —$CH_2C(=O)$—N($C_{5-10}$ aryl)$_2$, —$CH_2C(=O)$—N—($C_{5-10}$ aryl)-O—$C_{5-10}$ aryl, —$C_{4-10}$ heterocyclic, —$C_{4-10}$ quaternized heterocyclic group. Each of these groups is optionally substituted with —$C_{1-20}$ alkyl, —$C_{5-10}$ aryl, or a —$C_{4-10}$ heterocyclic group.

In some embodiments, R is $C_{1-6}$ alkyl, such as $CH_3$, $C_2H_5$, $C_3H_7$, $C_4H_9$, etc.; or —$C_{1-20}$ alkylammonium, such as $(C_{4-20}N_{1-2}H_{12-44})^+$, $(C_{4-10}NH_{12-24})^+$, $(C_{4-20}N_2H_{12-44})^+$, or a $(C_{4-20}NOH_{12-44})^+$, etc.

In some embodiments, $R^1$ is $C_{1-3}$ alkyl, —$(CH_2)_{0-4}N^+(C_{1-3}H_{3-7})_3$,

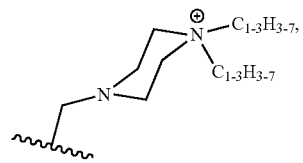

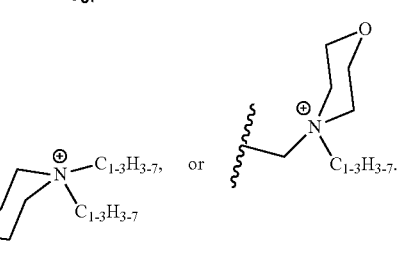

In some embodiments, $R^1$ is isopropyl.

In some embodiments, $R^1$ is

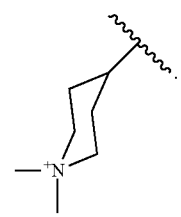 [SMILES: *C1CC[N+](C)(C)CC1]

$R^1$ may be optionally linked to X or $X^1$ to form a tridentate ligand;

With respect to formula 1, $R^2$ is H, —$C_{1-6}$ alkyl, —$C_{3-8}$ cycloalkyl, —$C_{5-10}$ aryl, —$C_{1-20}$ alkylamino, —$C_{1-20}$ alkylphosphino, —$C_{1-20}$ alkylammonium, or —$C_{1-20}$ alkylphosphonium. Each of these groups, except H, is optionally substituted with —$C_{5-10}$ aryl, —$C_{4-10}$ heterocyclic, or a —$C_{4-10}$ quaternized heterocyclic group, which in turn may be substituted with at least one nitro, —$C_{1-6}$ alkyl, —$C_{1-6}$ alkoxy, —$C_{5-10}$ aryl group or halogen.

In some embodiments, $R^2$ is H; $C_{1-6}$ alkyl, such as $CH_3$, $C_2H_5$, $C_3H_7$, $C_4H_9$, etc.; or —$C_{1-20}$ alkylammonium, such as $(C_{4-20}N_{1-2}H_{12-44})^+$, $(C_{4-10}NH_{12-24})^+$, $(C_{4-20}N_2H_{12-44})^+$, or a $(C_{4-20}NOH_{12-44})^+$, etc.

In some embodiments, $R^2$ is H, $C_{1-3}$ alkyl, —$(CH_2)_{0-4}N^+(C_{1-3}H_{3-7})_3$,

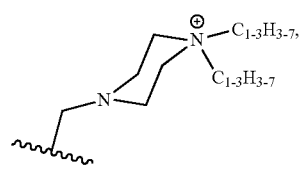

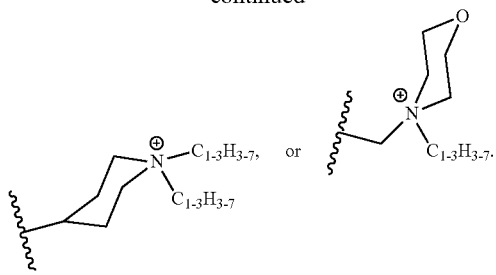

In some embodiments, $R^2$ is H.

With respect to formula 1, $R^3$ is H, —$C_{1-6}$ alkyl, —$C_{3-8}$ cycloalkyl, —$C_{5-10}$ aryl, —$C_{1-20}$ alkylamino, —$C_{1-20}$ alkylphosphino, —$C_{1-20}$ alkylammonium, or —$C_{1-20}$ alkylphosphonium. Each of these groups, except H, is optionally substituted with —$C_{5-10}$ aryl, —$C_{4-10}$ heterocyclic, or a —$C_{4-10}$ quaternized heterocyclic group, which in turn may be substituted with at least one nitro, —$C_{1-6}$ alkyl, —$C_{1-6}$ alkoxy, —$C_{5-10}$ aryl group or halogen.

In some embodiments, $R^3$ is H; $C_{1-6}$ alkyl, such as $CH_3$, $C_2H_5$, $C_3H_7$, $C_4H_9$, etc.; or —$C_{1-20}$ alkylammonium, such as $(C_{4-20}N_{1-2}H_{12-44})^+$, $(C_{4-10}NH_{12-24})^+$, $(C_{4-20}N_2H_{12-44})^+$, or a $(C_{4-20}NOH_{12-44})^+$, etc.

In some embodiments, $R^3$ is H, $C_{1-3}$ alkyl, —$(CH_2)_{0-4}N^+(C_{1-3}H_{3-7})_3$,

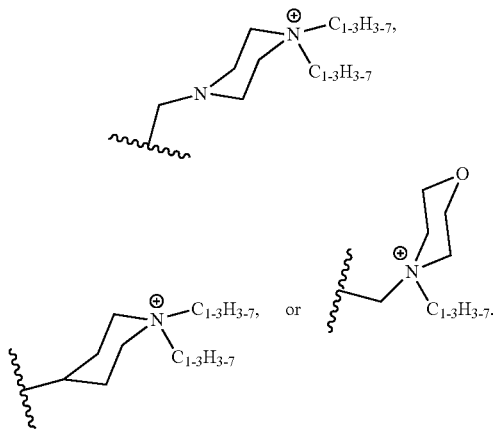

In some embodiments, $R^3$ is H, $C_{1-3}$ alkyl, —$CH_2N^+(CH_3)_3$, —$NHCOCH_2N^+(CH_3)_3$,

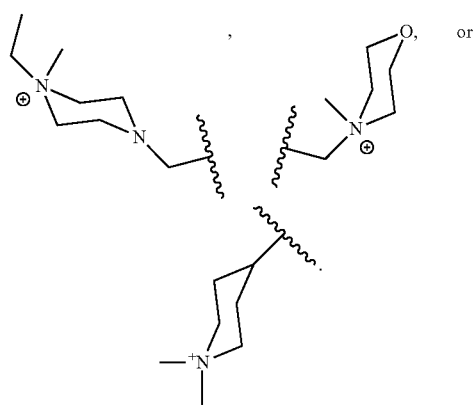

In some embodiments, $R^3$ is H.
In some embodiments, $R^3$ is —$CH_2N^+(CH_3)_3$.

In some embodiments. $R^3$ is

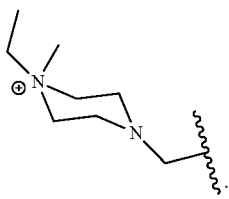 [SMILES: *CN1CC[N+](C)(CC)CC1]

With respect to formula 1, $R^2$ and $R^3$ may be optionally linked together to form a substituted or unsubstituted, fused —$C_{4-8}$ carbocyclic ring, or a substituted or unsubstituted, fused aromatic ring.

With respect to formula 1, each $R^4$ is independently halogen, —$C_{1-20}$ alkyl, —$C_{2-20}$ alkenyl, —$C_{2-20}$ alkynyl, —$C_{5-10}$ aryl, —$C_{1-20}$ alkoxy, —$C_{2-20}$ alkenyloxy, —$C_{2-20}$ alkynyloxy, —$C_{5-10}$ aryloxy, —$C_{1-20}$ alkoxycarbonyl, —$C_{1-20}$ alkylamino, —$C_{1-20}$ protonated alkylamino, amino, protonated amino, —$C_{1-20}$ alkylphosphino, —$C_{1-20}$ alkylthiol, —$C_{1-20}$ alkylammonium, —$C_{1-20}$ alkylphosphonium, —$C_{4-10}$ quaternized heterocyclic, nitro, carboxyl, amido, sulfonamido, or a —$C_{1-20}$ perhaloalkyl group. Each of these, except halogen, nitro, and carboxyl, is optionally substituted with —$C_{1-20}$ alkyl, —$C_{1-20}$ perhaloalkyl, —$C_{5-10}$ aryl, or a —$C_{4-10}$ quaternized heterocyclic group.

In some embodiments, each $R^4$ is independently nitro; $C_{1-6}$ alkyl, such as $CH_3$, $C_2H_5$, $C_3H_7$, $C_4H_9$, etc.; or —$C_{1-20}$ alkylammonium, such as $(C_{4-20}N_{1-2}H_{12-44})^+$, $(C_{4-10}NH_{12-24})^+$, $(C_{4-20}N_2H_{12-44})^+$, or a $(C_{4-20}NOH_{12-44})^+$, etc.

In some embodiments, each $R^4$ is independently nitro, —$(CH_2)_{0-4}N^+(C_{1-3}H_{3-7})_3$,

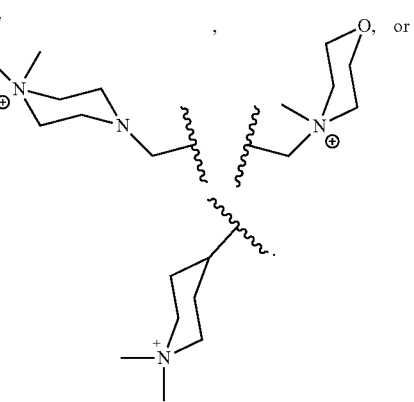

In some embodiments, each $R^4$ is independently nitro, —$CH_2N^+(CH_3)_3$, —$NHCOCH_2N^+(CH_3)_3$, In some embodiments, each $R^4$ is independently nitro.

In some embodiments, $R^4$ is

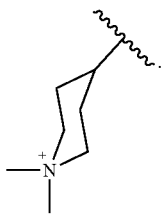 [SMILES: *C1CC[N+](C)(C)CC1]

In some embodiments, $R^4$ is $-CH_2N_3^+(CH_3)_3$.
In some embodiments, $R^4$ is $-NHCOCH_2N^+(CH_3)_3$.
With respect to formula 1, n is 0, 1, 2, 3, or 4;
In some embodiments, n is 0.
In some embodiments, n is 1.

With respect to formula 1, each $R^5$ is independently H, $-C_{1-6}$ alkyl, $-C_{1-20}$ alkylamino, $-C_{1-20}$ alkylphosphino, $-C_{1-20}$ alkylammonium, $-C_{1-20}$ alkylphosphonium, $-C_{4-10}$ heterocyclic, or a $-C_{4-10}$ quaternized heterocyclic group. Each of these groups, except H, is optionally substituted with a $-C_{4-10}$ quaternized heterocyclic group, $-C_{1-6}$ alkyl, or $-C_{5-10}$ aryl, which in turn may be substituted with nitro, $-C_{1-6}$ alkyl, $-C_{1-6}$ alkoxy, $-C_{5-10}$ aryl group or halogen.

In some embodiments, each $R^5$ is independently H; $C_{1-6}$ alkyl, such as $CH_3$, $C_2H_5$, $C_3H_7$, $C_4H_9$, etc.; or $-C_{1-20}$ alkylammonium, such as $(C_{4-20}N_{1-2}H_{12-44})^+$, $(C_{4-10}NH_{12-24})^+$, $(C_{4-20}N_2H_{12-44})^+$, or a $(C_{4-20}NOH_{12-44})^+$, etc.

In some embodiments, each $R^5$ is independently H, $C_{1-4}$ alkyl, $-(CH_2)_{0-4}N^+(C_{1-3}H_{3-7})_3$,

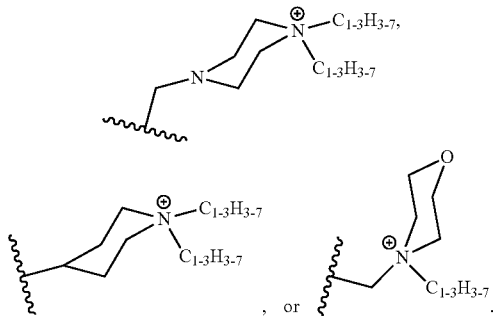

In some embodiments, at least one $R^5$ is methyl.
In some embodiments, both $R^5$ are methyl.
In some embodiments, at least one $R^5$ is isopropyl.
In some embodiments, both $R^5$ are isopropyl.

With respect to formula 1, each $R^{5'}$ is independently H, $-C_{1-6}$ alkyl, $-C_{1-20}$ alkylamino, $-C_{1-20}$ alkylphosphino, $-C_{1-20}$ alkylammonium, $-C_{1-20}$ alkylphosphonium, $-C_{4-10}$ heterocyclic, or a $-C_{4-10}$ quaternized heterocyclic group. Each of these groups, except H, is optionally substituted with a $-C_{4-10}$ quaternized heterocyclic group, $-C_{1-6}$ alkyl, or $-C_{5-10}$ aryl, which in turn may be substituted with nitro, $-C_{1-6}$ alkyl, $-C_{1-6}$ alkoxy, $-C_{5-10}$ aryl group or halogen.

In some embodiments, each $R^{5'}$ is independently H; $C_{1-6}$ alkyl, such as $CH_3$, $C_2H_5$, $C_3H_7$, $C_4H_9$, etc.; or $-C_{1-20}$ alkylammonium, such as $(C_{4-20}N_{1-2}H_{12-44})^+$, $(C_{4-10}NH_{12-24})^+$, $(C_{4-20}N_2H_{12-44})^+$, or a $(C_{4-20}NOH_{12-44})^+$, etc.

In some embodiments, each $R^{5'}$ is independently H, $C_{1-4}$ alkyl, $-(CH_2)_{0-4}N^+(C_{1-3}H_{3-7})_3$,

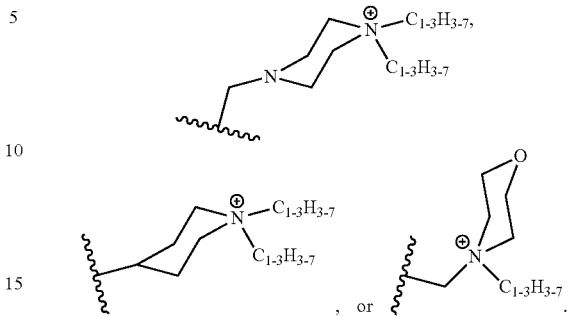

In some embodiments, at least one $R^{5'}$ is methyl.
In some embodiments, both $R^{5'}$ are methyl.
In some embodiments, at least one $R^{5'}$ is isopropyl.
In some embodiments, both $R^{5'}$ are isopropyl.
In some embodiments, both $R^5$ and both $R^{5'}$ are methyl.
In some embodiments, both $R^5$ and both $R^{5'}$ are isopropyl.

With respect to formula 1, each $R^6$ is independently H, $-C_{1-6}$ alkyl, $-C_{1-20}$ alkylamino, $-C_{1-20}$ alkylphosphino, $-C_{1-20}$ alkylammonium, $-C_{1-20}$ alkylphosphonium, $-C_{4-10}$ heterocyclic, or a $-C_{4-10}$ quaternized heterocyclic group. Each of these groups, except H, is optionally substituted with a $-C_{4-10}$ quaternized heterocyclic group, $-C_{1-6}$ alkyl, or $-C_{5-10}$ aryl, which in turn may be substituted with nitro, $-C_{1-6}$ alkyl, $-C_{1-6}$ alkoxy, $-C_{5-10}$ aryl group or halogen.

In some embodiments, each $R^6$ is independently H; $C_{1-6}$ alkyl, such as $CH_3$, $C_2H_5$, $C_3H_7$, $C_4H_9$, etc.; or $-C_{1-20}$ alkylammonium, such as $(C_{4-20}N_{1-2}H_{12-44})^+$, $(C_{4-10}NH_{12-24})^+$, $(C_{4-20}N_2H_{12-44})^+$, or a $(C_{4-20}NOH_{12-44})^+$, etc.

In some embodiments, each $R^6$ is independently H, $C_{1-4}$ alkyl, $-(CH_2)_{0-4}N(C_{1-3}H_{3-7})_3$,

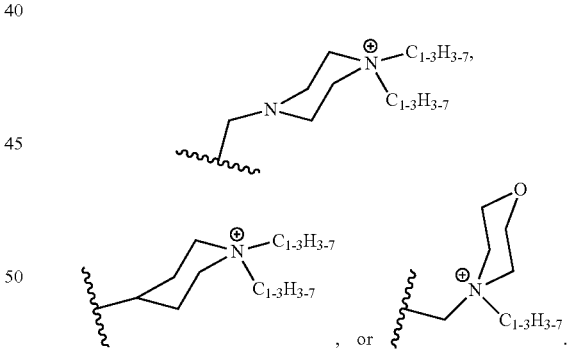

In some embodiments, at least one $R^6$ is H.
In some embodiments, both $R^6$ are H.

With respect to formula 1, each $R^{6'}$ is independently H, $-C_{1-6}$ alkyl, $-C_{1-20}$ alkylamino, $-C_{1-20}$ alkylphosphino, $-C_{1-20}$ alkylammonium, $-C_{1-20}$ alkylphosphonium, $-C_{4-10}$ heterocyclic, or a $-C_{4-10}$ quaternized heterocyclic group. Each of these groups, except H, is optionally substituted with a $-C_{4-10}$ quaternized heterocyclic group, $-C_{1-6}$ alkyl, or $-C_{5-10}$ aryl, which in turn may be substituted with nitro, $-C_{1-6}$ alkyl, $-C_{1-6}$ alkoxy, $-C_{5-10}$ aryl group or halogen.

In some embodiments, each $R^{6'}$ is independently H; $C_{1-6}$ alkyl, such as $CH_3$, $C_2H_5$, $C_3H_7$, $C_4H_9$, etc.; or $-C_{1-20}$ alkylammonium, such as $(C_{4-20}N_{1-2}H_{12-44})^+$, $(C_{4-10}NH_{12-24})^+$, $(C_{4-20}N_2H_{12-44})^+$, or a $(C_{4-20}NOH_{12-44})^+$, etc.

In some embodiments, each $R^{6'}$ is independently H, $C_{1-4}$ alkyl, $-(CH_2)_{0-4}N^+(C_{1-3}H_{3-7})_3$,

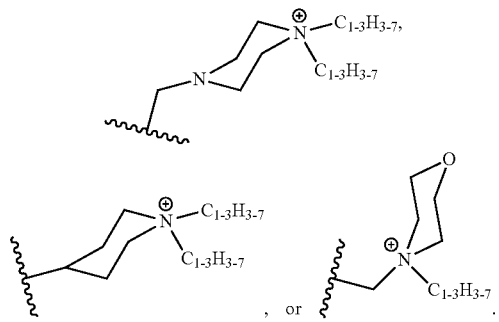

, or

In some embodiments, at least one $R^{6'}$ is H.

In some embodiments, both $R^{6'}$ are H.

In some embodiments, both $R^6$ and both $R^{6'}$ are H.

With respect to formula 1, each $R^7$ is independently H, $-C_{1-6}$ alkyl, $-C_{1-20}$ alkylamino, $-C_{1-20}$ alkylphosphino, $-C_{1-20}$ alkylammonium, $-C_{1-20}$ alkylphosphonium, $-C_{4-10}$ heterocyclic, or a $-C_{4-10}$ quaternized heterocyclic group. Each of these groups, except H, is optionally substituted with a $-C_{4-10}$ quaternized heterocyclic group, $-C_{1-6}$ alkyl, or $-C_{5-10}$ aryl, which in turn may be substituted with nitro, $-C_{1-6}$ alkyl, $-C_{1-6}$ alkoxy, $-C_{5-10}$ aryl group or halogen.

In some embodiments, each $R^7$ is independently H; $C_{1-6}$ alkyl, such as $CH_3$, $C_2H_5$, $C_3H_7$, $C_4H_9$, etc.; or $-C_{1-20}$ alkylammonium, such as $(C_{4-20}N_{1-2}H_{12-44})^+$, $(C_{4-10}NH_{12-24})^+$, $(C_{4-20}N_2H_{12-44})^+$, or a $(C_{4-20}NOH_{12-44})^+$, etc.

In some embodiments, each $R^7$ is independently H, $C_{1-3}$ alkyl, $-(CH_2)_{0-4}N(C_{1-3}H_{3-7})_3$,

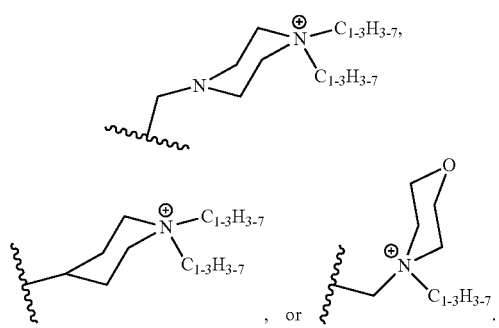

, or

In some embodiments, each $R^7$ is independently H, $C_{1-3}$ alkyl, $-CH_2N^+(CH_3)_3$, $-NHCOCH_2N^+(CH_3)_3$,

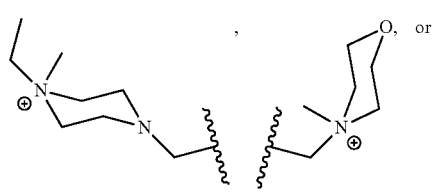

,

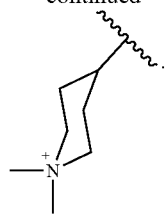

In some embodiments, at least one $R^7$ is H.
In some embodiments, both $R^7$ are H.
In some embodiments, at least one $R^7$ is methyl.
In some embodiments, both $R^7$ are methyl.
In some embodiments, at least one $R^7$ is

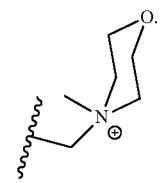 [SMILES: *C[N+]1(C)CCOCC1]

In some embodiments, both $R^7$ are

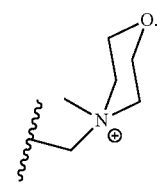 [SMILES: *C[N+]1(C)CCOCC1]

With respect to formula 1, $R^5$ and $R^6$, as well as $R^{5'}$ and $R^{6'}$ may be optionally linked together to form a substituted or unsubstituted, fused $-C_{4-8}$ carbocyclic ring, or a substituted or unsubstituted, fused aromatic ring.

With respect to formula 1, each $R^8$ is independently $-C_{1-20}$ alkyl, $-C_{3-8}$ cycloalkyl, $-C_{2-20}$ alkenyl, or $-C_{2-20}$ alkynyl. Each of these is optionally substituted with one or more halogen atoms, $-C_{5-10}$ aryl, $-C(=O)-C_{1-6}$ alkyl, $-C(=O)-O-C_{1-6}$ alkyl, $-C(=O)-N(C_{1-6}$ alkyl$)_2$, $-C(=O)-N-(C_{1-6}$ alkyl$)-O-C_{1-6}$ alkyl, $-C(=O)-C_{5-10}$ aryl, $-C(=O)-O-C_{5-10}$aryl, $-C(=O)-N(C_{5-10}$ aryl$)_2$, or $-C(=O)-N-(C_{5-10}$ aryl$)-O-C_{5-10}$ aryl group;

With respect to formula 1, p is 1, 2, 3, 4, or 5.

With respect to formula 1, r is 0, 1, 2, or 3.

With respect to formula 1, each $R^{8'}$ is independently H, $-C_{1-20}$ alkyl, $C_{3-8}$ cycloalkyl, $-C_{2-20}$ alkenyl, or $-C_{2-20}$ alkynyl.

With respect to formula 1, q is 0, 1, 2 or 3.

With respect to formula 1, s is 0, 1, 2, or 3.

With respect to formula 1, at least one substituent among $R^2$, $R^3$, $R^5$, $R^{5'}$, $R^6$, $R^{6'}$, $R^7$ contains a quaternary onium group.

In some embodiments, a complex of formula 1, obtained by a method described herein, may be optionally subjected to a further reaction with a compound of formula $R^{8'}X^{2'}$, giving a different complex of formula 1, wherein $R^{8'}$ and $X^{2'}$ are as defined above.

In some embodiments, in formula 14 symbol M is ruthenium;

X and $X^1$ are an inert ligand;

Y is O;

$R^{10}$ is —$C_{1-12}$ alkyl, —$C_{1-12}$ haloalkyl, —$C_{5-10}$ aryl, —$C_{1-12}$ alkoxy, —$C_{5-10}$ aryloxy, —$C_{1-12}$ alkoxy carbonyl, —$C_{1-12}$ alkylamino, —$C_{4-10}$ heterocyclic group, each optionally substituted with —$C_{1-12}$ alkyl, —$C_{5-10}$ aryl or —$C_{4-10}$ heterocyclic group;

$R^{11}$ is halogen, —$C_{1-12}$ alkyl, —$C_{1-12}$ haloalkyl, aryl, —$C_{1-12}$ alkoxy, —$C_{5-10}$ aryloxy, —$C_{1-12}$ alkoxy carbonyl, —$C_{1-12}$ alkylamino, amino, —$C_{1-12}$ alkylphosphino, —$C_{4-10}$ heterocyclic, nitro, carboxyl, amido, sulfonamido group; each optionally substituted with —$C_{1-12}$ alkyl, —$C_{1-12}$ haloalkyl, —$C_{1-12}$ perhaloalkyl, —$C_{5-10}$ aryl, —$C_{4-10}$ heterocyclic group;

n is 0, 1 or 2;

$R^{12}$, $R^{13}$, $R^{14}$, $R^{14'}$, $R^{15}$, $R^{15'}$, $R^{16}$ are, independently, H, —$C_{1-6}$ alkyl, —$C_{1-6}$ haloalkyl, —$C_{5-10}$ aryl, —$C_{1-6}$ alkylamino, —$C_{1-6}$ alkylphosphino, —$C_{4-10}$ heterocyclic group, each optionally substituted with —$C_{1-6}$ alkyl or —$C_{4-10}$ heterocyclic group;

$R^{12}$ and $R^{13}$ as well as $R^{14}$ and $R^{15}$ as well as $R^{14'}$ and $R^{15'}$ may be optionally linked together to form a substituted or unsubstituted, fused —$C_{4-8}$ carbocyclic ring, or a substituted or unsubstituted, fused aromatic ring.

In some embodiments related to formula 14 symbol M is ruthenium;

X, $X^1$ are independently Cl, Br or I;

R is H;

$R^{10}$ is iso-propyl group or 1-methyl-4-piperidinyl group;

$R^{11}$ is a nitro or —$NMe_2$ group; and/or n is 0 or 1.

In some embodiments, the compound of formula 14 is obtained by reacting the compound of formula 11 with an intermediate of formula 2a or 2b.

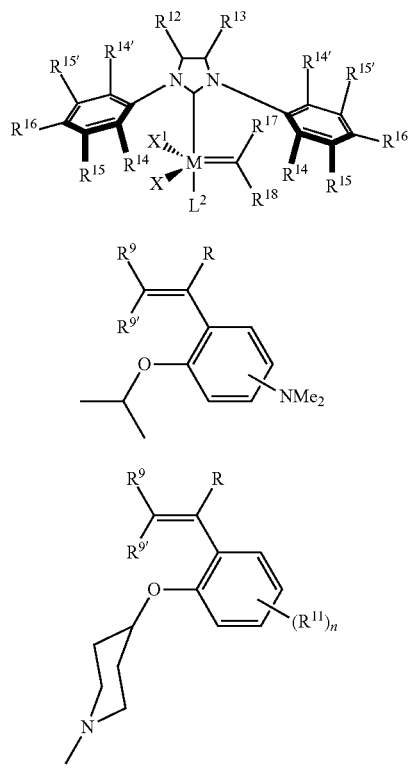

All groups of formula 11 are as defined above.

With respect to formula 2a or formula 2b, R is H; $R^9$, $R^{9'}$ are a methyl or ethyl group; $R^{11}$ is an electron acceptor group; and n is 0 or 1.

In some embodiments, in formula 9:

substituents $R^{12}$, $R^{13}$ are, independently, H, —$CH_2NMe_2$,

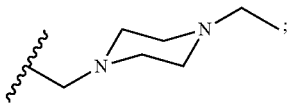 [SMILES: *CN1CCN(CC)CC1]

$R^{14}$, $R^{14'}$ are a methyl or iso-propyl group;

$R^{15}$, $R^{15'}$ are H; and/or $R^{16}$ is H, methyl, or

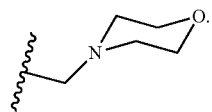 [SMILES: *CN1CCOCC1]

In some embodiments, the reaction is carried out in $R^8X^2$ as a solvent. In some embodiments, $R^8X^2$ is $CH_3Cl$, $CH_3I$, $CH_3Br$, $(CH_3)_2SO_4$.

In some embodiments, the reaction is carried out in a solvent selected from solvents such as methanol, ethanol, ethyl acetate, iso-propanol, tert-butanol, sec-butanol, diethyl ether, n-propyl ether, diisopropyl ether, tert-butyl-methyl ether, cyclopentyl-metyl ether, 1,2-dioxane, 1,3-dioxane, 1,4-dioxane, dimethylformamide, tetrahydrofurane, dichloromethane, dichloroethane, trichloromethane, tetrachloromethane, tetrachloroethane, pentane, hexane, heptane, benzene, toluene, xylene or any mixture thereof. In some embodiments, a solvent is selected from the group consisting of methanol, ethanol, dichloromethane or ethyl acetate or any mixture thereof.

In some embodiments, $TR^{19}(R^{19'})(R^{19''})$ is trimethylamine.

In some embodiments, the reaction is carried out at a temperature in the range from 0° C. to 120° C. or from 20° C. to 80° C.

In some embodiments, the reaction is carried out within the period from 0.1 hour to 96 hours, or from 1 hour to 72 hours.

In some embodiments, the reaction is carried out under atmospheric pressure.

In some embodiments, the reaction is carried out under elevated pressure.

Some embodiments relate to compositions of matter comprising, or consisting essentially of, compounds that are complexes of general formula 1, as described above.

With respect to formula 1, in some embodiments:

symbol M is ruthenium;

X, $X^1$, $X^2$ and $X^{2'}$ are, independently, halogen, —$C_{1-5}$ carboxyl. —$C_{1-6}$ alkyl, —$C_{5-10}$ aryl, —$C_{1-6}$ alkoxy, —$C_{5-10}$ aryloxy, —$C_{1-5}$ alkylthiol, —$C_{1-6}$ alkylsulfonyl, —$CH_3SO_4$, benzoate, or benzoic group;

Y is O, S or N;

R is H, —$C_{1-5}$ alkyl or —$C_{5-10}$ aryl group;

$R^1$ is —$C_{1-6}$ alkyl, $C_{3-8}$ cycloalkyl. —$C_{5-10}$ aryl, —$C_{5-10}$ aryloxy, —$C_{1-6}$ alkylamino, —$C_{1-6}$ alkylammonium, —$C_{4-10}$ heterocyclic, —$C_{4-10}$ quaternized N-heterocyclic, —$CH_2C$(=O)—$C_{1-6}$ alkyl, —$CH_2C$(=O)—O—$C_{1-6}$ alkyl, —$CH_2C$(=O)—$N(C_{1-6}$ alkyl$)_2$, —$CH_2C$(=O)—N—$(C_{1-6}$ alkyl)-O—$C_{1-6}$ alkyl, —$CH_2C$(=O)—$C_{5-10}$ aryl, —$CH_2C$(=O)—O—$C_{5-10}$ aryl, —$CH_2C$(=O)—$N(C_{5-10}$ aryl$)_2$, —$CH_2C$(=O)—N—$(C_{5-10}$ aryl)-O—$C_{5-10}$ aryl group;

$R^2$, $R^3$ are, independently, H, —$C_{1-6}$ alkyl, —$C_{1-20}$ alkylamino, —$C_{1-20}$ alkylammonium group, optionally substituted with —$C_{5-10}$ aryl, —$C_{4-10}$ N-heterocyclic, —$C_{4-10}$ quaternized N-heterocyclic group, which each in turn may be substituted with one or more nitro, —$C_{1-5}$ alkyl, —$C_{1-5}$ alkoxy, phenyl group or halogen;

$R^2$ and $R^3$ may be optionally linked together to form a substituted or unsubstituted, fused —$C_{4-8}$ carbocyclic ring, or a substituted or unsubstituted, fused aromatic ring;

$R^4$ is halogen, —$C_{1-6}$ alkyl, —$C_{5-10}$ aryl, —$C_{1-6}$ alkoxy, —$C_{5-10}$ aryloxy, —$C_{1-6}$ alkoxy carbonyl, —$C_{1-20}$ protonated alkylamino, protonated amino, —$C_{4-10}$ heterocyclic, —$C_{1-12}$alkylammonium, —$C_{4-10}$ quaternized N-heterocyclic, nitro, carboxyl, amido, sulfonamido, —$C_{1-20}$ perhaloalkyl group, each optionally substituted with —$C_{1-6}$ alkyl, —$C_{1-6}$perhaloalkyl, —$C_{5-10}$aryl, —$C_{4-10}$quaternized N-heterocyclic group;

n is 0, 1, 2 or 3;

$R^5$, $R^{5'}$, $R^6$, $R^{6'}$, $R^7$ are, independently, H, —$C_{1-6}$ alkyl, —$C_{1-16}$alkylammonium, —$C_{4-10}$ quaternized N-heterocyclic group, each optionally substituted with —$C_{4-10}$ quaternized heterocyclic group;

$R^8$ is —$C_{1-6}$ alkyl group;

p is 1, 2, 3 or 4;

$R^{8'}$ is H, —$C_{1-6}$ alkyl; and/or q is 0, 1 or 2.

In some embodiments related to formula 1:

M is ruthenium;

X, $X^1$, $X^2$ and $X^{2'}$ are, independently, halogen, $CF_3CO_2$, $CH_3CO_2$, MeO, EtO, PhO, $(NO_2)PhO$, $CH_3SO_3$, $CF_3SO_3$, tosylate, $CH_3SO_4$ group;

Y is O;

R is H;

$R^1$ is —$C_{1-6}$ alkyl, —$C_{5-10}$ aryl, —$C_{1-6}$ alkylammonium, —$C_{4-10}$ quaternized N-heterocyclic group;

$R^2$, $R^3$ are, independently, H, —$C_{1-6}$ alkyl, —$C_{1-12}$alkylammonium group, which may be optionally substituted with —$C_{4-10}$ quaternized N-heterocyclic group, which in turn may be substituted with at least one —$C_{1-6}$ alkyl, —$C_{1-5}$ alkoxy, phenyl group or halogen;

$R^4$ is halogen, —$C_{5-10}$ aryl, —$C_{1-6}$ alkoxy, —$C_{5-10}$ aryloxy, —$C_{1-12}$ alkylammonium, —$C_{1-12}$ protonated alkylamino, protonated amino, —$C_{4-10}$ quaternized N-heterocyclic, nitro, amido, sulfonamido, —$C_{1-20}$ perhaloalkyl group, where each may be optionally substituted with —$C_{1-6}$ alkyl, —$C_{1-6}$perhaloalkyl, —$C_{5-10}$aryl, —$C_{4-10}$quaternized N-heterocyclic group;

n is 0, 1 or 2;

$R^5$, $R^{5'}$, $R^6$, $R^{6'}$, $R^7$ are, independently, H, —$C_{1-6}$ alkyl, —$C_{1-12}$alkylammonium, —$C_{4-10}$ quaternized N-heterocyclic group, each optionally substituted with —$C_{4-10}$ quaternized heterocyclic group;

$R^8$ is —$C_{1-6}$ alkyl group;

p is 1 or 2;

$R^{8'}$ is H, —$C_{1-6}$ alkyl group; and/or q is 0 or 1;

In some embodiments related to formula 1, X, $X^1$, $X^2$ and $X^{2'}$ are, independently, halogen; or X, $X^1$, $X^2$ and $X^{2'}$ are, independently, chlorine or iodine.

In some embodiments related to formula 1, R is H, $R^1$ is an iso-propyl group or

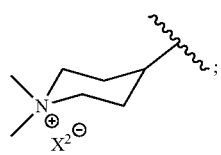

and/or $X^2$ is an anionic ligand.

In some embodiments related to formula 1, substituents $R^2$, $R^3$ are, independently, H,

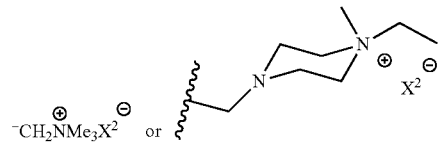

group; and/or $X^2$ is an anionic ligand.

In some embodiments related to formula 1, substituent $R^4$ is a nitro or

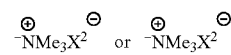

group; $X^2$ and $X^{2'}$ are independently anionic ligands; and/or n is 0 or 1.

In some embodiments related to formula 1, substituents $R^5$ and $R^{5'}$ are a methyl or iso-propyl group; $R^6$ and $R^{6'}$ are H; and/or $R^7$ is H, a methyl group or

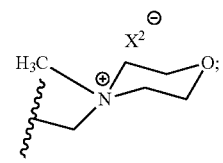

and $X^2$ is an anionic ligand.

In some embodiments related to formula 1, substituent $R^8$ is a nitro or methyl group; p is 1 or 2; $R^{8'}$ is H, a methyl group; q is 0 or 1.

Some embodiments include complexes of any of formulae 49-55 and 58-62

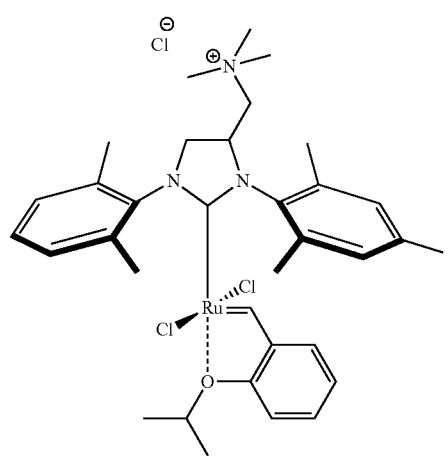

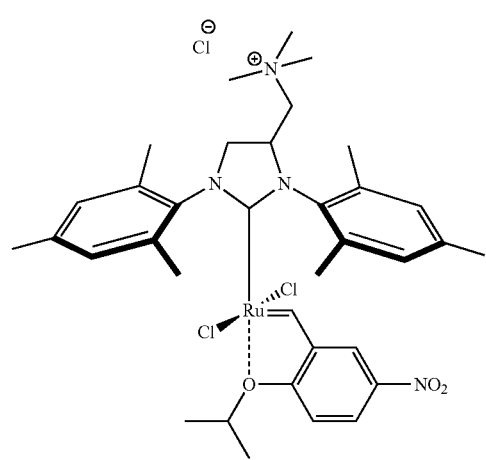
50
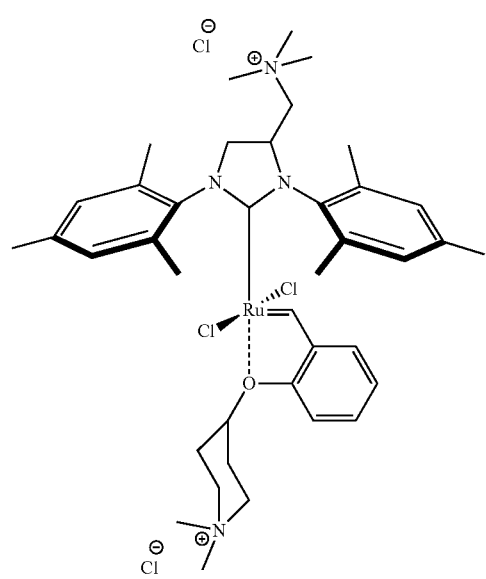
51
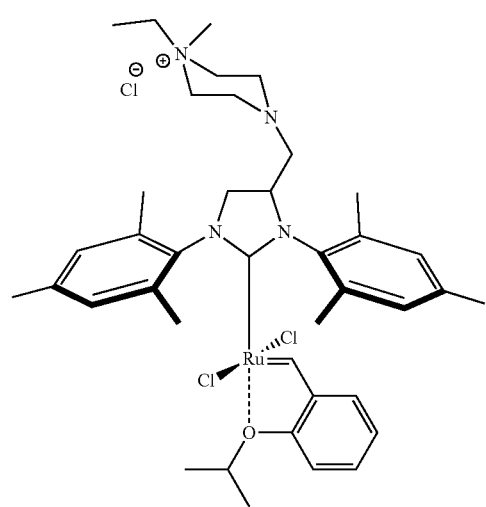
52
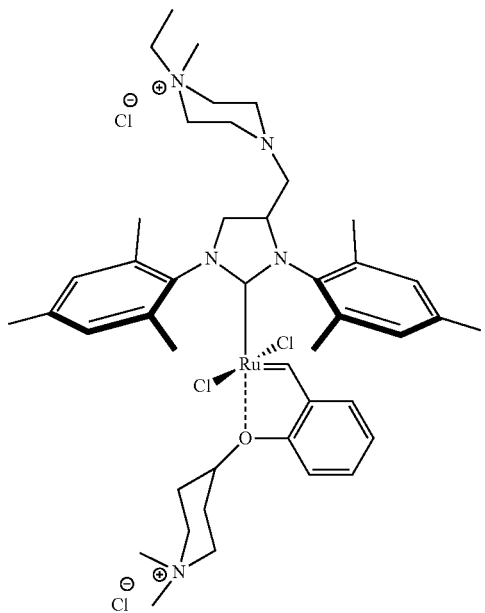
53
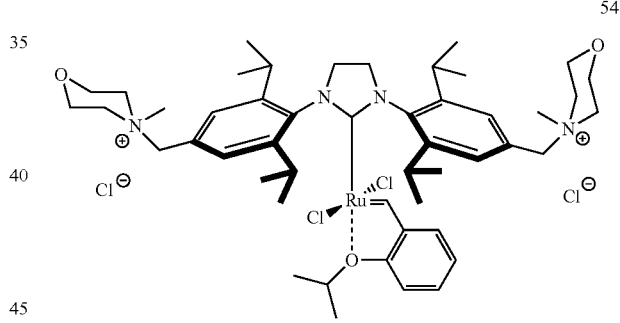
54
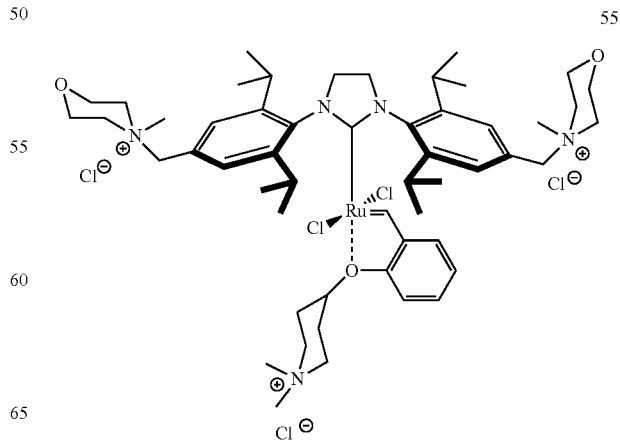
55

-continued
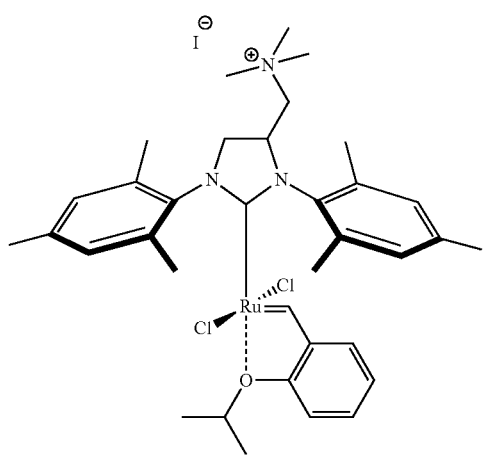
58
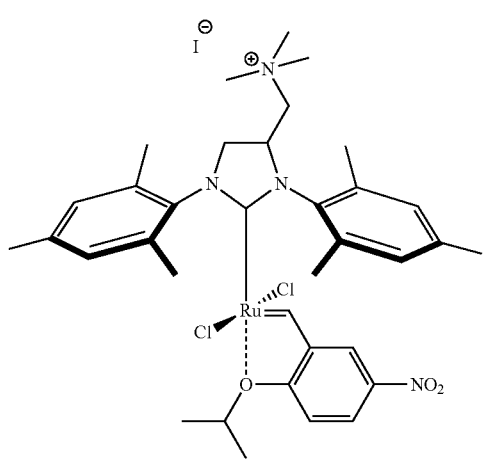
59
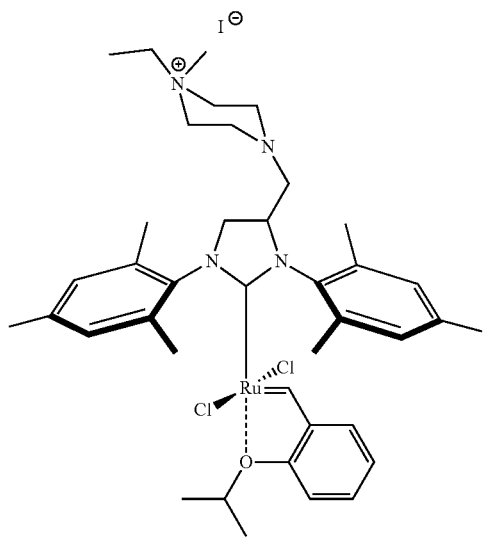
60
-continued
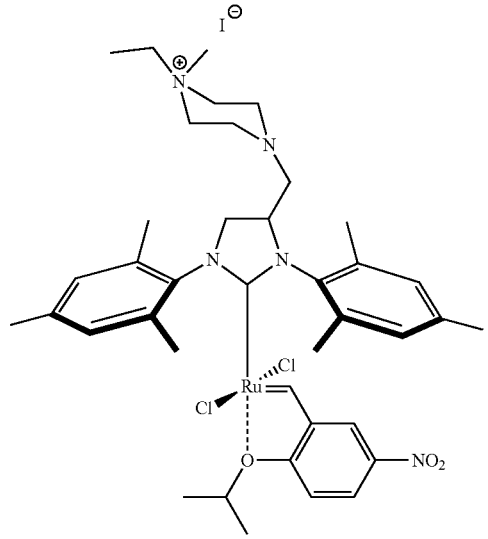
61
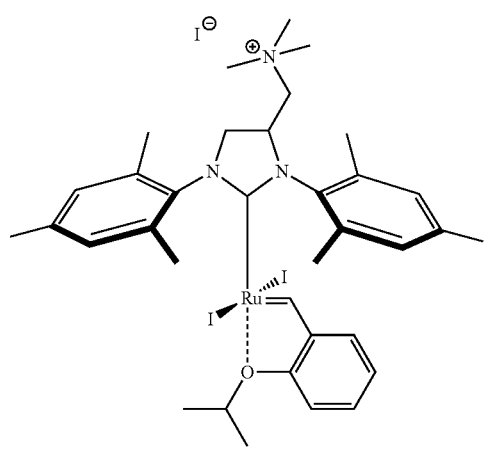
62
Some embodiments include intermediates of formulae 2a and 2b
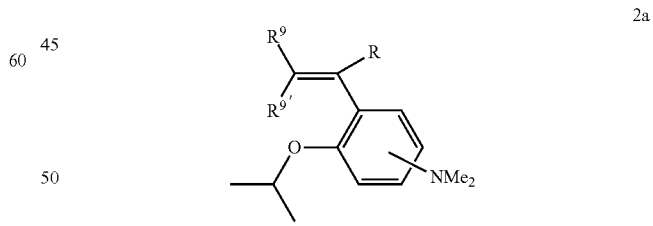
2a
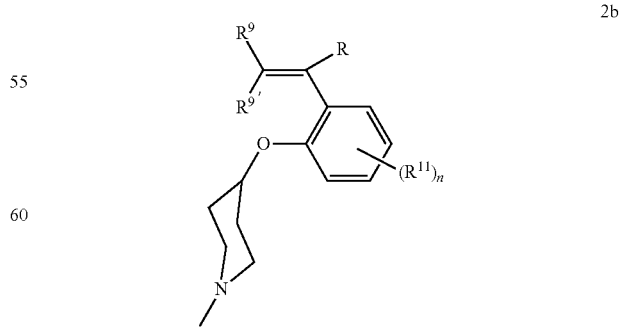
2b
wherein R is H;
R$^9$, R$^{9'}$ are a methyl or ethyl group;

m is 0 or 1; $R^{11}$ is an electron acceptor group; and/or
n is 0 or 1;

Some embodiments include the use of complexes of formula 1 as (pre)catalysts in metathesis reactions, or complexes of formula 1 are used as (pre)catalysts in a ring-closing metathesis (RCM), cross metathesis (CM), homometathesis, alken-alkyn (en-yn) metathesis.

In some embodiments, complexes of formula 1 are used as (pre)catalysts in a ring opening metathesis polymerization (ROMP).

Some embodiments include a method of carrying out an olefin metathesis reaction, characterized in that at least one olefin is contacted with a complex of formula 1 as a (pre) catalyst.

In some embodiments, the metathesis reaction is carried out in a mixture of water and an alcohol, or the metathesis reaction is carried out in water.

In some embodiments, the metathesis reaction is carried out in an organic solvent.

In some embodiments, a metathesis reaction product is purified from the heavy metal pollutants by filtering the reaction mixture through the adsorbent layer.

In some embodiments, a metathesis reaction product is purified from the heavy metal pollutants by adding an appropriate adsorbent to the reaction mixture and by filtration.

In some embodiments, the adsorbent is selected from the group consisting of silica, alumina, activated alumina, diatomaceous earth and activated carbon. In some embodiments, the adsorbent is silica gel.

In some embodiments, a reaction product is purified from the heavy metal pollutants by extraction with water.

The terms which are not defined below should have the broadest meaning known in the art.

Unless otherwise indicated, when a compound or chemical structural feature is referred to as being "optionally substituted," it includes a feature that has no substituents (i.e. unsubstituted), or a feature that is "substituted," meaning that the feature has one or more substituents, provided that adding the substituent results in a stable compound. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, amino, phosphine, ammonium, phosphonium, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, etc.

For convenience, the term "molecular weight" is used with respect to a moiety or part of a molecule to indicate the sum of the atomic masses of the atoms in the moiety or part of a molecule, even though it may not be a complete molecule.

The term "aryl group," as used herein, refers to an aromatic mono- or polycyclic hydrocarbon substituent of the indicated number of carbon atoms. The examples of an aryl group include but are not limited to phenyl, tolyl, naphthyl groups.

The term "heterocyclic group," as used herein, refers to an aromatic and non-aromatic cyclic substituent of the indicated number of carbon atoms in which any one or more carbon atoms is replaced with a heteroatom such as nitrogen, phosphorus, sulfur, oxygen, with the proviso that the ring of said group does not contain two adjacent oxygen or sulfur atoms. Non-aromatic heterocyclic groups may contain from 4 to 10 atoms in a ring, while aromatic heterocyclic groups must have at least 5 atoms in a ring. The heterocyclic groups include also benzo-fused ring systems. Examples of non-aromatic heterocyclic groups include but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, 2-pyrrolinyl, indolinyl groups. Examples of aromatic heterocyclic groups include but are not limited to pyridinyl, imidazolyl, pyrimidinyl, pyrazolyl, triazolyl, pyrazinyl, furyl, thienyl, isoxazolyl, oxazolyl groups. The foregoing groups may be C-attached or N-attached. For example, a substituent derived from attaching pyrrol may be pyrrol-1-yl (N-attached) or pyrrol-3-yl (C-attached).

The term "quaternized heterocyclic group," as used herein, should be understood as the term "heterocyclic group" with the exception that any one or more heteroatoms, such as nitrogen and phosphorus, has four substituents, whereby the heteroatoms are positively charged. Examples of quaternized heterocyclic groups include but are not limited to:

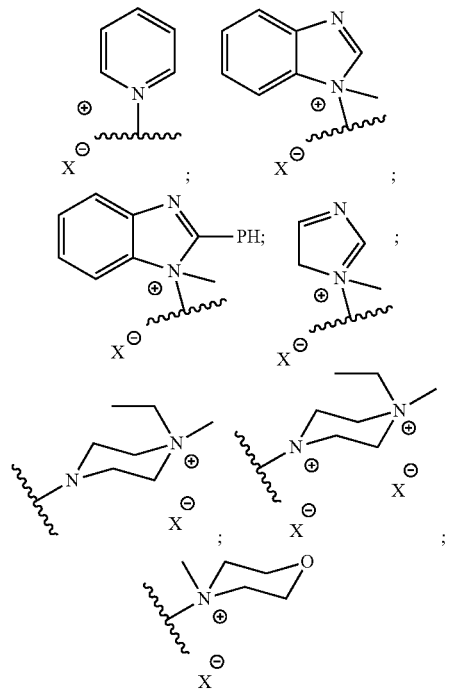

where X is an anionic ligand.

The term "halogen," as used herein, means an element selected from fluorine, chlorine, bromine, and iodine.

The term "alkyl group," as used herein, refers to a saturated, linear or branched hydrocarbon substituent of the indicated number of carbon atoms. Examples of alkyl groups include but are not limited to methyl, ethyl, propyl, iso-propyl, butyl, sec-butyl, tert-butyl, pentyl, iso-pentyl groups.

The term "alkylamino group," as used herein, should be understood as the term "alkyl group" with the exception that one or more hydrogen atoms have been substituted with a zero-order, first-order or second-order nitrogen atom. Examples of alkylamino groups include but are not limited to: —CH$_2$NMe$_2$, —CH$_2$NEt$_2$, —CH$_2$CH$_2$NMe$_2$, —CH$_2$CH$_2$NEt$_2$, —NMe$_2$, —NEt$_2$.

The term "alkylphosphine group," as used herein, should be understood as the term "alkylamino group" with the exception that a nitrogen atom has been substituted with a phosphorus atom.

The term "alkylammonium group," as used herein, should be understood as the term "alkyl group" with the exception that one or more hydrogen atoms have been substituted with a third-order nitrogen atom, whereby a nitrogen atom is positively charged. Examples of alkylammonium groups include but are not limited to:

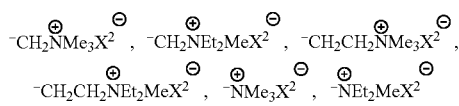

wherein X$^2$ is an anionic ligand.

The term "alkylphosphonium group," as used herein, should be understood as the term "alkylamino group" with the exception that a nitrogen atom has been substituted with a phosphorus atom.

The term "alkenyl group," as used herein, refers to a non-cyclic, linear or branched alkenyl chain of the indicated number of carbon atoms and containing at least one double carbon-carbon bond. Examples of alkenyl groups include but are not limited to vinyl, allyl, 1-butenyl, 2-butenyl, 1-hexenyl, 2-hexenyl, 3-hexenyl groups.

The term "alkynyl group," as used herein, refers to a non-cyclic, linear or branched alkynyl chain of the indicated number of carbon atoms and containing at least one triple carbon-carbon bond. Examples of alkynyl groups include but are not limited to: ethynyl, propynyl, 1-butynyl, 2-butynyl, 1-hexynyl, 2-hexynyl, 5-hexynyl groups.

The term "cycloalkyl group," as used herein, refers to a saturated mono- or polycyclic hydrocarbon substituent of the indicated number of carbon atoms. Examples of a cycloalkyl group include but are not limited to cyclopropyl, cyclobutyl, cyclopentyl, cyclohexyl, cycloheptyl, cyclooctyl groups.

The term "electron acceptor group," as used herein, refers to an organic substituent, which causes that the energy of the lowest unoccupied molecular orbital (LUMO) of the molecule substituted with such a group is lower than the LUMO energy of the unsubstituted molecule. An electron acceptor group reduces the electron density in the molecule by the inductive or resonance effect. Examples of an electron acceptor group include but are not limited to amido, aldehyde, ketone, sulfonyl, carboxyl, phenyl, I, Br, Cl, F, cyano, nitro group, aromatic group substituted with halogen atoms, aromatic group substituted with perfluorinated groups.

The term "inert ligand," as used herein, refers to an uncharged substituent, capable of coordinating with a ruthenium centre. Examples of inert ligands include but are not limited to amines, phosphines and oxides thereof, alkyl and aryl phosphites and phosphates, ethers, alkyl and aryl sulfides, alkyl and aryl halides, coordinated hydrocarbons, N-heterocyclic carbenes.

The term "anionic ligand," as used herein, refers to a substituent capable of coordinating with a metallic centre, having a charge capable of partial or complete compensation of a metallic centre charge. Examples of anionic ligands include but are not limited to fluoride, chloride, bromide, iodide, cyanide, cyanate, thiocyanate anions, anions of carboxylic acids, anions of alcohols and phenols, anions of thiols and thiophenols, anions of hydrocarbons with a delocalized charge (e.g. a cyclopentadiene anion), anions of (organo) sulfuric acids and of (organo)phosphoric acids and esters thereof (such as e.g. anions of alkylosulfonic acids and of arylosulphonic acids, anions of alkylophosphoric acids and of arylophosphoric acids, anions of alkyl and aryl esters of sulfuric acid, anions of alkyl and aryl esters of phosphoric acids, anions of alkyl and aryl esters of alkylphosphoric and arylphosphoric acids). Alternatively, an anionic ligand may have L$^1$, L$^2$ groups combined like a catechol anion, an acetylacetone anion, a salicylaldehyde anion. Anionic ligand (X, X$^1$, X$^2$) and inert ligands (L$^1$, L$^2$) may be linked together to form multidentate ligands, for example, bidentate ligand (XX$^1$), tridentate ligand (XX$^1$L$^1$), tetradentate ligand (XX$^1$L$^1$L$^2$), bidentate ligand (X$^1$L$^1$), tridentate ligand (X$^1$L$^1$L$^2$), bidentate ligand (L$^1$L$^2$). Examples of such ligands include but are not limited to a catechol anion, an acetylacetone anion, a salicylaldehyde anion.

The term "carbene," as used herein, means a particle containing an inert carbon atom of valency number being two and two unpaired valence electrons. The term "carbene" covers also carbene analogs in which a carbon atom is substituted with another chemical element; examples of such elements include but are not limited to boron, silicon, germanium, tin, lead, nitrogen, phosphorus, sulfur, selenium and tellurium.

The term "onium group," as used herein, refers to aliphatic, aromatic and heterocyclic quaternary ammonium, phosphonium or sulphonium group.

Intermediates in the synthesis of new complexes of formula 1 are alkoxystyrene derivatives of formula 2:

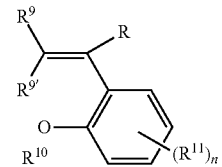

wherein R$^{10}$ is —C$_{1-20}$ alkyl, —C$_{3-8}$ cycloalkyl, —C$_{2-20}$ alkenyl, —C$_{2-20}$ alkynyl, —C$_{5-10}$ aryl, —C$_{1-20}$ alkoxy, —C$_{2-20}$ alkenyloxy, —C$_{2-20}$ alkynyloxy, —C$_{5-10}$ aryloxy, —C$_{1-20}$ alkoxy carbonyl, —C$_{1-20}$ alkylamino, amino, —C$_{1-20}$ alkylphosphine, —C$_{1-20}$ alkylthiol, —C$_{1-20}$ alkylsulfunyl, —C$_{1-20}$ alkylsulfinyl, —CH$_2$C(=O)—R, —CH$_2$C(=O)—O—R, —CH$_2$C(=O)NR$_2$, —CH$_2$C(=O)—N—R—O—R, —C$_{4-10}$ heterocyclic group, optionally substituted with —C$_{1-20}$ alkyl, —C$_{5-10}$ aryl or —C$_{4-10}$ heterocyclic group; and the remaining substituents are as defined above.

Compounds of formula 2 can be obtained from compounds of formula 3, wherein R$^{11}$ is as defined above, by reacting with an alkylating reagent R$^{10}$Z, wherein R$^{10}$ is as defined above, Z is an iodine or bromine atom, to give compound 4.

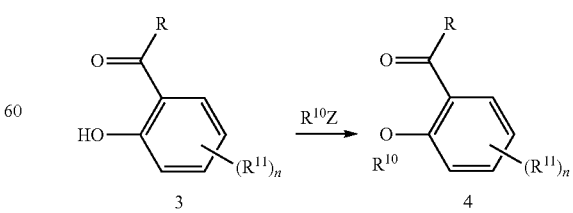

The substituted compound of formula 4, containing a carbonyl group then reacts with an olefinating reagent of formula $R^9(R^{9'})=W$, wherein $R^9$, $R^{9'}$ is as defined above, W is a leaving group suitable for an olefination reaction, to give a compound of formula 2.

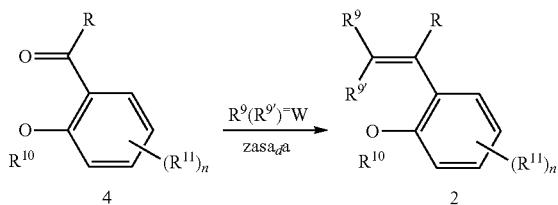

In another reaction, the substituted phenol 5 reacts with a compound of formula $R^{10}OH$ in the presence of triphenylphosphine and diisopropyl azodicarboxylate (DIAD) to give a compound of formula 2.

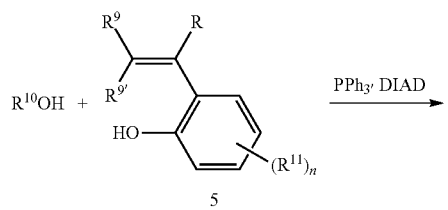

Precursors of N-heterocyclic carbene ligands, which are used in the synthesis of complexes of formula 1, are compounds of formula 6

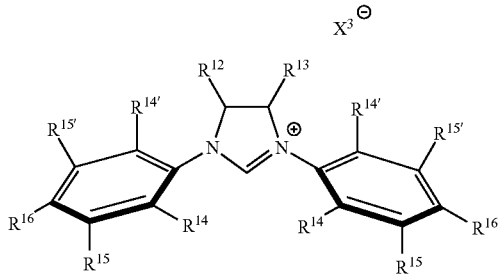

wherein all substituents are as defined above, and $X^3$ is a chlorine atom or a $BF_4$ group.

Compounds of formula 6 can be obtained from an intermediate of formula 7a, which in turn is obtained by the addition of bromine to alkene of formula 7. A compound of formula 7a is heated in the presence of an excess of an aromatic amine to give a compound of formula 8. Compounds of formula 7a and 8 may be carried out into the appropriate hydrochlorides, which facilitates their isolation and purification.

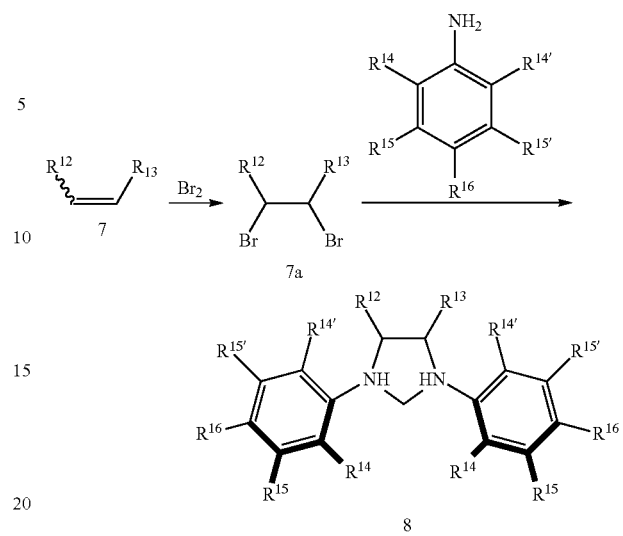

wherein $R^{12}$, $R^{13}$, $R^{14}$, $R^{14'}$, $R^{15}$, $R^{15'}$ and $R^{16}$ have the meaning as defined above.

A compound of formula 8 is then heated in triethyl orthoformate in the presence of $NH_4X^3$, giving a precursor of a N-heterocyclic carbene ligand of formula 6, directly or by exchange of a counterion $X^3$.

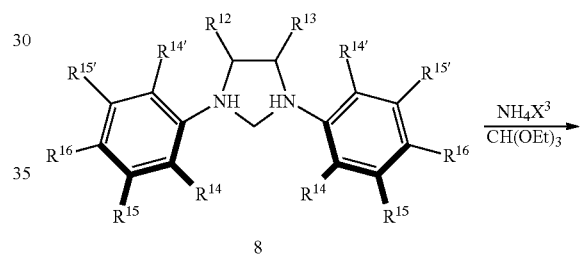

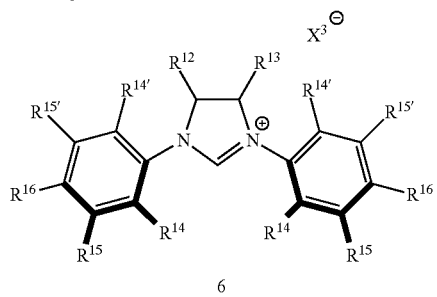

A compound of formula 6 in a reaction with an appropriate base (such as potassium tert-amylate) gives N-heterocyclic carbene of formula 9.

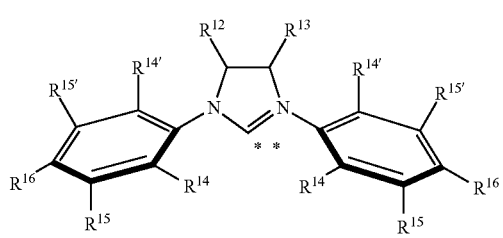

A compound of formula 9 may react in situ with a complex of formula 10 (which is a (pre)catalyst of the first generation), where all substituents are as defined above, giving a complex of formula 11, wherein the substituents are as defined above.

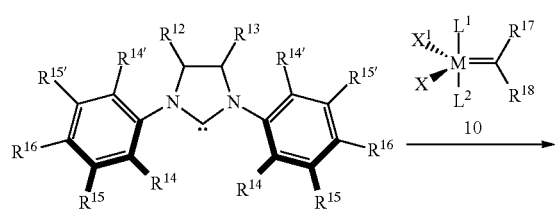
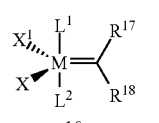
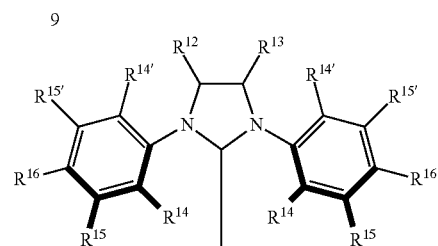
A compound of formula 9 may also react in situ with a complex of formula 12, wherein the substituents are as defined above, giving a compound of formula 13.
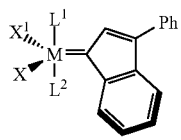
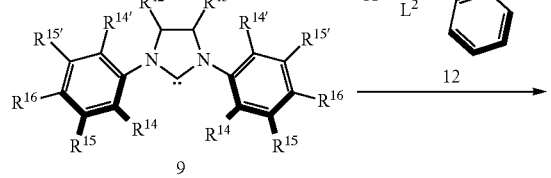
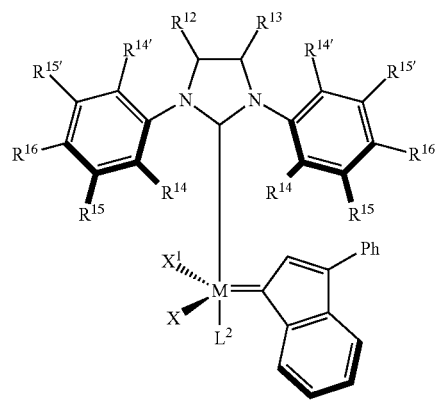
Complexes of formulae 11 and 13 in a reaction with a compound of formula 2 give a complex of formula 14, where the ligands are as defined above.
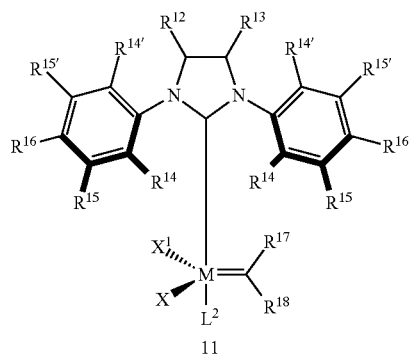 or 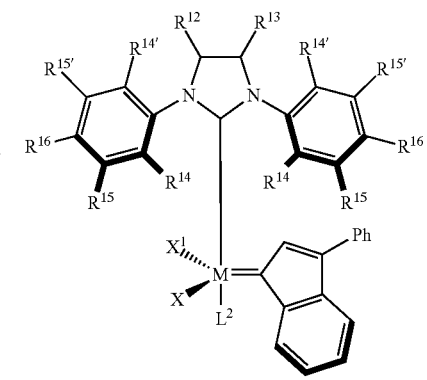
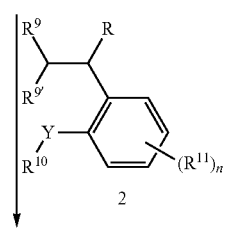

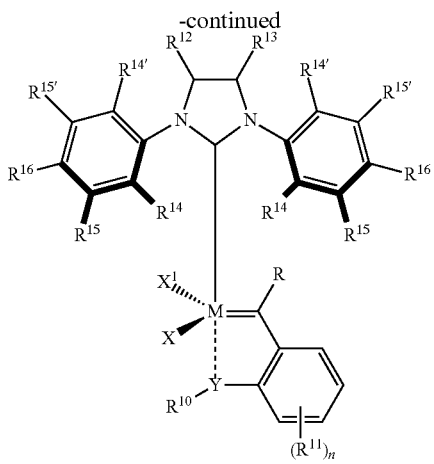

14

A complex of formula 14 can be subjected to a reaction with an alkylating reagent of formula $R^8X^2$ thus giving a complex of formula 1. The thus obtained complex of formula 1 may be optionally subjected to a reaction with a reagent of formula $R^{8'}X^{2'}$.

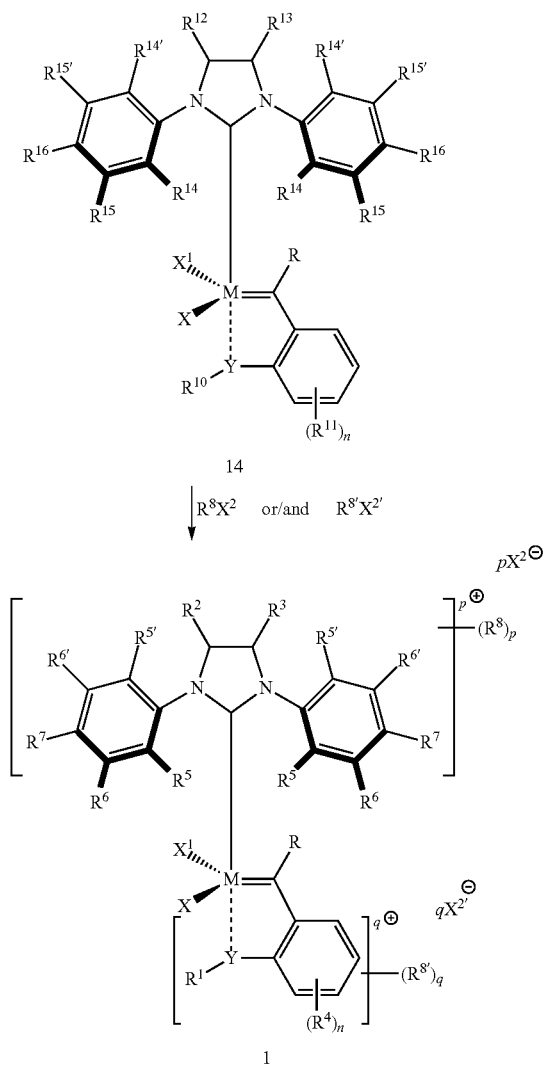

Precursors of N-heterocyclic carbene ligands of formula 6 are characterized by the fact that complexes 10, 12 and 14 can be obtained from them which easily undergo a quaternization reaction giving complexes of formulae 15, 17 and 1, respectively.

Complexes of formulae 1, 15 and 17 containing a quaternary onium group in an inert ligand were not so far obtained by the reaction of an appropriate complex with an alkylating reagent. This method allows to obtain the products in a simple, efficient and cost-effective way. For example, the catalysts obtained by R. H. Grubbs were purified by a three-fold column chromatography under anaerobic conditions, and one of the ligands was obtained using an expensive ion-exchange resin (J. P. Jordan, R. H. Grubbs; Angew. Chem. Int. Ed., 2007, 46, 5152-5155).

The complexes are highly efficient and effective (pre)catalysts for an olefin metathesis reaction and possess the physico-chemical properties which are desirable from the point of view of the purification of products of the metathesis reaction. In the metathesis reaction there is a contact between the complexes and the substrates under conditions appropriate for this type of reaction. Complexes are used in a ring closing metathesis (RCM), cross metathesis (CM), alkene-alkyne (en-yn) reaction, homometathesis (which is a kind of a cross metathesis) and a ring opening metathesis polymerization (ROMP).

The term "desirable physico-chemical properties" means that the complexes have a high affinity to an adsorbent (in particular, acidic silica gel and alumina) and exhibit good (and in some cases excellent) solubility in pure water. Metathesis reaction conditions for the complexes are comparable to those used for the complexes known in the prior art. The metathesis reaction is normally carried out with an amount of a (pre)catalyst ranging from 0.2 to 5 mol %, at a temperature from 0° C. to 120° C., within the period from 0.1 to 96 hours.

Olefin metathesis reaction products obtained with the use of the complexes contain a very small amount of heavy metal (typically less than 10 ppm), while their purification process is simple, fast and cheap. The simplicity and effectiveness of heavy metal removal from the postreaction mixture is extremely important from the point of view of the application of metathesis technology in the pharmaceutical industry. The complexes are also highly active and effective in an olefin metathesis reaction carried out in pure water, and what, such reactions can be carried out in the presence of oxygen.

The following embodiments are specifically contemplated herein:

A method of synthesis of a product complex, comprising:
subjecting a precursor complex to reaction with an alkylating agent;
wherein the product complex has a structure of formula 15

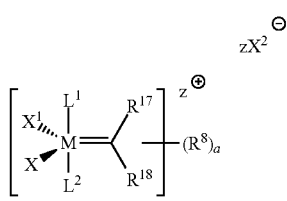

in which $L^{1'}$ and $L^{2'}$ are, independently, inert ligands, wherein at least one of $L^{1'}$ and $L^{2'}$ comprises a quaternary ammonium group or a phosphonium group; and M is ruthenium or osmium; and X, $X^1$, and each $X^2$ are, independently, anionic ligands; and $R^8$ is optionally substituted —$C_{1-20}$ alkyl, optionally substituted —$C_{3-8}$ cycloalkyl, optionally substituted —$C_{2-20}$ alkenyl, or optionally substituted —$C_{2-20}$ alkynyl, wherein each substituent is independently a halogen atom, —$C_{5-10}$ aryl, —C(=O)—$C_{1-6}$ alkyl, —C(=O)—O—$C_{1-6}$ alkyl, —C(=O)—N($C_{1-6}$ alkyl)$_2$, —C(=O)—N—($C_{1-6}$ alkyl)-O—$C_{1-6}$ alkyl, —C(=O)—$C_{5-10}$ aryl, —C(=O)—O—$C_{5-10}$aryl, —C(=O)—N($C_{5-10}$ aryl)$_2$, or —C(=O)—N—($C_{5-10}$ aryl)-O—$C_{5-10}$ aryl; and $R^{17'}$ is H, optionally substituted —$C_{1-20}$ alkyl, optionally substituted —$C_{2-20}$ alkenyl, optionally substituted —$C_{2-20}$ alkynyl, or optionally substituted —$C_{5-10}$ aryl;

$R^{18'}$ is optionally substituted phenyl, optionally substituted vinyl, or optionally substituted —C=C(CH$_3$)$_2$;

$R^{17'}$ and $R^{18'}$ may be optionally linked together to form a cyclic or polycyclic system that is aliphatic or aromatic; or $R^{17'}$ and $R^{18'}$, together with the carbon atom connecting them, can optionally be a 3-phenyl-1H-indene-1-ylide substituent; or $R^{17'}$, $R^{18'}$ or both $R^{17'}$ and $R^{18'}$ may be optionally linked to $L^1$ or $L^2$ to form a bidentate ligand;

a is 1, 2, 3, 4, 5, 6 or 7;

z is 1, 2, 3, 4, 5, 6 or 7;

wherein the precursor complex has a structure of formula 10

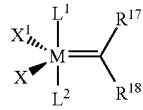

in which M, X, $X^1$ have the same meaning as in formula 15;

$L^1$ and $L^2$ are independently inert ligands, wherein at least one of $L^1$ and $L^2$ comprises an $X^2$ group, an alkylamino group, or an alkylphosphine group; and $R^{17}$ is H, optionally substituted —$C_{1-20}$ alkyl, optionally substituted —$C_{2-20}$ alkenyl, optionally substituted —$C_{2-20}$ alkynyl, or optionally substituted —$C_{5-10}$ aryl; and $R^{18}$ is optionally substituted phenyl, optionally substituted vinyl, or optionally substituted —C=C(CH$_3$)$_2$; or $R^{17}$ and $R^{18}$ may be optionally linked together to form a cyclic or polycyclic system that is aliphatic or aromatic; or $R^{17}$, $R^{18}$, or both $R^{17}$ and $R^{18}$ may be optionally linked to $L^1$ or $L^2$ to form a bidentate ligand; or $R^{17}$ and $R^{18}$, together with the carbon atom connecting them, can optionally be a 3-phenyl-1H-indene-1-ylide substituent;

wherein the alkylating reagent has a formula $R^8X^2$, wherein $R^8$ is optionally substituted —$C_{1-20}$ alkyl, optionally substituted —$C_{3-8}$ cycloalkyl, optionally substituted —$C_{2-20}$ alkenyl, optionally substituted —$C_{2-20}$ alkynyl group; wherein each substituent is independently a halogen atom, —$C_{5-10}$ aryl, —C(=O)—$C_{1-6}$ alkyl, —C(=O)—O—$C_{1-6}$ alkyl, —C(=O)—N($C_{1-6}$ alkyl)$_2$, —C(=O)—N—($C_{1-6}$ alkyl)-O—$C_{1-6}$ alkyl, —C(=O)—$C_{5-10}$ aryl, —C(=O)—O—$C_{5-10}$aryl, —C(=O)—N($C_{5-10}$ aryl)$_2$, or —C(=O)—N—($C_{5-10}$ aryl)-O—$C_{5-10}$ aryl;

$X^2$ is an anionic ligand.

A method of synthesis of complexes of formula 17

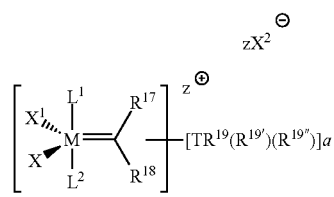

wherein $L^{1'}$ are $L^{2'}$ are, independently, an inert ligand, wherein at least one of $L^{1'}$ and $L^{2'}$ comprises a quaternary ammonium or a phosphonium group; and M is ruthenium or osmium; and X, $X^1$, and each $X^2$ are, independently, an anionic ligand; and $R^{17'}$ is H, optionally substituted —$C_{1-20}$ alkyl, optionally substituted —$C_{2-20}$ alkenyl, optionally substituted —$C_{2-20}$ alkynyl, or optionally substituted —$C_{5-10}$ aryl; and $R^{18'}$ is optionally substituted phenyl, optionally substituted vinyl, or optionally substituted —C=C(CH$_3$)$_2$; or $R^{17'}$ and $R^{18'}$ may be optionally linked together to form a cyclic or polycyclic system that is aliphatic or aromatic;

$R^{17'}$ and $R^{18'}$, together with a carbon atom connecting them, can optionally be a 3-phenyl-1H-indene-1-ylide substituent; or $R^{17'}$, $R^{18'}$, or both $R^{17'}$ and $R^{18'}$ may be optionally linked to $L^1$ or $L^2$ to form a bidentate ligand;

a is 1, 2, 3, 4, 5, 6 or 7;

z is 1, 2, 3, 4, 5, 6 or 7;

T is N or P;

$R^{19}$, $R^{19'}$, $R^{19''}$ are, independently, H, —$C_{1-6}$ alkyl, —$C_{5-10}$ aryl, or a $C_{4-10}$ heterocyclic group; and $X^2$ comes from complex 10;

wherein the method comprises subjecting a complex of formula 10 to reaction with a compound having a formula $TR^9(R^{19'})(R^{19''})$;

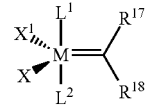

wherein M, X, $X^1$ have the same meaning as in compound 17;

$L^1$ and $L^2$ are independently inert ligands, wherein at least one of $L^1$ and $L^2$ comprises an $X^2$ group, an alkylamino group, or an alkylphosphine group; and $R^{17}$ is H, optionally substituted —$C_{1-20}$ alkyl, optionally substituted —$C_{2-20}$ alkenyl, optionally substituted —$C_{2-20}$ alkynyl, or optionally substituted —$C_{5-10}$ aryl; and $R^{18}$ is optionally substituted phenyl, optionally substituted vinyl, or optionally substituted —C=C(CH$_3$)$_2$; or $R^{17}$ and $R^{18}$ may be optionally linked together to form a cyclic or polycyclic system that is aliphatic or aromatic; or $R^{17}$, $R^{18}$, or both $R^{17}$ and $R^{18}$ may be optionally linked to $L^1$ or $L^2$ to form a bidentate ligand; or $R^{17}$ and $R^{18}$, together with the carbon atom connecting them, can optionally be a 3-phenyl-1H-indene-1-ylide substituent;

A method according to embodiment 1 or 2, wherein $L^1$ is a complex of general formula 9 is defined by formula

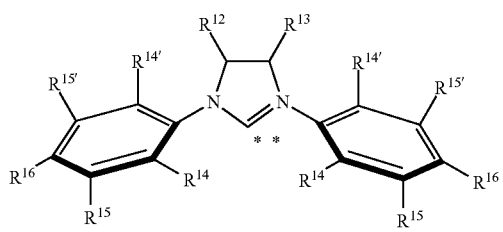

9 wherein $R^{12}$, $R^{13}$, each $R^{14}$, each $R^{14'}$, each $R^{15}$, each $R^{15'}$, and each $R^{16}$ are, independently, H, optionally substituted —C$_{1-6}$ alkyl, optionally substituted —C$_{1-6}$ haloalkyl, optionally substituted —C$_{5-10}$ aryl, optionally substituted —C$_{1-6}$ alkylamino, optionally substituted —C$_{1-6}$ alkylphosphine, or an optionally substituted —C$_{4-10}$ heterocyclic group, wherein each substituent is independently —C$_{1-6}$ alkyl, —C$_{1-6}$ alkylamino or a —C$_{4-10}$ heterocyclic group; and $R^{12}$ and $R^{13}$, $R^{14}$ and $R^{15}$, and $R^{14'}$ and $R^{15'}$ may be optionally linked together to form a substituted or unsubstituted, fused —C$_{4-8}$ carbocyclic ring, or a substituted or unsubstituted, fused aromatic ring; and $L^2$ is an inert ligand, wherein group 9 or $L^2$ contains at least one $X^2$ group, alkylamino group, or alkylphosphine group.

A method according to embodiment 3, wherein a complex of general formula 10 is defined by general formula 14

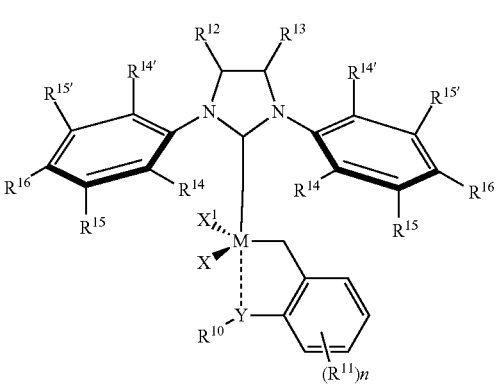

14 wherein M is ruthenium or osmium;
X and $X^1$ are, independently, inert ligands;
Y is O, S, N or P;
R is H, —C$_{1-20}$ alkyl, —C$_{2-20}$ alkenyl, —C$_{2-20}$ alkynyl, or —C$_{3-10}$ aryl;
$R^{10}$ is optionally substituted —C$_{1-20}$ alkyl, optionally substituted —C$_{5-10}$ aryl, optionally substituted —C$_{1-20}$ alkoxy, optionally substituted —C$_{5-10}$ aryloxy, optionally substituted —C$_{1-20}$ alkylamino, optionally substituted —C$_{1-20}$ protonated alkylamino, optionally substituted —C$_{1-20}$ alkylammonium, optionally substituted —C$_{1-12}$ alkylthiol, optionally substituted —CH$_2$C(=O)—C$_{1-6}$ alkyl, optionally substituted —CH$_2$C(=O)—O—C$_{1-6}$ alkyl, optionally substituted —CH$_2$C(=O)—N(C$_{1-6}$ alkyl)$_2$, optionally substituted —CH$_2$C(=O)—N—(C$_{1-6}$ alkyl)-O—C$_{1-6}$ alkyl, optionally substituted —CH$_2$C(=O)—C$_{5-10}$ aryl, optionally substituted —CH$_2$C(=O)—O—C$_{5-10}$ aryl, optionally substituted —CH$_2$C(=O)—N(C$_{5-10}$ aryl)$_2$, optionally substituted —CH$_2$C(=O)—N—(C$_{5-10}$ aryl)-O—C$_{5-10}$ aryl, optionally substituted —C$_{1-20}$ alkylphosphine, optionally substituted —C$_{1-20}$ alkylphosphonium, optionally substituted —C$_{4-10}$ heterocyclic, or an optionally substituted —C$_{4-10}$ quaternized heterocyclic group, wherein each substituent is independently —C$_{1-20}$ alkyl, —C$_{5-10}$ aryl or a —C$_{4-10}$ heterocyclic group;

$R^{11}$ is halogen, optionally substituted —C$_{1-20}$ alkyl, optionally substituted —C$_{1-20}$ haloalkyl, optionally substituted —C$_{2-20}$ alkenyl, optionally substituted —C$_{2-20}$ alkynyl, optionally substituted —C$_{5-10}$ aryl, optionally substituted —C$_{1-20}$ alkoxy, optionally substituted —C$_{2-20}$ alkenyloxy, optionally substituted —C$_{2-20}$ alkynyloxy, optionally substituted —C$_{5-10}$ aryloxy, optionally substituted —C$_{1-20}$ alkoxy carbonyl, optionally substituted —C$_{1-20}$-alkylamino, optionally substituted —C$_{1-20}$ protonated alkylamino, optionally substituted —C$_{1-20}$ alkylammonium, optionally substituted amino, optionally substituted protonated amino, optionally substituted —C$_{4-10}$ heterocyclic, optionally substituted —C$_{4-10}$ quaternized heterocyclic, optionally substituted —C$_{1-20}$ alkylphosphino, optionally substituted —C$_{1-20}$ alkylphosphonium, optionally substituted —C$_{1-20}$ alkylthiol, nitro, carboxyl, optionally substituted amido, optionally substituted sulfonamido, or optionally substituted —C$_{1-20}$ perhaloalkyl, wherein each substituent is independently —C$_{1-20}$ alkyl, —C$_{1-20}$ haloalkyl, —C$_{1-20}$ perhaloalkyl, —C$_{5-10}$ aryl, or a —C$_{4-10}$ heterocyclic group;

n is 0, 1, 2, 3, or 4;

$R^{12}$, $R^{13}$, $R^{14}$, $R^{14'}$, $R^{15}$, $R^{15'}$, $R^{16}$ are, independently, H, optionally substituted —C$_{1-6}$ alkyl, optionally substituted —C$_{1-6}$ haloalkyl, optionally substituted —C$_{5-10}$ aryl, optionally substituted —C$_{1-6}$ alkylamino, optionally substituted —C$_{1-6}$ alkylphosphino, -optionally substituted C$_{4-10}$ heterocyclic group, wherein each substituent is independently —C$_{1-6}$ alkyl, —C$_{1-6}$ alkylamino or a —C$_{4-10}$ heterocyclic group;

$R^{12}$ and $R^{13}$, $R^{14}$ and $R^{15}$, and $R^{14'}$ and $R^{15'}$ may be optionally linked together to form a substituted or unsubstituted, fused —C$_{4-8}$ carbocyclic ring, or a substituted or unsubstituted, fused aromatic ring;

and a complex of general formula 15 is defined by general formula 1

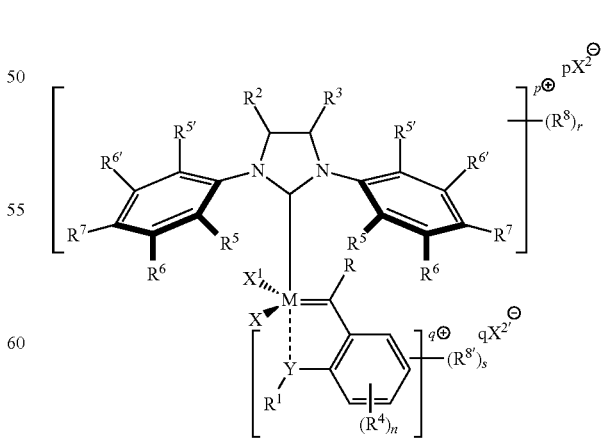

1 wherein M is ruthenium or osmium;
X, $X^1$, $X^2$ and $X^{2'}$ are, independently, inert ligands;
Y is O, S, N, or P;

R is H, —$C_{1-20}$ alkyl, —$C_{2-20}$ alkenyl, —$C_{2-20}$ alkynyl, or —$C_{5-10}$ aryl;

$R^1$ is optionally substituted —$C_{1-20}$ alkyl, optionally substituted $C_{3-8}$ cycloalkyl, optionally substituted —$C_{2-20}$ alkenyl, optionally substituted —$C_{2-20}$ alkynyl, optionally substituted —$C_{5-10}$ aryl, optionally substituted —$C_{1-20}$ alkoxy, optionally substituted —$C_{2-20}$ alkenyloxy, optionally substituted —$C_{2-20}$ alkynyloxy, optionally substituted —$C_{5-10}$ aryloxy, optionally substituted —$C_{1-20}$ alkoxycarbonyl, optionally substituted —$C_{1-20}$ alkylamino, optionally substituted —$C_{1-20}$ alkylphosphino, -optionally substituted $C_{1-20}$ alkylthiol, optionally substituted —$C_{1-20}$ alkylammonium, optionally substituted —$C_{1-20}$ alkylphosphonium, optionally substituted —$C_{1-20}$ alkylsulfonyl, optionally substituted —$C_{1-20}$ alkylosulfinyl, optionally substituted —$CH_2C(=O)$—$C_{1-6}$ alkyl, optionally substituted —$CH_2C(=O)$—O—$C_{1-6}$ alkyl, optionally substituted —$CH_2C(=O)$—N($C_{1-6}$ alkyl)$_2$, optionally substituted —$CH_2C(=O)$—N—($C_{1-6}$ alkyl)-O—$C_{1-6}$ alkyl, optionally substituted —$CH_2C(=O)$—$C_{5-10}$ aryl, optionally substituted —$CH_2C(=O)O$—$C_{5-10}$ aryl, optionally substituted —$CH_2C(=O)$—N($C_{5-10}$ aryl)$_2$, optionally substituted —$CH_2C(=O)$—N—($C_{5-10}$ aryl)-O—$C_{5-10}$ aryl, optionally substituted —$C_{4-10}$ heterocyclic, or optionally substituted —$C_{4-10}$ quaternized heterocyclic, wherein each substituent is independently —$C_{1-20}$ alkyl, —$C_{5-10}$ aryl, or a —$C_{4-10}$ heterocyclic group;

$R^1$ may be optionally linked to X or $X^1$ to form a tridentate ligand;

$R^2$ and $R^3$ are, independently, H, optionally substituted —$C_{1-6}$ alkyl, optionally substituted —$C_{3-8}$ cycloalkyl, optionally substituted —$C_{5-10}$ aryl, optionally substituted —$C_{1-20}$ alkylamino, optionally substituted —$C_{1-20}$ alkylphosphino, optionally substituted —$C_{1-20}$ alkylammonium, or optionally substituted —$C_{1-20}$ alkylphosphonium, wherein each substituent is independently: —$C_{5-10}$ aryl, —$C_{4-10}$ heterocyclic, or a —$C_{4-10}$ quaternized heterocyclic group, which in turn may be substituted with at least one: nitro, —$C_{1-6}$ alkyl, —$C_{1-6}$ alkoxy, —$C_{5-10}$ aryl group or halogen;

$R^2$ and $R^3$ may be optionally linked together to form a substituted or unsubstituted, fused —$C_{4-8}$ carbocyclic ring, or a substituted or unsubstituted, fused aromatic ring;

$R^4$ is halogen, optionally substituted —$C_{1-20}$ alkyl, optionally substituted —$C_{2-20}$ alkenyl, optionally substituted —$C_{2-20}$ alkynyl, optionally substituted —$C_{5-10}$ aryl, optionally substituted —$C_{1-20}$ alkoxy, optionally substituted —$C_{5-20}$ alkenyloxy, optionally substituted —$C_{2-20}$ alkynyloxy, optionally substituted —$C_{5-10}$ aryloxy, optionally substituted —$C_{1-20}$ alkoxy carbonyl, optionally substituted —$C_{1-20}$ alkylamino, optionally substituted —$C_{1-20}$ protonated alkylamino, optionally substituted amino, optionally substituted protonated amino, optionally substituted —$C_{1-20}$ alkylphosphino, optionally substituted —$C_{1-20}$ alkylthiol, optionally substituted —$C_{1-20}$ alkylammonium, optionally substituted —$C_{1-20}$ alkylphosphonium, optionally substituted —$C_{4-10}$ quaternized heterocyclic, nitro, carboxyl, optionally substituted amido, optionally substituted sulfonamido, or optionally substituted —$C_{1-20}$ perhaloalkyl; wherein each substituent is independently —$C_{1-20}$ alkyl, —$C_{1-20}$ perhaloalkyl, —$C_{5-10}$ aryl, or a —$C_{4-10}$ quaternized heterocyclic group;

n is 0, 1, 2, 3, or 4;

$R^5$, $R^{5'}$, $R^6$, $R^{6'}$, and $R^7$ are, independently, H, optionally substituted —$C_{1-6}$ alkyl, optionally substituted —$C_{1-20}$ alkylamino, optionally substituted —$C_{1-20}$ alkylphosphino, optionally substituted —$C_{1-20}$ alkylammonium, optionally substituted —$C_{1-20}$ alkylphosphonium, optionally substituted —$C_{4-10}$ heterocyclic, optionally substituted —$C_{4-10}$ quaternized heterocyclic group, wherein each substituent is independently a —$C_{4-10}$ quaternized heterocyclic, —$C_{1-6}$ alkyl, or —$C_{5-10}$ aryl, which in turn may be substituted with nitro, —$C_{1-6}$ alkyl, —$C_{1-6}$ alkoxy, —$C_{5-10}$ aryl group or halogen;

$R^5$ and $R^6$, and $R^{5'}$ and $R^{6'}$ may be optionally linked together to form a substituted or unsubstituted, fused —$C_{4-8}$ carbocyclic ring, or a substituted or unsubstituted, fused aromatic ring;

$R^8$ is optionally substituted —$C_{1-20}$ alkyl, optionally substituted —$C_{3-8}$ cycloalkyl, optionally substituted —$C_{2-20}$ alkenyl, or optionally substituted —$C_{2-20}$ alkynyl; wherein each substituent is independently a halogen atom, —$C_{5-10}$ aryl, —$C(=O)$—$C_{1-6}$ alkyl, —$C(=O)$—O—$C_{1-6}$ alkyl, —$C(=O)$—N($C_{1-6}$ alkyl)$_2$, —$C(=O)$—N—($C_{1-6}$ alkyl)-O—$C_{1-6}$ alkyl, —$C(=O)$—$C_{5-10}$ aryl, —$C(=O)$—O—$C_{5-10}$aryl, —$C(=O)$—N($C_{5-10}$ aryl)$_2$, or —$C(=O)$—N—($C_{5-10}$ aryl)-O—$C_{5-10}$ aryl;

p is 1, 2, 3, 4, or 5;

r is 0, 1, 2, or 3;

$R^{8'}$ is H, —$C_{1-20}$ alkyl, $C_{3-8}$ cycloalkyl, —$C_{2-20}$ alkenyl, or —$C_{2-20}$ alkynyl;

q is 0, 1, 2 or 3;

s is 0, 1, 2, or 3;

wherein at least one substituent among $R^2$, $R^3$, $R^5$, $R^{5'}$, $R^6$, $R^{6'}$, and $R^7$ contains a quaternary onium group;

and the complex obtained in this manner may be optionally subjected to a further reaction with a compound of formula $R^{8'}X^{2'}$, giving a different complex of formula 1, wherein $R^{8'}$ and $X^{2'}$ are as defined above.

A method according to embodiment 4, wherein, in formula 14

M is a ruthenium;

X and $X^1$ are an inert ligand;

Y is O;

$R^{10}$ is optionally substituted —$C_{1-12}$ alkyl, optionally substituted —$C_{1-12}$ haloalkyl, optionally substituted —$C_{5-10}$ aryl, optionally substituted —$C_{1-12}$ alkoxy, optionally substituted —$C_{5-10}$ aryloxy, optionally substituted —$C_{1-12}$ alkoxy carbonyl, optionally substituted —$C_{1-12}$ alkylamino, an optionally substituted —$C_{4-10}$ heterocyclic group, wherein each substituent is independently —$C_{1-12}$ alkyl, —$C_{5-10}$ aryl or a —$C_{4-10}$ heterocyclic group;

$R^{11}$ is halogen, optionally substituted —$C_{1-12}$ alkyl, optionally substituted —$C_{1-12}$ haloalkyl, optionally substituted aryl, optionally substituted —$C_{1-12}$ alkoxy, optionally substituted —$C_{5-10}$ aryloxy, optionally substituted —$C_{1-12}$ alkoxy carbonyl, optionally substituted —$C_{1-12}$ alkylamino, amino, optionally substituted —$C_{1-12}$ alkylphosphino, optionally substituted —$C_{4-10}$ heterocyclic, nitro, carboxyl, optionally substituted amido, optionally substituted sulfonamido group; wherein each substituent is independently —$C_{1-12}$ alkyl, —$C_{1-12}$ haloalkyl, —$C_{1-12}$ perhaloalkyl, —$C_{5-10}$ aryl, or a —$C_{4-10}$ heterocyclic group;

n is 0, 1 or 2; and $R^{12}$, $R^{13}$, $R^{14}$, $R^{14'}$, $R^{15}$, $R^{15'}$, $R^{16}$ are, independently, H, optionally substituted —$C_{1-6}$ alkyl, optionally substituted —$C_{1-6}$ haloalkyl, optionally substituted —$C_{5-10}$ aryl, optionally substituted —$C_{1-6}$ alkylamino, optionally substituted —$C_{1-6}$ alkylphosphino, optionally substituted —$C_{4-10}$ heterocyclic group, each optionally substituted with —$C_{1-6}$ alkyl or —$C_{4-10}$ heterocyclic group; and $R^{12}$ and $R^{13}$, $R^{14}$ and $R^{15}$, and $R^{14'}$ and $R^{15'}$ may be optionally linked together to form a substituted or unsubstituted, fused —$C_{4-8}$ carbocyclic ring, or a substituted or unsubstituted, fused aromatic ring.

A method according to embodiment 5, wherein in formula 14

M is ruthenium;

X and $X^1$ are independently Cl, Br or I;

R is H;

$R^{10}$ is an iso-propyl group or a 1-methyl-4-piperidinyl group; $R^{11}$ is a nitro or a —$NMe_2$ group; and n is 0 or 1;

A method according to embodiment 6, wherein a compound of formula 14 is obtained by reacting a compound of formula 11

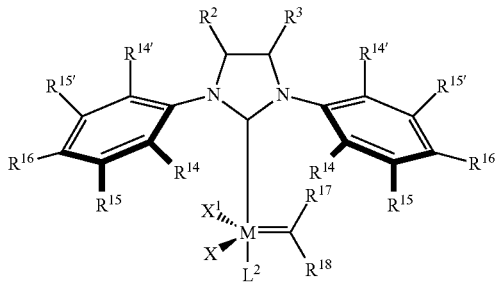

wherein all X, $X^1$, $L^2$, $R^{12}$, $R^{13}$, each $R^{14}$, each $R^{14'}$, each $R^{15}$, each $R^{15'}$, each $R^{16}$, $R^{17}$, and $R^{18}$ are as defined above, with an intermediate of formula 2a or 2b,

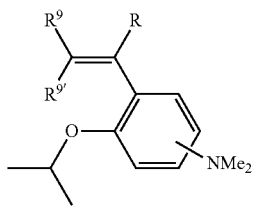

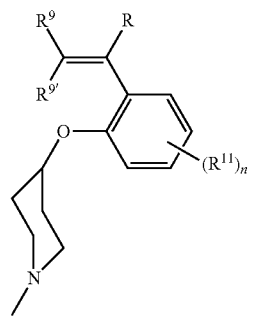

wherein R is H;

$R^9$ and $R^{9'}$ are a methyl or ethyl group;

$R^{11}$ is an electron acceptor group; and n is 0 or 1;

A method according to any one of embodiments 3-6, wherein, in formula 9, substituents $R^{12}$, $R^{13}$ are, independently, H, —$CH_2NMe_2$ group or

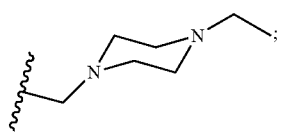 [SMILES: *CN1CCN(CC)CC1]

$R^{14}$ and $R^{14'}$ are a methyl or iso-propyl group;
$R^{15}$ and $R^{15'}$ are H; and
$R^{16}$ is H, a methyl group or

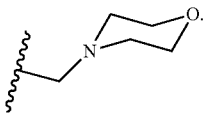 [SMILES: *CN1CCOCC1]

A method according to any one of embodiments 1-8, wherein the reaction is carried out in $R^8X^2$ as a solvent.

A method according to embodiment 9, wherein $R^8X^2$ is $CH_3Cl$, $CH_3I$, $CH_3Br$, $(CH_3)_2SO_4$.

A method according to one of embodiments 1-8, wherein the reaction is carried out in an organic solvent comprising methanol, ethanol, ethyl acetate, iso-propanol, tert-butanol, sec-butanol, diethyl ether, n-propyl ether, diisopropyl ether, tert-butyl-methyl ether, cyclopentyl-metyl ether, 1,2-dioxane, 1,3dioxane, 1,4-dioxane, dimethylformamide, tetrahydrofurane, dichloromethane, dichloroethane, trichloromethane, tetrachloromethane, tetrachloroethane, pentane, hexane, heptane, benzene, toluene, xylene, or any mixture thereof.

A method according to embodiment 11, wherein the solvent is methanol, ethanol, dichloromethane, ethyl acetate, or any mixture thereof.

A method according to any one of embodiments 2-12, wherein $TR^{19}(R^{19'})(R^{19''})$ is trimethylamine.

A method according to any one of embodiments 1-13, wherein the reaction is carried out at a temperature in the range from 0° C. to 120° C.

A method according to embodiment 14, wherein the reaction is carried out at a temperature in the range from 20° C. to 80° C.

A method according to one of embodiments 1-15, wherein the reaction is carried out in within the period from 0.1 hour to 96 hours.

A method according to embodiment 16, wherein the reaction is carried out in within the period from 1 hour to 72 hours.

A method according to any one of embodiments 1-17, wherein the reaction is carried out under atmospheric pressure.

A method according to any one of embodiments 1-17, wherein the reaction is carried out under elevated pressure.

A complex of general formula 1

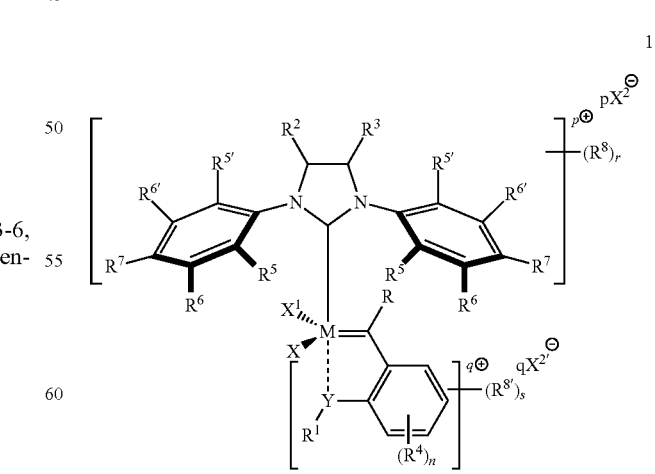

wherein M is ruthenium or osmium;
X, $X^1$, $X^2$ and $X^{2'}$ are, independently, inert ligands;
Y is O, S, N, or P;

R is H, —$C_{1-20}$ alkyl, —$C_{2-20}$ alkenyl, —$C_{2-20}$ alkynyl, or —$C_{5-10}$ aryl;

$R^1$ is optionally substituted —$C_{1-20}$ alkyl, optionally substituted $C_{3-8}$ cycloalkyl, optionally substituted —$C_{2-20}$ alkenyl, optionally substituted —$C_{2-20}$ alkynyl, optionally substituted —$C_{5-10}$ aryl, optionally substituted —$C_{1-20}$ alkoxy, optionally substituted —$C_{2-20}$ alkenyloxy, optionally substituted —$C_{2-20}$ alkynyloxy, optionally substituted —$C_{5-10}$ aryloxy, optionally substituted —$C_{1-20}$ alkoxycarbonyl, optionally substituted —$C_{1-20}$ alkylamino, optionally substituted —$C_{1-20}$ alkylphosphino, -optionally substituted $C_{1-20}$ alkylthiol, optionally substituted —$C_{1-20}$ alkylammonium, optionally substituted —$C_{1-20}$ alkylphosphonium, optionally substituted —$C_{1-20}$ alkylsulfonyl, optionally substituted —$C_{1-20}$ alkylosulfinyl, optionally substituted —$CH_2C(=O)$—$C_{1-6}$ alkyl, optionally substituted —$CH_2C(=O)$—O—$C_{1-6}$ alkyl, optionally substituted —$CH_2C(=O)$—N($C_{1-6}$ alkyl)$_2$, optionally substituted —$CH_2C(=O)$—N—($C_{1-6}$ alkyl)-O—$C_{1-6}$ alkyl, optionally substituted —$CH_2C(=O)$—$C_{5-10}$ aryl, optionally substituted —$CH_2C(=O)O$—$C_{5-10}$ aryl, optionally substituted —$CH_2C(=O)$—N($C_{5-10}$ aryl)$_2$, optionally substituted —$CH_2C(=O)$—N—($C_{5-10}$ aryl)-O—$C_{5-10}$ aryl, optionally substituted —$C_{4-10}$heterocyclic, or optionally substituted —$C_{4-10}$ quaternized heterocyclic, wherein each substituent is independently —$C_{1-20}$ alkyl, —$C_{5-10}$ aryl, or a —$C_{4-10}$ heterocyclic group;

$R^1$ may be optionally linked to X or $X^1$ to form a tridentate ligand;

$R^2$ and $R^3$ are, independently, H, optionally substituted —$C_{1-6}$ alkyl, optionally substituted —$C_{3-8}$ cycloalkyl, optionally substituted —$C_{5-10}$ aryl, optionally substituted —$C_{1-20}$ alkylamino, optionally substituted —$C_{1-20}$ alkylphosphino, optionally substituted —$C_{1-20}$ alkylammonium, or optionally substituted —$C_{1-20}$ alkylphosphonium, wherein each substituent is independently: —$C_{5-10}$ aryl, —$C_{4-10}$ heterocyclic, or a —$C_{4-10}$ quaternized heterocyclic group, which in turn may be substituted with at least one: nitro, —$C_{1-6}$ alkyl, —$C_{1-6}$ alkoxy, —$C_{5-10}$ aryl group or halogen;

$R^2$ and $R^3$ may be optionally linked together to form a substituted or unsubstituted, fused —$C_{4-8}$ carbocyclic ring, or a substituted or unsubstituted, fused aromatic ring;

$R^4$ is halogen, optionally substituted —$C_{1-20}$ alkyl, optionally substituted —$C_{2-20}$ alkenyl, optionally substituted —$C_{2-20}$ alkynyl, optionally substituted —$C_{5-10}$ aryl, optionally substituted —$C_{1-20}$ alkoxy, optionally substituted —$C_{2-20}$ alkenyloxy, optionally substituted —$C_{2-20}$ alkynyloxy, optionally substituted —$C_{5-10}$ aryloxy, optionally substituted —$C_{1-20}$ alkoxy carbonyl, optionally substituted —$C_{1-20}$ alkylamino, optionally substituted —$C_{1-20}$ protonated alkylamino, optionally substituted amino, optionally substituted protonated amino, optionally substituted —$C_{1-20}$ alkylphosphino, optionally substituted —$C_{1-20}$ alkylthiol, optionally substituted —$C_{1-20}$ alkylammonium, optionally substituted —$C_{1-20}$ alkylphosphonium, optionally substituted —$C_{4-10}$ quaternized heterocyclic, nitro, carboxyl, optionally substituted amido, optionally substituted sulfonamido, or optionally substituted —$C_{1-20}$ perhaloalkyl; wherein each substituent is independently —$C_{1-20}$ alkyl, —$C_{1-20}$ perhaloalkyl, —$C_{5-10}$ aryl, or a —$C_{4-10}$ quaternized heterocyclic group;

n is 0, 1, 2, 3, or 4;

$R^5$, $R^{5'}$, $R^6$, $R^{6'}$, and $R^7$ are, independently, H, optionally substituted —$C_{1-6}$ alkyl, optionally substituted —$C_{1-20}$ alkylamino, optionally substituted —$C_{1-20}$ alkylphosphino, optionally substituted —$C_{1-20}$ alkylammonium, optionally substituted —$C_{1-20}$ alkylphosphonium, optionally substituted —$C_{4-10}$ heterocyclic, optionally substituted —$C_{4-10}$ quaternized heterocyclic group, wherein each substituent is independently a —$C_{4-10}$ quaternized heterocyclic, —$C_{1-6}$ alkyl, or —$C_{5-10}$ aryl, which in turn may be substituted with nitro, —$C_{1-6}$ alkyl, —$C_{1-6}$ alkoxy, —$C_{5-10}$ aryl group or halogen;

$R^5$ and $R^6$, and $R^{5'}$ and $R^{6'}$ may be optionally linked together to form a substituted or unsubstituted, fused —$C_{4-8}$ carbocyclic ring, or a substituted or unsubstituted, fused aromatic ring;

$R^8$ is optionally substituted —$C_{1-20}$ alkyl, optionally substituted —$C_{3-8}$ cycloalkyl, optionally substituted —$C_{2-20}$ alkenyl, or optionally substituted —$C_{2-20}$ alkynyl; wherein each substituent is independently a halogen atom, —$C_{5-10}$ aryl, —C(=O)—$C_{1-6}$ alkyl, —C(=O)—O—$C_{1-6}$ alkyl, —C(=O)—N($C_{1-6}$ alkyl)$_2$, —C(=O)—N—($C_{1-6}$ alkyl)-O—$C_{1-6}$ alkyl, —C(=O)—$C_{5-10}$ aryl, —C(=O)—O—$C_{5-10}$aryl, —C(=O)—N($C_{5-10}$ aryl)$_2$, or —C(=O)—N—($C_{5-10}$ aryl)-O—$C_{5-10}$ aryl;

p is 1, 2, 3, 4, or 5;

r is 0, 1, 2, or 3;

$R^{8'}$ is H, —$C_{1-20}$ alkyl, $C_{3-8}$ cycloalkyl, —$C_{2-20}$ alkenyl, or —$C_{2-20}$ alkynyl;

q is 0, 1, 2 or 3;

s is 0, 1, 2, or 3; and wherein at least one substituent among $R^2$, $R^3$, $R^5$, $R^{5'}$, $R^6$, $R^{6'}$, and $R^7$ contains a quaternary onium group.

The complex of embodiment 20, wherein

M is ruthenium;

X, $X^1$, $X^2$ and $X^{2'}$ are, independently, halogen, —$C_{1-5}$ carboxyl, —$C_{1-6}$ alkyl, —$C_{5-10}$ aryl, —$C_{1-6}$ alkoxy, —$C_{5-10}$ aryloxy, —$C_{1-5}$ alkylthiol, —$C_{1-5}$ alkylsulfonyl, $CH_3SO_4$, or benzoate;

Y is O, S or N;

R is H, —$C_{1-5}$ alkyl or —$C_{5-10}$ aryl group;

$R^1$ is —$C_{1-6}$ alkyl, $C_{3-8}$ cycloalkyl, —$C_{5-10}$ aryl, —$C_{5-10}$ aryloxy, —$C_{1-6}$ alkylamino, —$C_{1-6}$ alkyloammonium, —$C_{4-10}$ heterocyclic, —$C_{4-10}$ quaternized N-heterocyclic, —$CH_2C(=O)$—$C_{1-6}$ alkyl, —$CH_2C(=O)$—O—$C_{1-6}$ alkyl, —$CH_2C(=O)$—N($C_{1-6}$ alkyl)$_2$, —$CH_2C(=O)$—N—($C_{1-6}$ alkyl)-O—$C_{1-6}$ alkyl, —$CH_2C(=O)$—$C_{5-10}$ aryl, —$CH_2C(=O)$—O—$C_{5-10}$ aryl, —$CH_2C(=O)$—N($C_{5-10}$ aryl)$_2$, or —$CH_2C(=O)$—N—($C_{5-10}$ aryl)-O—$C_{5-10}$ aryl;

$R^2$ and $R^3$ are, independently, H, optionally substituted —$C_{1-6}$ alkyl, optionally substituted —$C_{1-20}$ alkylamino, optionally substituted —$C_{1-20}$ alkylammonium group, wherein each substituent is independently —$C_{5-10}$ aryl, —$C_{4-10}$ N-heterocyclic, or —$C_{4-10}$ quaternized N-heterocyclic, which each in turn may be substituted with one or more nitro, —$C_{1-5}$ alkyl, —$C_{1-5}$ alkoxy, phenyl group or halogen;

$R^2$ and $R^3$ may be optionally linked together to form a substituted or unsubstituted, fused —$C_{4-8}$ carbocyclic ring, or a substituted or unsubstituted, fused aromatic ring;

$R^4$ is halogen, optionally substituted —$C_{1-6}$ alkyl, optionally substituted —$C_{5-10}$ aryl, optionally substituted —$C_{1-6}$ alkoxy, optionally substituted —$C_{5-10}$ aryloxy, optionally substituted —$C_{1-6}$ alkoxy carbonyl, optionally substituted —$C_{1-20}$ protonated alkylamino, optionally substituted proto-nated amino, optionally substituted —$C_{4-10}$ heterocyclic, optionally substituted —$C_{1-12}$ alkylammonium, optionally substituted —$C_{4-10}$ quaternized N-heterocyclic, nitro, carboxyl, optionally substituted amido, optionally substituted sulfonamido, optionally substituted —$C_{1-20}$ perhaloalkyl group, wherein each substituent is independently —$C_{1-6}$ alkyl, —$C_{1-6}$ perhaloalkyl, —$C_{5-10}$ aryl, or a —$C_{4-10}$ quaternized N-heterocyclic group;

n is 0, 1, 2 or 3;

$R^5$, $R^{5'}$, $R^6$, $R^{6'}$, and $R^7$ are, independently, H, optionally substituted —$C_{1-6}$ alkyl, optionally substituted —$C_{1-16}$alkylammonium, or an optionally substituted —$C_{4-10}$ quaternized N-heterocyclic group, wherein each substituent is independently a —$C_{4-10}$ quaternized heterocyclic group;

R⁸ is —C₁₋₆ alkyl;
p is 1, 2, 3 or 4;
R⁸' is H or —C₁₋₆ alkyl; and
q is 0, 1 or 2;
The complex of embodiment 21, wherein
M is ruthenium;
X, X¹, X² and X²' are, independently, halogen, CF₃CO₂, CH₃CO₂, MeO, EtO, PhO, (NO₂)PhO, CH₃SO₃, CF₃SO₃, tosylate, CH₃SO₄ group;
Y is O;
R is H;
R¹ is —C₁₋₆ alkyl, —C₅₋₁₀ aryl, —C₁₋₆ alkylammonium, or a —C₄₋₁₀ quaternized N-heterocyclic group;
R², R³ are, independently, H, optionally substituted —C₁₋₆ alkyl, or an optionally substituted —C₁₋₁₂ alkylammonium group, wherein each substituent is independently a —C₄₋₁₀ quaternized N-heterocyclic group, which in turn may be substituted with at least one —C₁₋₆ alkyl, —C₁₋₅ alkoxy, phenyl group or halogen;
R⁴ is halogen, optionally substituted —C₅₋₁₀ aryl, optionally substituted —C₁₋₆ alkoxy, optionally substituted —C₅₋₁₀ aryloxy, optionally substituted —C₁₋₁₂ alkylammonium, optionally substituted —C₁₋₁₂ protonated alkylamino, optionally substituted protonated amino, optionally substituted —C₄₋₁₀ quaternized N-heterocyclic, nitro, optionally substituted amido, optionally substituted sulfonamido, or an optionally substituted —C₁₋₂₀ perhaloalkyl group, wherein each substituent is independently —C₁₋₆ alkyl, —C₁₋₆ perhaloalkyl, —C₅₋₁₀ aryl, or a —C₄₋₁₀ quaternized N-heterocyclic group;
n is 0, 1 or 2;
R⁵, R⁵', R⁶, R⁶', R⁷ are, independently, H, optionally substituted —C₁₋₆ alkyl, optionally substituted —C₁₋₁₂alkylammonium, or an optionally substituted —C₄₋₁₀ quaternized N-heterocyclic group, wherein each substituent is independently a —C₄₋₁₀ quaternized heterocyclic group;
R⁸ is —C₁₋₆ alkyl;
p is 1 or 2;
R⁸' is H or —C₁₋₆ alkyl; and
q is 0 or 1.
The complex of embodiment 22, wherein substituents X, X¹, X² and X²' are, independently, halogen.
The complex of embodiment 23, wherein substituents X, X¹, X² and X²' are, independently, chlorine or iodine.
The complex of embodiment 20, wherein
R is H, R¹ is an iso-propyl group or

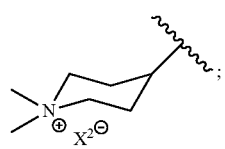

X² is an anionic ligand.
The complex of embodiment 20, wherein
R² and R³ are, independently, H,

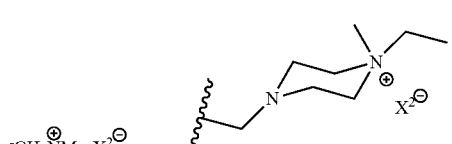

group;
X² is an anionic ligand.

Complexes of formula 1, according to embodiment 20, wherein
R⁴ is a nitro group or

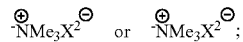

X² and X²' are an anionic ligand; n is 0 or 1.
The complex of embodiment 20, wherein
R⁵ and R⁵' are a methyl or isopropyl group:
R⁶, R⁶' are H;
R⁷ is H, a methyl group or

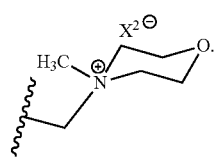

X² is an anionic ligand.
The complex of embodiment 20, wherein R⁸ is a methyl group;
p is 1 or 2;
R⁸' is H or a methyl group;
q is 0 or 1;
The complex of embodiment 20, wherein they are selected from the following formulas 49-55, 58-62

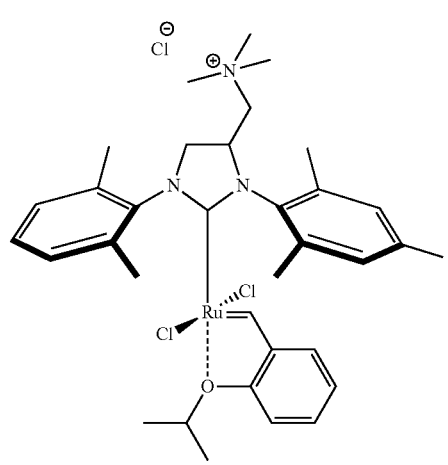

49

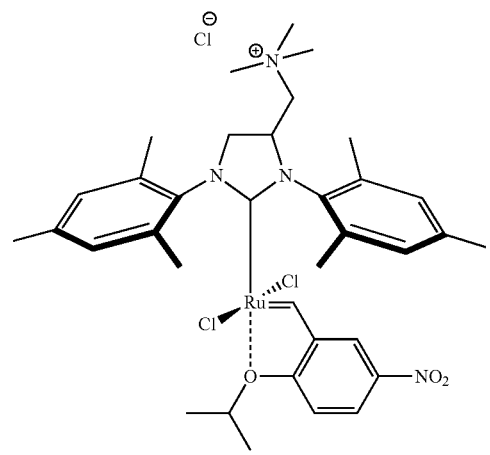

50

-continued
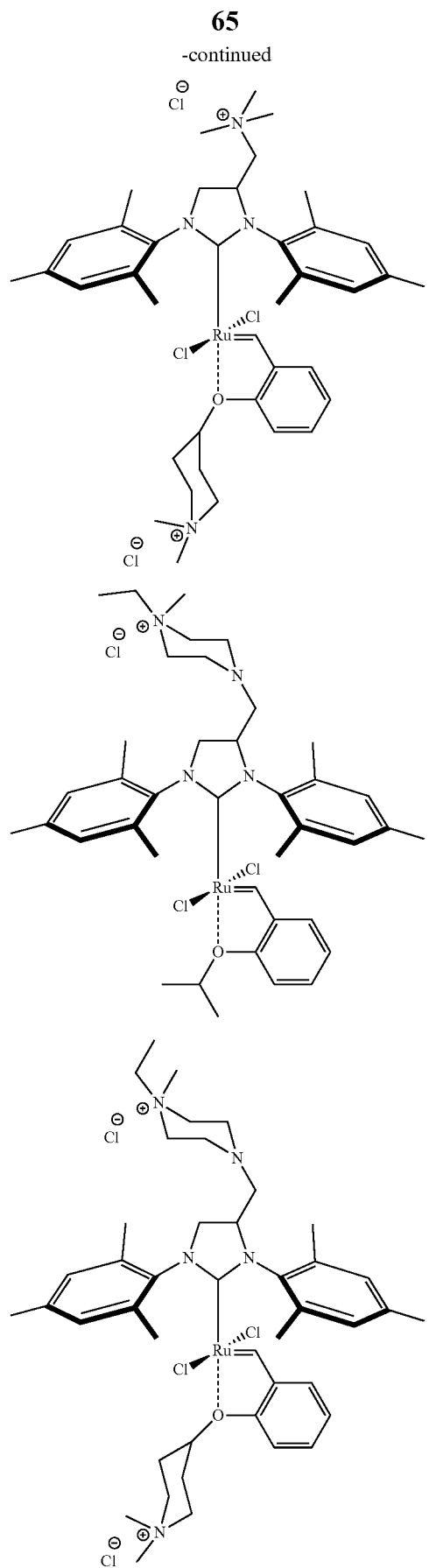
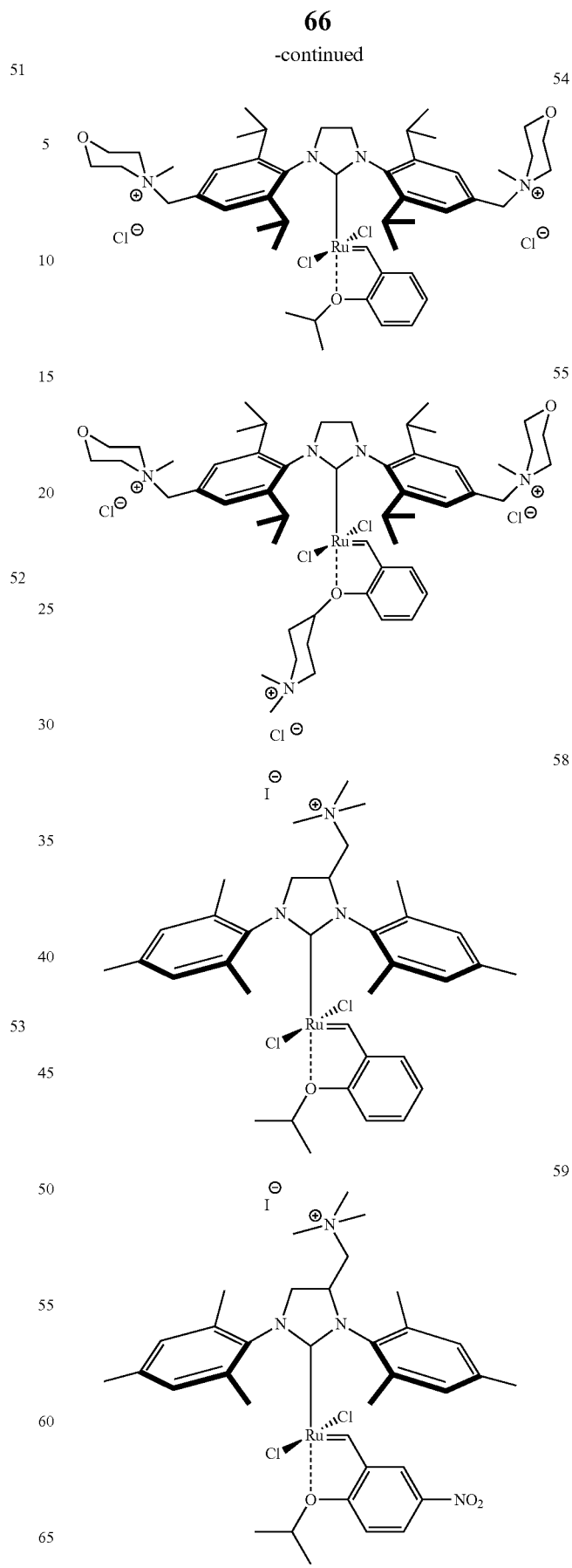

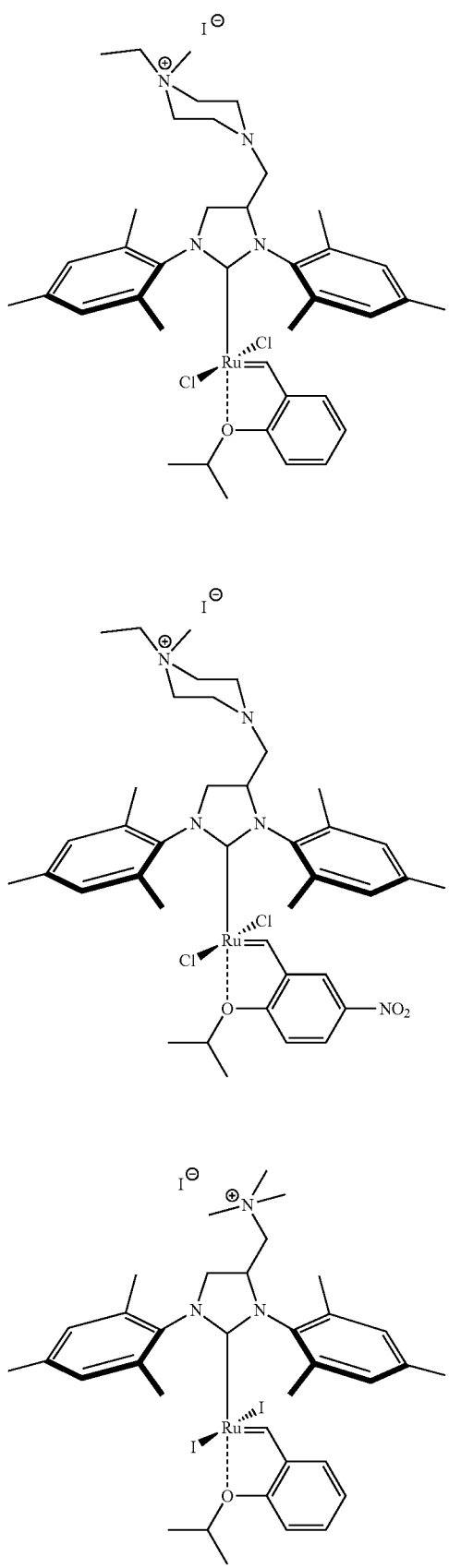

A compound of formula 2a or 2b

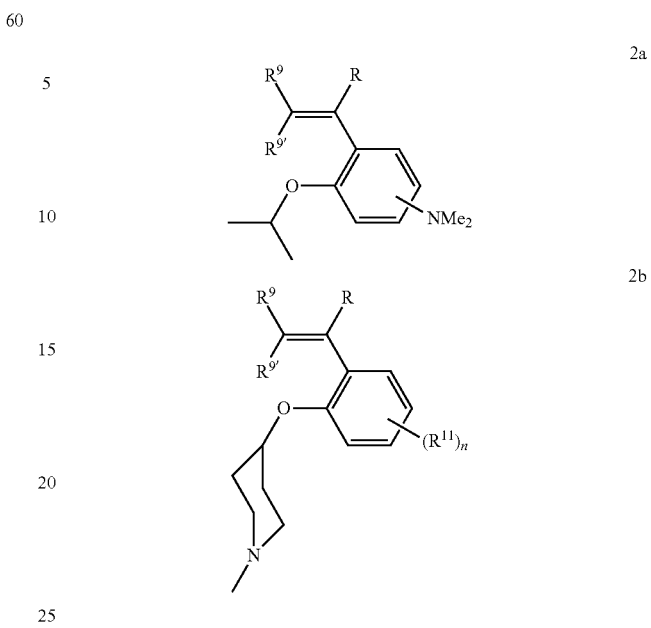

wherein R is H;
$R^9$ and $R^{9'}$ are independently a methyl or ethyl group;
$R^{11}$ is an electron acceptor group;
n is 0 or 1;

The use of complexes of embodiment 20 as (pre)catalysts in metathesis reactions.

The use of embodiment 32, wherein the complexes are used as (pre)catalysts in a ring-closing metathesis (RCM), cross metathesis (CM), homometathesis, alken-alkyn (en-yn) metathesis.

The use according to embodiment 32, wherein complexes are used as (pre)catalysts in a ring opening metathesis polymerization (ROMP).

A method of carrying out an olefin metathesis reaction, wherein at least one olefin is contacted with a complex of embodiment 20 as a (pre)catalyst.

A method according to embodiment 35, wherein a metathesis reaction is carried out in a mixture of water and alcohol.

A method according to embodiment 35, wherein a metathesis reaction is carried out in water.

A method according to embodiment 35, wherein a metathesis reaction is carried out in an organic solvent.

A method according to any one of embodiments 35-38, wherein a metathesis reaction product is purified from the heavy metal pollutants by filtering the reaction mixture through the adsorbent layer.

A method according to any one of embodiments 35-38, wherein a metathesis reaction product is purified from the heavy metal pollutants by adding an appropriate adsorbent to the reaction mixture and by filtration.

A method according to embodiment 39 or 40, wherein an adsorbent is selected from the group consisting of silica gel, alumina, activated alumina, diatomaceous earth and activated carbon.

A method according to embodiment 41, wherein an adsorbent is silica gel.

A method according to any one of embodiments 35-38, wherein a metathesis reaction product is purified from the heavy metal pollutants by extraction with water.

The following abbreviations are used in the description of NMR spectra: s—singlet, bs—broad singlet, d—doublet, dd—doublet of doublet, t—triplet, q—quartet, sept—septet; J—is a coupling constant between two protons.

Synthesis of Compound 19

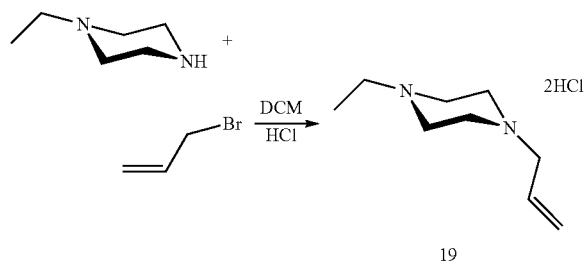

Allyl bromide (68.6 ml, 788 mmol) was slowly added at 0° C. to a solution of N-ethyl-piperazine (100 ml, 788 mmol) in dichloromethane (500 ml). When the addition was completed reaction mixture was heated to reflux and stirred at this temperature for 1.5 h. Then it was cooled to room temperature, washed with sodium hydroxide aq (10%, 350 ml) and dried with magnesium sulphate. Drying agent was filtered off, dichloromethane was evaporated and the residue was dissolved in methanol (100 ml) and hydrochloric acid aq (36%, 157 ml) was added. Removal of solvent and crystallization of crude product from ethanol/diethyl ether mixture afforded 19 (106 g, 59%) as a colorless crystals.

$^1$H (500 MHz, D$_2$O). δ ppm: 6.019-5.936 (m, 1H), 5.730-5.690 (m, 2H), 3.956 (d, 2H, J=7.5 Hz), 3.930-3.450 (bs, 8H), 3.404 (q, 2H, J=7.5 Hz), 1.402 (tr, 3H, J=7.5 Hz). $^{13}$C (125 MHz, D$_2$O). δ ppm: 128.2, 124.7, 59.1, 52.6, 48.4, 48.3, 8.2. HRMS (ESI) calcd for C$_9$H$_{18}$N$_2$ ([M+H]$^+$) m/z 155.1548. found 155.1553.

Synthesis of Compound 20

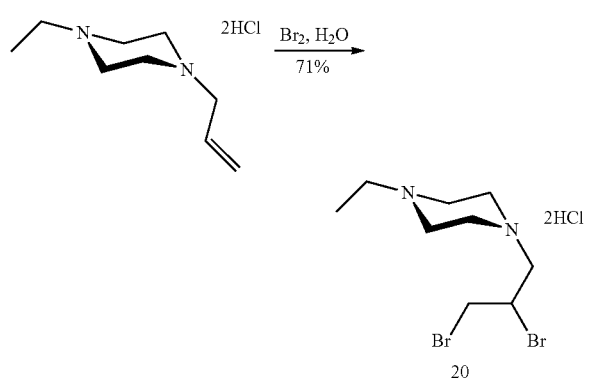

Bromine (23.9 ml, 462 mmol) was slowly added at 50° C. to a solution of 19 (105 g, 462 mmol) in water (200 ml) at such a rate that the temperature did not exceed 60° C. When the addition was completed water was evaporated to dryness. Recrystallization of crude product from ethanol afforded 20 (127 g, 71%) as a colorless crystals.

$^1$H (500 MHz, D$_2$O). δ ppm: 4.100-3.428 (m, 12H), 3.413-3.399 (m, 3H, J=7.5 Hz), 1.405 (tr, 3H, J=7.5 Hz). $^{13}$C (125 MHz, D$_2$O). δ ppm: 64.6, 61.3, 60.4, 52.6, 48.4, 46.3, 8.8. HRMS (ESI) calcd for C$_9$H$_{18}$Br$_2$N$_2$ ([M+H]$^+$) m/z 314.9946. found 314.9934.

Synthesis of Compound 21

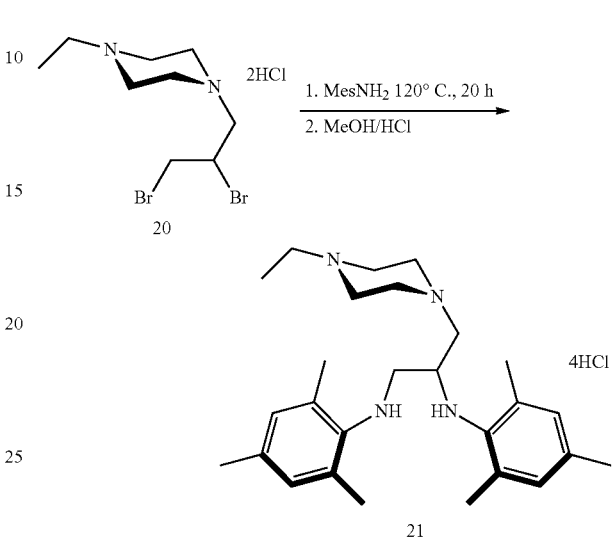

Compound 20 and 2,4,6-trimethylaniline were heated together at 125° C. for 24 h. Reaction mixture was then cooled down to room temperature and alkalized with sodium hydroxide aq (15%, 190 ml). Product was extracted with dichloromethane (300 ml). Organic fraction was washed with water (100 ml) and dried with magnesium sulphate. Drying agent was filtered off and solvent was evaporated. Then excess of 2,4,6-trimethylaniline was removed under reduced pressure (3 mbar). Crude product was dissolved in methanol (200 ml) and hydrochloric acid aq (36%, 51.3 ml) was added. Removal of solvent and crystallization of crude product from acetone (500 ml) afforded 21 (46.3 g, 62%) as a white solid.

$^1$H (500 MHz, D$_2$O). δ ppm: 6.844 (s, 4H), 3.755-3.714 (m, 1H), 3.667-3.624 (m, 2H), 3.600-3.440 (m, 2H), 3.418-3.379 (m, 2H), 3.308-3.262 (m, 2H), 3.216-3.191 (m, 4H), 3.100-2.920 (m, 2H), 2.311-2.183 (m, 20H), 1.367 (tr, 3H, J=7.5 Hz). $^{13}$C (125 MHz, D$_2$O). δ ppm: 140.3, 136.8, 134.2, 131.1, 131.0, 130.7, 58.4, 52.4, 51.9, 49.9, 49.7, 30.4, 19.9, 18.0, 16.9. HRMS (ESI) calcd for C$_{27}$H$_{43}$N$_4$ ([M+H]$^+$) m/z 423.3488. found 423.3473.

Synthesis of Compound 22

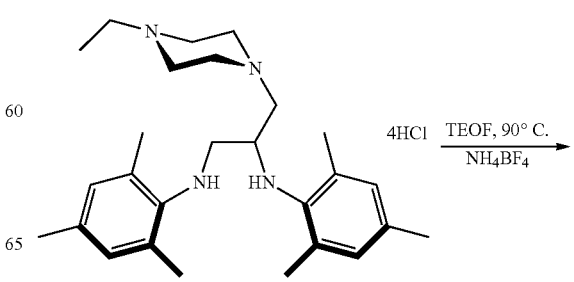

Synthesis of Compound 24

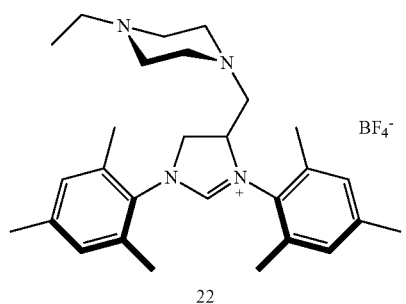

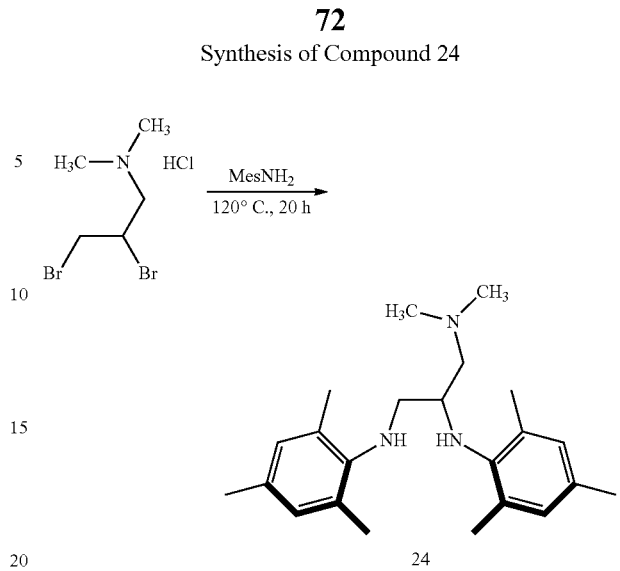

Solution of 21 (72.3 g, 124 mmol) in mixture of triethyl orthoformate (TEOF) (103 ml, 620 mmol) and methanol (170 ml) was stirred at 90° C. for 3 h. After evaporation of solvents, crude product was dissolved in water (100 ml) and solution of ammonium tetrafluoroborate (19.5 g, 186 mmol) in water (200 ml) and sodium hydroxide aq (5%, 180 ml) were added. After extraction of product with dichloromethane (300 ml), organic fraction was dried with sodium sulphate. Drying agent was filtered off and solvent was evaporated. Crude product was purified by recrystallization from dichloromethane/tetrachloromethane mixture to afford 22 (50.5 g, 78%) as a white crystals.

$^1$H (500 MHz, CD$_2$Cl$_2$). δ ppm: 8.226 (s, 1H), 7.070-7.067 (d, 4H, J=1.5 Hz), 5.115-5.046 (m, 1H), 4.653 (m, 1H), 4.159-4.117 (m, 1H), 2.817-2.800 (m, 2H), 2.517-2.472 (m, 8H), 2.413-2.352 (m, 20H), 1.101 (tr, 3H, J=7.0 Hz). $^{13}$C (125 MHz CD2Cl2). δ ppm: 159.4, 141.6, 135.7, 135.5, 130.9, 130.54, 130.5, 61.65, 60.0, 56.3, 52.5, 52.5, 52.4, 21.4, 21.3, 19.0, 18.5, 11.3. HRMS (ESI) calcd for C$_{28}$H$_{41}$N$_4$ ([M+H]$^+$) m/z 433.3331. found 433.3342.

Compound 23 and 2,4,6-trimethylaniline was heated together at 125° C. for 24 h. Reaction mixture was then cooled down to room temperature and alkalized with sodium hydroxide solution aq (15%, 190 ml). Product was extracted with dichloromethane (300 ml). Organic fraction was washed with water (100 ml) and dried with magnesium sulphate. Drying agent was filtered off and solvent was evaporated. Then excess of 2,4,6-trimethylaniline was removed under reduced pressure (3 mbar). Purification of the residue by column chromatografy (DCM/MeOH 9/1) afforded 24 (17.7 g, 70%) as a brown oil.

$^1$H (500 MHz, CDCl$_3$). δ ppm: 6.810-6.775 (m, 4H), 3.606-3.557 (m, 1H), 3.132-3.098 (dd, 1H, J=5.5 Hz, J=11.5 Hz), 3.031-3.009 (m, 2H), 2.962-2.929 (dd, 1H, J=4.5 Hz, J=11.5 Hz), 2.380 (s, 6H), 2.254-2.179 (m, 18H), 1.634 (bs, 2H). $^{13}$C (125 MHz, CDCl$_3$). δ ppm: 144.2, 142.0, 131.4, 129.9, 129.7, 128.9, 65.14, 54.97, 47.19, 46.05, 41.02, 20.80, 18.64, 18.48.

Synthesis of Compound 23

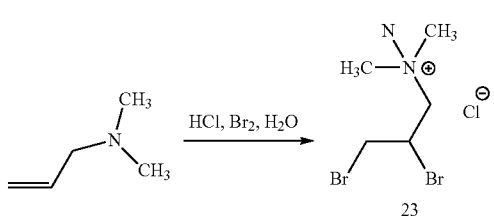

Hydrochloric acid aq (36%, 22.7 ml) was added at 5° C. to a solution of N,N-dimethylallylamine (19.4 g, 228 mmol) in water (20 ml). After that reaction mixture was heated to 50° C. and bromine (11.9 ml, 228) was added at such a rate that the temperature did not exceed 60° C. When the addition was completed water was evaporated to dryness. Recrystallization of crude product from ethanol afforded 23 (127 g, 71%) as a colorless crystals.

$^1$H (200 MHz, D$_2$O). δ ppm: 4.133-3.602 (m, 5H), 2.990 (s, 6H). $^{13}$C (50 MHz, D$_2$O). δ ppm: 61.7, 60.8, 45.7, 45.1, 30.0.

Synthesis of Compound 25

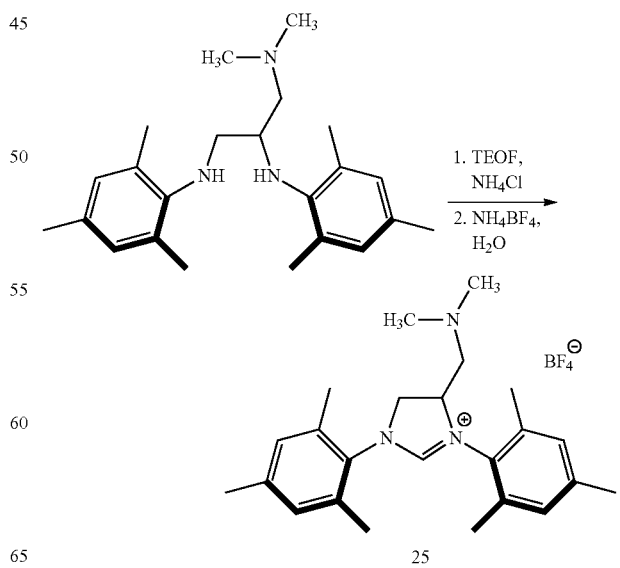

Solution of 24 (13.3 g, 37.6 mmol) and ammonium chloride (2 g, 37.6 mmol) in TEOF was stirred at 120° C. for 3 h. After evaporation of solvent, the residue was dissolved in water (100 ml) and solution of ammonium tetrafluoroborate (3.94 g, 37.6 mmol) in water (20 ml) was added. Crude product was filtered off and recrystallized from DCM/CCl$_4$ mixture to afford 25 (10.5 g, 62%) as a white crystals.

$^1$H (500 MHz, CDCl$_3$). δ ppm: 8.158 (s, 1H), 6.953 (s, 4H), 4.996-4.928 (m, 1H), 4.621-4.573 (m, 1H, J=7.2 Hz), 4.125 (dd, 1H, J=8.5, J=12.5 Hz), 2.715 (dd, 1H, J=9.5 Hz, J=12.0 Hz), 2.539 (dd, 1H, J=5.0 Hz, J=12.0 Hz), 2.396-2.288 (m, 18H), 2.157 (s, 6H). $^{13}$C (125 MHz, CDCl$_3$). δ ppm: 159.2, 140.8, 135.4, 130.6, 130.3, 129.6, 62.13, 60.97, 56.11, 45.84, 21.31, 21.26, 18.74, 18.30, 17.78.

Synthesis of Compound 27

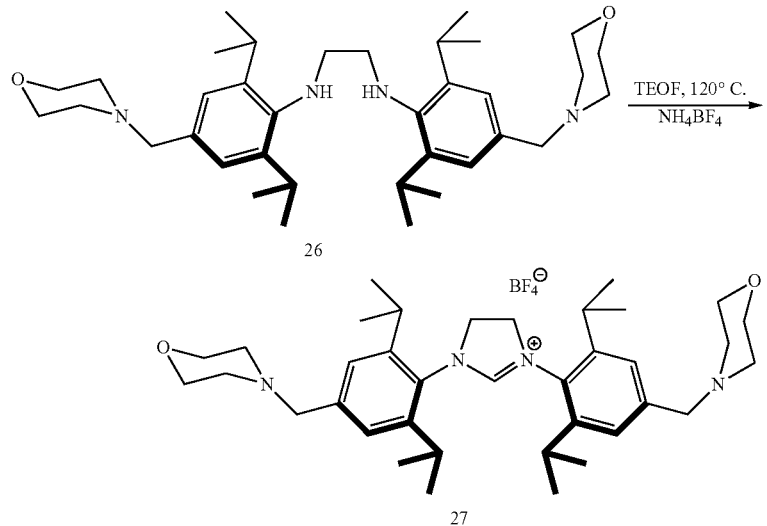

Compound 26 (see: Volodymyr Sashuk, Dirk Schoeps, Herbert Plenio, Chem. Commun., 2009, 770-772) (10.13 g, 17.50 mmol) and ammonium tetrafluoroborate (1.926 g, 18.37 mmol) were dissolved in TEOF (150 ml) and stirred at 120° C. for 3 h. Then reaction mixture was cooled to room temperature and hexane (150 ml) was added to precipitate the product. Crude product was filtered and recrystallized from acetone to afford the 27 (4.59 g, 39%) as a white solid.

$^1$H (200 MHz, CDCl$_3$) δ ppm: 7.806 (s, 1H), 7.208 (d, 4H, J=4 Hz), 4.538 (s, 4H), 3.662-3.618 (m, 8H), 3.472 (s, 4H), 2.918 (m, 4H), 2.413-2.369 (m, 8H), 1.327 (d, 12H, J=6.6 Hz), 1.174 (d, 12H, J=6.6 Hz).

Synthesis of Compound 28

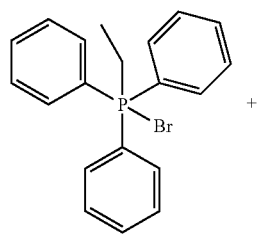

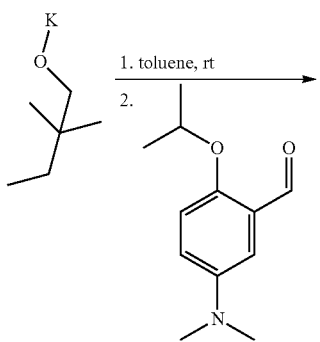

-continued

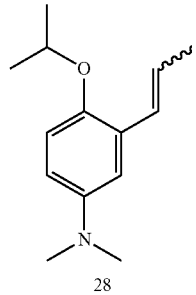

28

Potassium tert-amylate (1.7 M in toluene, 13 ml, 22.1 mmol) was added at 0° C. to a suspension of ethyltriphenylphosphonium bromide (8.51 g, 22.9 mmol) in dry toluene (65 mil). After that mixture was warmed to room temperature and stirred for 1 h. Then it was cooled to −15° C. and solution of 5-dimethylamino-2-isopropoxy-benzaldehyde (3.27 g, 15.8 mmol) in dry toluene (35 mil) was dropped in. Next reaction mixture was slowly warmed to room temperature and stirred overnight. The reaction was quenched with saturated NH$_4$Cl aq (30 mil). The organic solvent was removed under reduced pressure and the residue was extracted with tert-butyl-methyl ether (4×20 mL). The combined organic layers were dried with magnesium sulphate, filtered and concentrated under reduced pressure. The crude product was purified by column chromatography (c-hexane/EtOAc/Et3N 19:1:0.1) to give 28 (3.10 g, 89%) as a yellow oil.

$^1$H (300 MHz, CDCl$_3$) δ ppm: 6.864-6.806 (m, 1H), 6.759 (d, 1H, J=3 Hz), 6.667-6.628 (m, 1H), 6.582-6.537 (m, 1H), 5.826-5.764 (m, 1H), 4.324 (heptet, 1H, J=6.3 Hz), 2.898 (s, 6H), 1.887-1.857 (m, 3H), 1.382-1.282 (d, 6H, J=6 Hz). HRMS (ESI) calcd for C$_{14}$H$_{22}$NO ([M+H]$^+$) m/z 220.1701. found 220.1700.

Synthesis of Compound 29

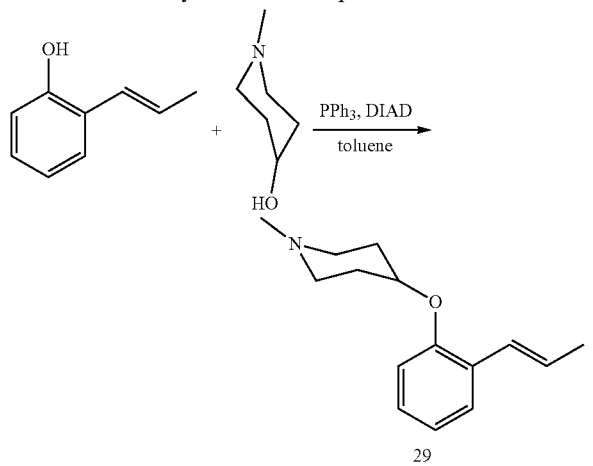

2-Propenyl-phenol was added under argon to a solution of 1-methyl-piperidin-4-ol (2.60 g, 22.6 mmol) and triphenylphosphine (6.52 g, 24.9 mmol) in dry toluene (40 ml). Mixture was cooled to 0° C. and diizopropyl azodicaroxylate (4.9 ml, 24.9 mmol) was slowly added. When the addition was completed reaction mixture was warmed to room temperature and stirred for 20 h and then for 4 h at 60° C. Mixture was cooled to room temperature, diluted with ethyl acetate (150 ml) and washed with water (200 ml) and with saturated potassium carbonate aq (200 ml). Product was extracted from organic phase with hydrochloric acid aq (0.5 M, 240 ml). Water fraction was then alkalized to pH 10 and product was extracted with dichloromethane (240 ml). Organic phase was washed with water (100 ml), dried with magnesium sulphate, filtered and solvent was evaporated. Crude product was purified by column chromatography (DCM/c-hexane/EtOAc/Et$_3$N 3:3:1:0.1). Evaporation of solvents afforded 29 (4.26 g, 81%) as a yellow oil.

$^1$H (200 MHz, CDCl$_3$) δ ppm: 7.725-6.826 (m, 4H), 6.793-6.705 (m, 1H), 6.316-5.727 (m, 1H), 4.381-4.271 (m, 1H), 2.750-2.629 (m, 2H), 2.380-2.104 (m, 2H) 2.309 (s, 3H), 2.080-1.182 (m, 7H).

Synthesis of Complex 31

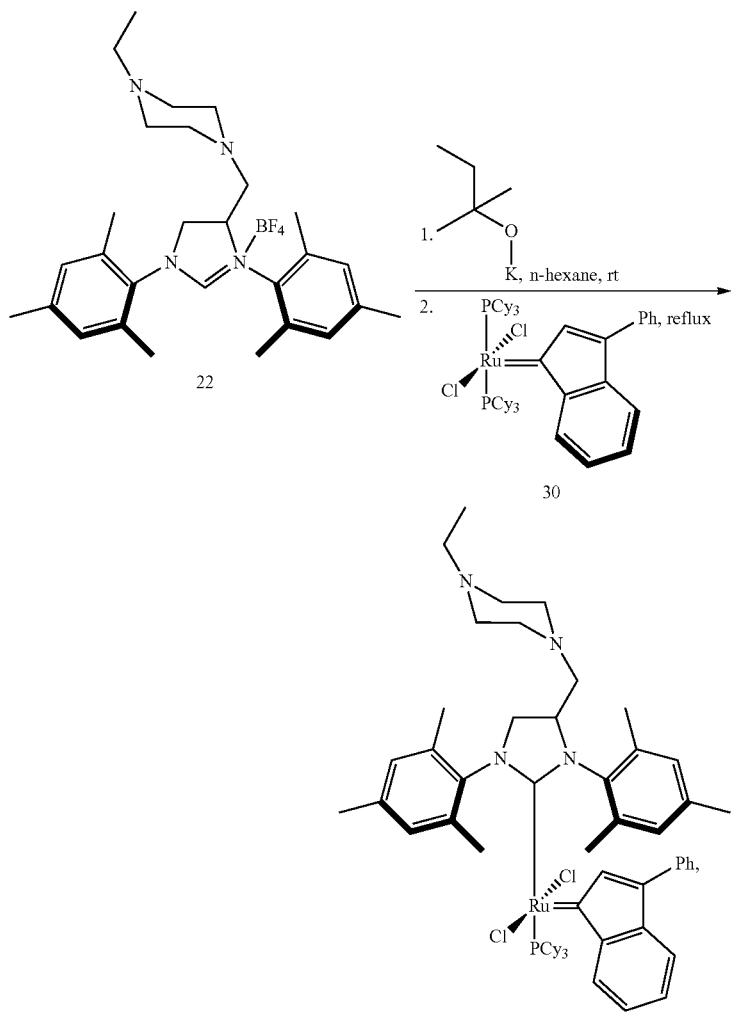

Potassium t-amylate (1.7 M in toluene, 2.26 ml, 3.85 mmol) was added at room temperature to a suspension of 22 (2.00 g, 3.85 mmol) in dry hexane (40 ml) under argon. Reaction mixture was stirred at room temperature for 1 h, then complex 30 was added and stirring was continued at reflux for 1 h. After cooling down, reaction mixture was filtered through a short pad of silica gel (c-hexane/EtOAc 8:2). Solvents were evaporated, catalyst was washed with n-pentane and dried under vacuum to afford complex 31 (2.51 g, 85%) as a dark red solid.

$^1$H (300 MHz, CDCl$_3$) δ ppm: 8.668-8.519 (m, 1H), 7.668-7.392 (m, 2H), 7.525-7.008 (m, 9H), 6.448-6.370 (m, 1H), 6.013-5.945 (m, 1H), 4.146-3.655 (m, 3H), 2.741-2.722 (m, 3H), 2.661-2.624 (m, 4H), 2.556-2.386 (m, 3H), 2.319-1.832 (m, 24H), 1.628-1.362 (m, 7H), 1.340-1.222 (m, 4H), 1.140-0.959 (m, 18H), 0.882 (tr, 3H, J=7.2 Hz). $^{31}$P (124.5 MHz, CDCl$_3$) δ ppm: 26.09, 26.47, 24.66. $^{13}$C (75.4 MHz, CDCl$_3$) δ ppm: 292.6, 219.4-217.7 (m), 144.9, 144.8, 144.7, 140.9, 140.8, 139.1, 138.9, 138.8, 138.4, 138.0, 137.9, 137.6, 137.0, 136.9, 136.7, 136.4, 136.2, 136.9, 135.4, 135.3, 134.8, 134.7, 130.1, 129.9, 129.4, 129.3, 128.9, 128.8, 128.6, 128.1, 128.0, 127.4, 127.1, 127.0, 126.8, 126.4, 126.3, 115.9, 115.8, 62.71, 62.48, 62.14, 61.21, 60.6, 60.50, 60.36, 58.69, 58.49, 57.88, 53.40, 52.27, 33.24, 33.03, 32.82, 29.30, 29.22, 29.12, 27.89, 27.75, 27.61, 26.26, 21.20, 14.10, 11.90. HRMS (ESI) calcd for C$_{61}$H$_{83}$N$_4$PClRu ([M-Cl]$^+$) m/z 1039.5087. found 1039.5063.

Synthesis of Complex 32

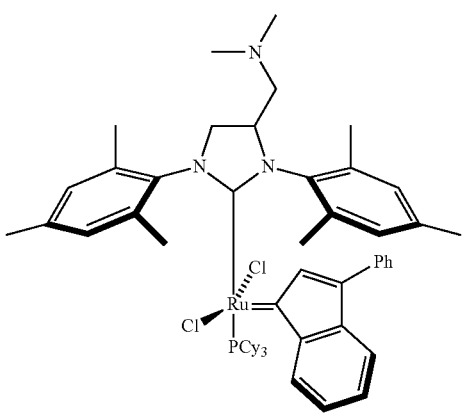

32

The same procedure as described for complex 31 was employed to afford the catalyst 32 as a dark red solid in 81% yield.

0.250 g (81%)—red solid; $^1$H (300 MHz, CDCl$_3$) δ ppm: 8.684-8.537 (m, 1H), 7.746-7.673 (m, 2H), 7.530-7.460 (m, 1H), 7.426-7.353 (m, 2H), 7.227-7.096 (m, 2H), 7.074-7.008 (m, 3H), 6.923-6.779 (m, 1H), 6.444-6.377 (m, 1H), 6.031-5.957 (m, 1H), 4.538-4.288 (m, 1H), 4.231-4.108 (m, 1H), 3.997-3.632 (m, 1H), 2.767-2.720 (m, 2H), 2.677-2.635 (m, 3H), 2.385-2.232 (m, 4H), 2.289-2.255 (m, 5H), 2.234-2.201 (m, 5H), 2.168-2.094 (m, 8H), 2.073-2.019 (m, 3H), 1.979-1.799 (m, 4H), 1.487-1.430 (m, 10H), 1.143-0.863 (m, 15H). $^{31}$P (124.5 MHz, CDCl$_3$) δ ppm: 26.09, 26.47, 24.66. $^{13}$C (75.4 MHz, CDCl$_3$) δ ppm: 292.6-292.3 (m), 219.6-217.6 (m), 164.40, 143.88, 140.97, 140.5, 139.44, 139.24, 138.90, 138.75, 138.33, 138.04, 137.90, 137.60, 137.40, 137.21, 137.12, 137.06, 136.98, 136.85, 137.67, 137.54, 136.42, 136.22, 135.90, 131.13, 130.24, 130.10, 129.95, 129.48, 129.35, 128.60, 128.11, 126.65, 126.38, 126.30, 115.9, 115.83, 62.59, 61.95, 61.84, 57.95, 56.67, 52.52, 46.04, 46.90, 29.31-29.23 (m), 27.9, 26.95, 26.26, 21.2-20.33 (m), 19.19-18.39 (m). HRMS (ESI) obliczono dla C$_{57}$H$_{76}$N$_3$PClRu ([M-Cl]$^+$) m/z 970.4509 oznaczono 970.4512.

Synthesis of Complex 34

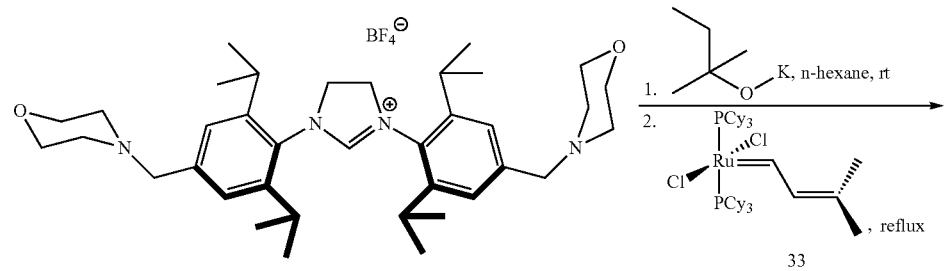

33

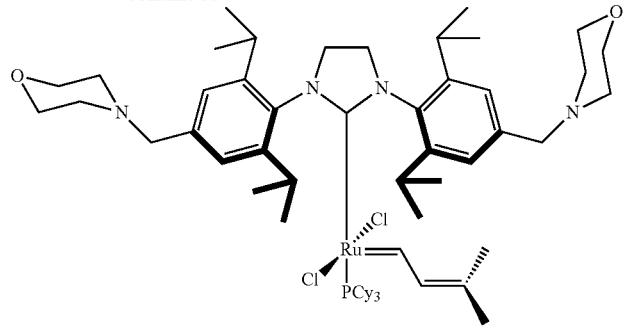

34

Potassium t-amylate (1.7 M in toluene, 0.224 ml, 0.381 mmol) was added at room temperature to a suspension of 27 (0.250 g, 0.423 mmol) in dry hexane under argon. Reaction mixture was stirred at room temperature for 1 h, then complex 33 was added and stirring was continued at reflux for 1 h. After cooling down, reaction mixture was directly filtered through a short pad of silica gel (c-hexane/EtOAc 8:2). Solvents were evaporated, catalyst was washed with n-pentane and dried under vacuum to afford complex 34 (0.24 g, 77%) as a light brown solid.

$^1$H (300 MHz, CDCl$_3$) δ ppm: 18.700 (d, 1H, J=11.3 Hz), 7.363 (d, 1H, J=11.3 Hz), 7.223 (s, 2H), 7.014 (s, 2H), 4.110-4.044 (m, 2H), 3.959-3.819 (m, 4H), 3.781-3.729 (m, 8H), 3.570-3.444 (m, 6H), 2.518-2.460 (m, 8H), 2.185-2.077 (m, 4H), 1.525-1.497 (m, 10H), 1.466-1.414 (m, 13H), 1.270-1.126 (m, 14H), 1.086-0.948 (m, 22H). $^{31}$P (124.5 MHz, CDCl$_3$) δ ppm: 25.80. $^{13}$C (75.4 MHz, CDCl$_3$) δ ppm: 287.7, 222.5, 149.5, 147.5, 146.1, 138.7, 137.1, 136.9, 128.9, 125.1, 124.7, 67.15, 63.38, 54.57, 54.19, 53.69, 53.63, 31.68, 31.47, 28.93, 28.60, 27.82, 27.70, 27.54, 27.00, 26.69, 26.42, 26.17, 23.94, 23.06, 20.04. HRMS (ESI) calcd for C$_{60}$H$_{97}$N$_4$O$_2$PClRu ([M-Cl]$^+$) m/z 1073.6081. found 1073.6084.

Synthesis of Complex 35

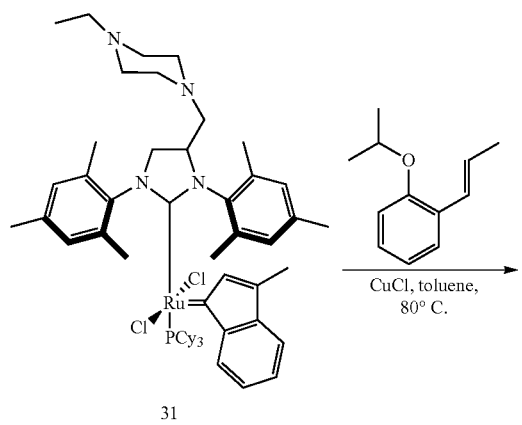

31

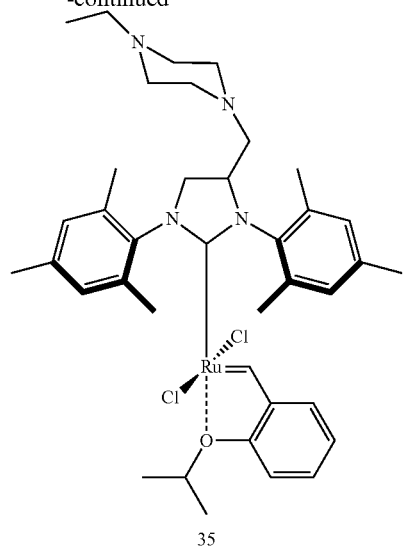

35

1-Isopropoxy-2-propenyl-benzene (0.143 g, 0.814 mmol) and CuCl (0.121 g, 1.221 mmol) were placed in a Schlenk flask. The flask was filled with argon and then dry toluene (20 ml) was added. Afterwards complex 31 (0.876 g, 0.814 mmol) was added and the resulting solution was stirred at 80 t for 20 min. The reaction mixture was cooled to room temperature and concentrated under vacuum. The resulting material was dissolved in a minimum amount of EtOAc and the insoluble white solid filtered through a Pasteur pipette containing cotton wool. The solvent was concentrated again in vacuum, and the crude catalyst was purified by flash chromatography (c-hexane/EtOAc 7:3). Removal of solvents afforded complex 35 (0.42 g, 68%) as a green solid.

$^1$H (300 MHz, CDCl$_3$) δ ppm: 16.533 (s, 1H), 7.507-7.450 (m, 1H), 7.075-7.045 (m, 4H), 6.934-6.770 (m, 3H), 4.890 (heptet 1H, J=6.6 Hz), 4.609-4.558 (m, 1H), 4, 272 (tr, 1H, J=10.2 Hz), 4.036-3.973 (m, 1H), 2.762-2.673 (m, 2H), 2.400-2.319 (m, 28H), 1.260 (d, 6H, J=6.6 Hz), 1.0457 (tr, 3H, J=7.2 Hz). $^{13}$C (75.4 MHz, CDCl$_3$) δ ppm: 298.2, 213.2, 152.2, 145.4, 139.4, 138.8, 138.6, 129.6, 129.5, 122.8, 122.3, 112.9, 74.93, 61.35, 57.73, 57.64, 57.33, 57.30, 53.60, 52.76, 52.29, 21.47, 11.97. HRMS (ESI) calcd for C$_{38}$H$_{52}$N$_4$ONaCl$_2$Ru ([M+Na]$^+$) m/z 775.2459. found 775.2436.

Synthesis of Complex 36

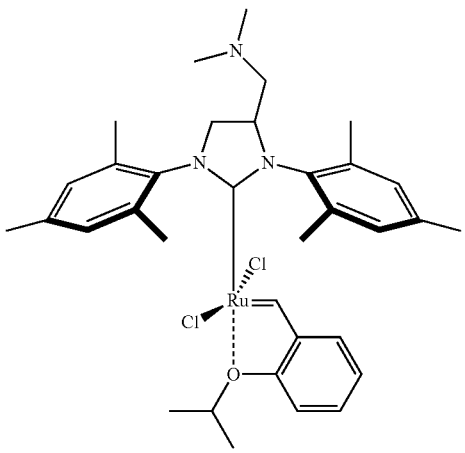

36

The same procedure as described for complex 35 was employed to afford the catalyst 36 as a green solid in 64% yield.

0.340 g (64%)—green solid, $^1$H (300 MHz, CDCl$_3$) δ ppm: 16.510-16.530 (bs, 1H), 7.486-7.477 (m, 1H), 7.060-7.072 (m, 4H), 6.930-6.940 (m, 1H), 6.848-6.856 (m, 1H), 6.782-6.802 (m, 1H), 4.890 (heptet, 1H, J=6.3 Hz), 4.563-4.500 (m, 1H), 4.284 (m, 1H), 4.022 (dd, 1H, J=8.1 Hz, J=10.5 Hz), 2.757-2.683 (m, 2H), 2.530-2.290 (m, 18H), 2.201 (s, 6H), 1.284-1.258 (m, 6H). $^{13}$C (75.4 MHz, CDCl$_3$) δ ppm: 298.2, 213.2, 145.4, 139.4, 138.8, 138.7, 130.0, 129.7, 129.6, 129.3, 122.8, 122.3, 112.9, 74.93, 62.61, 57.63, 46.13, 21.15. HRMS (ESI) calcd for C$_{34}$H$_{45}$N$_3$ONaCl$_2$Ru ([M+Na]$^+$) m/z 706.1881. found 706.1865.

Synthesis of Complex 37

37

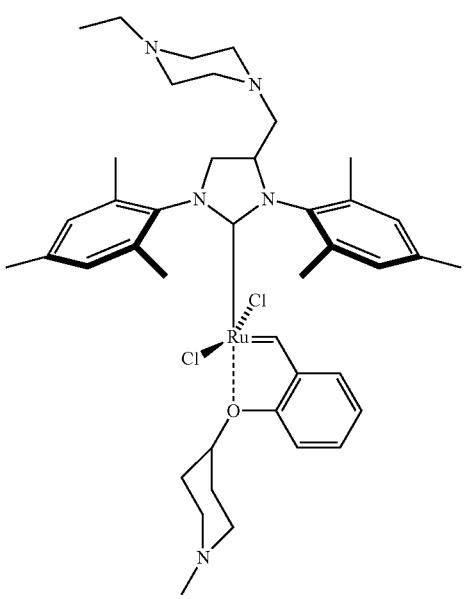

The same procedure as described for complex 35 was employed to afford the catalyst 37 as a green solid in 37% yield. Column chromatography was performed using c-hexane/EtOAc 1:1 mixture.

0.280 g (37%)—green solid; $^1$H (300 MHz, CDCl$_3$) δ ppm: 16.504 (s, 1H), 7.46 (m, 1H), 7.081-7.063 (m, 4H), 6.953-6.829 (m, 2H), 6.762 (d, 1H, J=8.1 Hz), 4.591 (m, 1H), 4.468 (m, 1H), 4.270 (m, 1H), 4.000 (m, 1H), 2.759-2.691 (m, 4H), 2.492-2.315 (m, 26H), 2.238 (s, 3H), 1.970-1.746 (m, 8H), 1.043 (tr, 3H, J=7.2 Hz). $^{13}$C (75.4 MHz, CDCl$_3$) δ ppm: 297, 9, 213.2, 151.9, 136.6, 138.8, 138.6, 130.0, 129.6, 129.5, 123.00 122.6, 112.7, 78.91, 61.36, 53.93, 53.59, 52.77, 52.30, 45.59, 30.10, 26.95, 21.20, 11.99. HRMS (ESI) calcd for C$_{41}$H$_{57}$N$_5$OClRu ([M-Cl]$^+$) m/z 772.3295. found 772.3283.

Synthesis of Complex 38

38

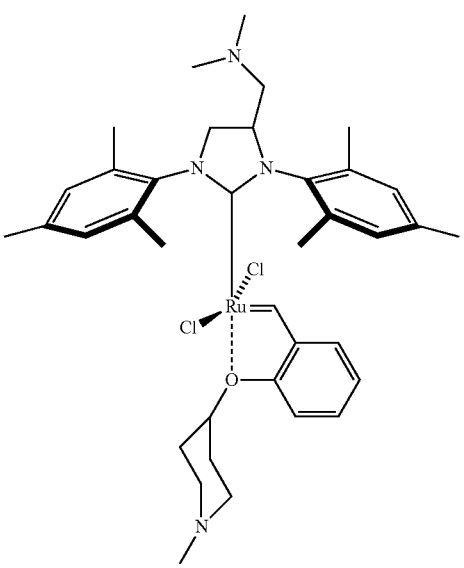

The same procedure as described for complex 35 was employed to afford the catalyst 38 as a green solid in 38% yield. Column chromatography was performed using c-hexane/EtOAc 1:1 mixture.

0.200 g (38%)—green solid; $^1$H (300 MHz, CDCl$_3$) δ ppm: 16.583-16.303 (bs, 1H), 7.708-7.640 (m, 1H), 7.847-7.436 (m, 2H), 7.090-7.070 (m, 3H), 6.912-6.831 (m, 1H), 6.776-6.748 (d, 1H, J=8.4 Hz), 4.570-4.472 (m, 2H), 4.313 (tr, 1H, J=10.5 Hz), 4.018-3.983 (m, 1H), 2.766-2.675 (m, 2H), 2.531-2.284 (m, 18H), 2.237 (s, 3H), 2.195 (s, 6H), 1.972-1.746 (m, 8H). $^{13}$C (75.4 MHz, CDCl$_3$) δ ppm: 297.6, 212.9, 151.9, 145.2, 139.6, 138.7, 138.6, 132.2, 132.1, 131.97, 129.6, 129.5, 129.4, 128.5, 123.0, 122.6, 112.7, 78.80, 62.60, 53.90, 46.14, 45.58, 30.08, 21.22. HRMS (ESI) calcd for C$_{37}$H$_{50}$N$_4$OClRu ([M-Cl]$^+$) m/z 703.2717. found 703.2717.

Synthesis of Complex 39

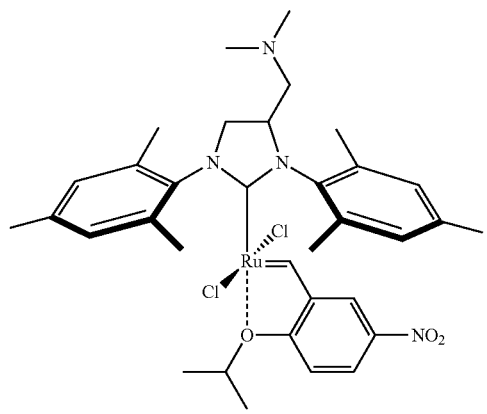

The same procedure as described for complex 35 was employed to afford the catalyst 39 as a green solid in 69% yield.

0.300 g (69%)—green solid; $^1$H (300 MHz, CDCl$_3$) δ ppm: 16.420 (s, 1H), 8.440-8.401 (dd, 1H, J=2.7 Hz, J=9.0 Hz), 7.805 (d, 1H, J=2, 7 Hz), 7.096-7.081 (m, 4H), 6.885 (d, 1H, J=9.0 Hz), 4.968 (heptet, 1H, J=6.3 Hz), 4.625-4.514 (m, 1H), 4.306 (m, 1H), 4.005 (dd, 1H, J=8.4 Hz, J=10.5 Hz), 2.712 (m, 2H), 2.549-2.448 (m, 18H), 2.204 (s, 6H), 1.306-1.274 (m, 6H). $^{13}$C (75.4 MHz, CDCl$_3$) δ ppm: 292.2, 209.9, 156.4, 144.7, 143.1, 139.4, 139.3, 139.2, 129.7, 129.5, 124.2, 117.5, 112.80, 62.55, 57.55, 46.11, 26.94, 21.12. HRMS (ESI) calcd for C$_{34}$H$_{40}$N$_4$O$_3$ClRu ([M-Cl]$^+$) m/z 689.1832. found 689.1838.

Synthesis of Complex 40

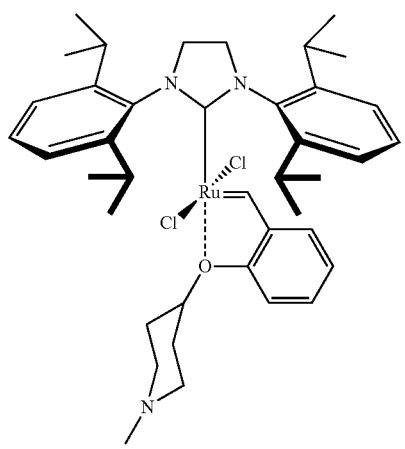

The same procedure as described for complex 35 was employed to afford the catalyst 40 as a green solid in 64% yield.

0.125 g (64%)—green solid; $^1$H (300 MHz, CDCl$_3$) δ ppm: 16.395 (s, 1H), 7.566-7.515 (m, 2H), 7.429-7.391 (m, 5H), 6.832-6.766 (m, 3H), 4.508-4.478 (m, 1H), 4.189 (s, 4H), 3.649-3.560 (m, 4H), 2.779-2.761 (m, 2H), 2.203 (s, 3H), 2.104-1.926 (m, 6H), 1.271-1.238 (m, 24H). $^{13}$C (75.4 MHz, CDCl$_3$) δ ppm: 290.1, 213.7, 152.2, 149.2, 144.0, 136.7, 129.8, 129.2, 124.4, 122.5, 122.4, 112.8, 79.09, 54.59, 53.89, 45.56, 30.50, 28.84, 26.66, 23.39. HRMS (ESI) calcd for C$_{40}$H$_{56}$N$_3$OCl$_2$Ru ([M+H]$^+$) m/z 766.2844. found 766.2856.

Synthesis of Complex 41

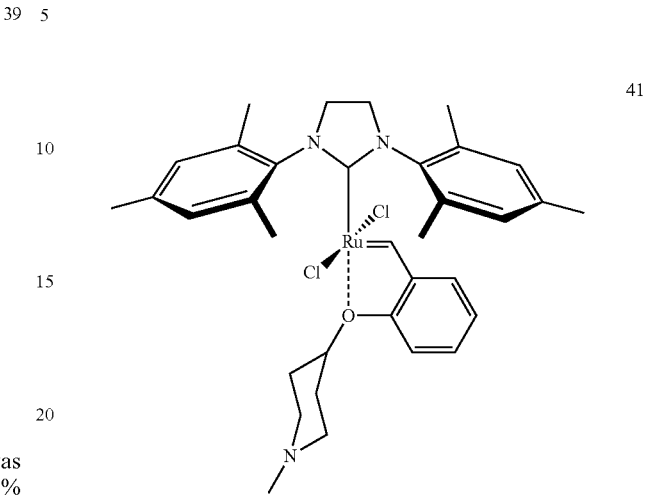

The same procedure as described for complex 35 was employed to afford the catalyst 41 as a green solid in 44% yield.

0.224 g (44%)—green solid; $^1$H (300 MHz, CDCl$_3$) δ ppm: 16.538 (s, 1H), 7.498-7.442 (m, 1H), 7.088 (s, 4H), 6.953-6.7560 (m, 3H), 4.540-4.445 (m, 1H), 4.178 (s, 4H), 2.776-2.727 (m, 2H), 2.472-2.425 (m, 18H), 2.239 (s, 3H), 2.041-1.754 (m, 6H). $^{13}$C (75.4 MHz, CDCl$_3$) δ ppm: 297.3, 211.3, 151.9, 145.14, 138.80, 129.5, 129.4, 123.0, 122.6, 112.7, 78.65, 53.85, 51.47, 45.47, 30.03, 29.95, 21.21, 19.47. HRMS (ESI) calcd for C$_{34}$H$_{43}$N$_3$OClRu ([M-Cl]$^+$) m/z 646.2138. found 646.2145.

Synthesis of Complex 42

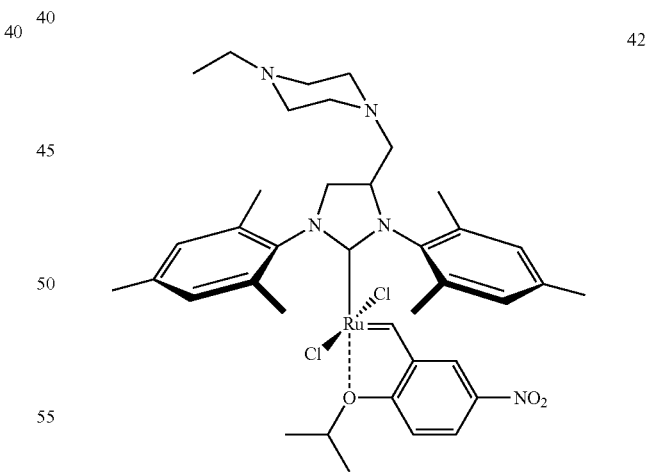

The same procedure as described for complex 35 was employed to afford the catalyst 42 as a green solid in 69% yield.

0.51 g (69%)—green solid; $^1$H (300 MHz, CDCl$_3$) δ ppm: 16.433 (m, 1H), 8.431-8.386 (m, 1H), 7.805-7.795 (m, 1H), 7.093-7.075 (m, 4H), 6.918-6.868 (m, 1H), 5.003-4.921 (heptet, 1H, J=6.3 Hz), 4.648-4.563 (m, 1H), 4.331-4.260 (m, 1H), 4.056-3.992 (m, 1H), 2.763-2.698 (m, 2H), 2.656-2.147 (m, 28H), 1.360-1.207 (d, 6H, J=6.3 Hz), 1.091-1.022 (t, 3H, J=6.9 Hz). $^{13}$C (75.4 MHz, CDCl$_3$) δ ppm: 292.1, 210.0, 156.3, 144.7, 143.1, 139.4, 139.3, 130.1, 129.7, 129.5, 129.3, 124.3, 117.4, 112.8, 61.75, 61.62, 61.28, 57.48, 53.52, 52.74, 52.30, 26.94, 22.36, 21.84, 21.13, 21.11, 20.98, 20.91, 20.48, 19.00, 18.92, 18.57, 17.95, 14.10, 11.93. HRMS (ESI) obliczono dla $C_{38}H_{51}N_5O_3ClRu$ ([M-Cl]$^+$) m/z 762.2724 oznaczono 762.2733.

Synthesis of Complex 43

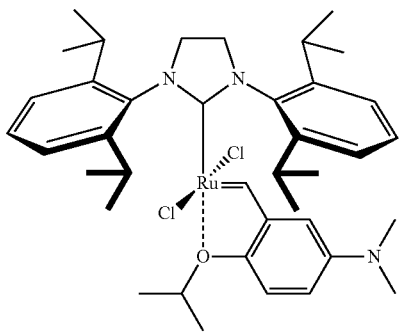

43

The same procedure as described for complex 35 was employed to afford the catalyst 43 as a green solid in 71% yield.

0.211 g (71%)—green solid; $^1$H (300 MHz, CDCl$_3$) δ ppm: 16.322 (s, 1H), 7.555-7.504 (m, 2H), 7.393-7.367 (m, 4H), 6.928 (dd, 1H, J=3.0 Hz, J=8.7 Hz), 6.678 (d, 1H, J=8.7 Hz), 6.258 (d, 1H, J=3 Hz), 4.829 (heptet, 1H, 6.3 Hz), 4.183 (s, 4H), 3.619 (m, 4H), 2.800 (s, 6H), 1.346 (d, 6H, J=6.3 Hz), 1.236 (d, 24H, J=6.9 Hz). $^{13}$C (75.4 MHz, CDCl$_3$) δ ppm: 291.3, 214.4, 149.3, 146.8, 145.4, 144.3, 136.9, 129.5, 124.4, 114.8, 112.9, 108.0, 74.26, 54.54, 41.9, 28.81, 26.62, 23.47, 21.81. HRMS (ESI) calcd for $C_{39}H_{55}N_3OClRu$ ([M-Cl]$^+$) m/z 718.3077. found 718.3054.

Synthesis of Complex 44

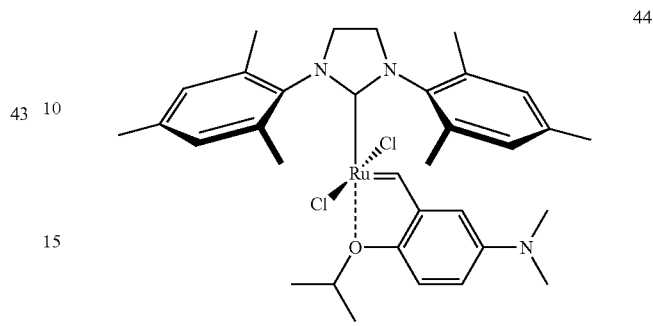

44

The same procedure as described for complex 35 was employed to afford the catalyst 44 as a green solid in 68% yield.

0.486 g (68%)—green solid; 1H (300 MHz, CDCl$_3$) δ ppm: 16.365-16.390 (bs, 1H), 7.070-7.055 (m, 4H), 6.983 (dd, 1H, J=3.0 Hz, J=8.7 Hz), 6.690 (d, 1H, J=8.7 Hz), 6.370 (d, 1H, J=3.0 Hz), 4.802 (heptet, 1H, J=6.3 Hz), 4.186 (s, 4H), 2.828 (s, 6H), 2.487-2.399 (m, 18H) 1.238 (d, 6H, J=6.3 Hz). $^{13}$C (75.4 MHz, CDCl$_3$) δ ppm: 298.5, 212.3, 146.9, 145.3, 145.1, 139.3, 138.7, 129.4, 115.4, 113.0, 108.3, 74.30, 53.51, 51.47, 41.86, 21.16, 21.09, 19.60. HRMS (ESI) calcd for $C_{33}H_{43}N_3OClRu$ ([M-Cl]$^+$) m/z 634.2138. found 634.2110. HRMS (ESI) calcd for $C_{33}H_{43}N_3OClRu$ ([M-Cl]$^+$) m/z 634.2138. found 634.2110.

Synthesis of Complex 45

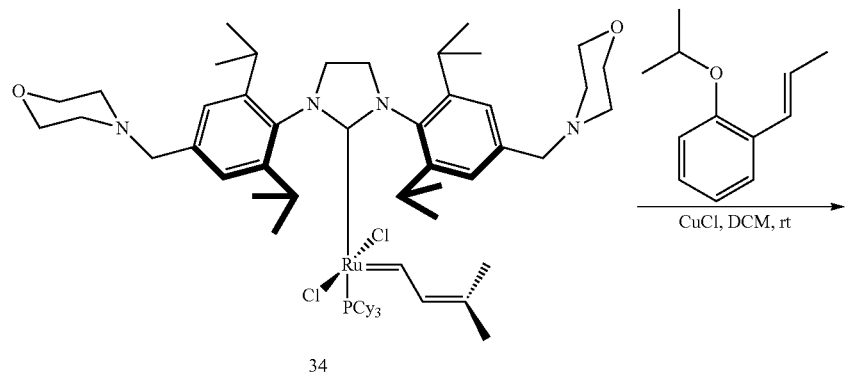

34

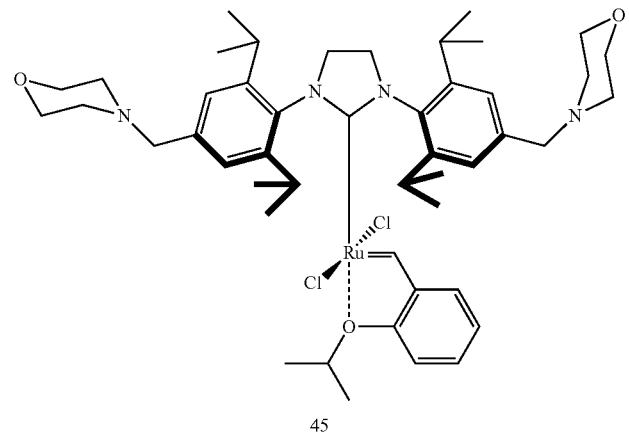

45

1-Isopropoxy-2-propenyl-benzene (0.175 g, 0.991 mmol) and CuCl (0.147 g, 1.486 mmol) were placed in a Schlenk flask. The flask was filled with argon and then dry dichloromethane (20 ml) was added. Afterwards complex 34 (1.10 g, 0.991 mmol) was added and the resulting solution was stirred at room temperature for 30 min. Solvent was evaporated, resulting material was dissolved in a minimum amount of EtOAc and the insoluble white solid filtered through a Pasteur pipette containing cotton wool. The solvent was concentrated again in vacuum, and the crude catalyst was purified by flash chromatography (c-hexane/EtOAc 7:3). Removal of solvents afforded product 45 (0.31 g, 34%) as a green solid.

$^1$H (300 MHz, CDCl$_3$) δ ppm: 16.493, (s, 1H), 7.470-7.412 (m, 1H), 7.309 (s, 4H), 6.811-6.776 (m, 3H), 4.910 (heptet, 1H, J=6.3 Hz), 4.164 (s, 4H), 3.780-3.750 (m, 8H), 3.643 (s, 4H) 3.622-3.533 (m, 4H), 2.562-2.531 (m, 8H), 1.344 (d, 6H, J=6.3 Hz), 1.259-1.237 (m, 24H). $^{13}$C (75.4 MHz, CDCl$_3$) ppm: 289.7, 213.7, 152.4, 149.0, 144.2, 138.9, 129.4, 125.2, 122.1, 113.1, 74.80, 67.14, 63.51, 54.62, 53.59, 28.80, 26.61, 23.41, 21.82. HRMS (ESI) calcd for C$_{47}$H$_{68}$N$_4$O$_3$ClRu ([M-Cl]$^+$) m/z 873.4023. found 873.4020.

Synthesis of Complex 46

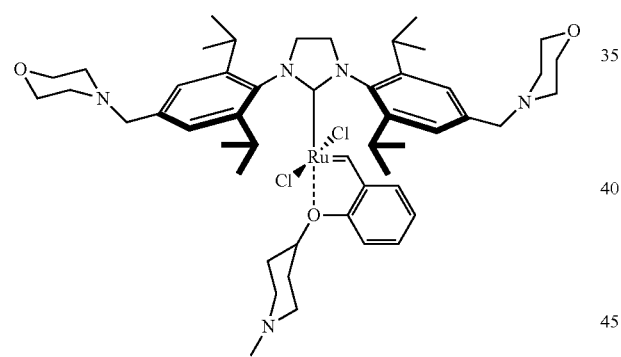

46

The same procedure as described for complex 45 was employed to afford the catalyst 46 as a green solid in 30% yield. Column chromatography was performed using c-hexane/EtOAc 1:1 mixture.

0.450 g (30%)—green solid; $^1$H (300 MHz, CDCl3) δ ppm: 16.490 (s, 1H), 7.450-7.393 (m, 1H), 7.311 (s, 4H), 6.792-6.764 (m, 3H), 4.550-4.380 (m, 1H), 4.160 (s, 4H), 3.790-3.760 (m, 8H), 3.637 (s, 4H), 3.613-3.548 (m, 4H), 2.534-2.554 (m, 8H), 2.188 (s, 3H), 2.133-1.859 (m, 8H), 1.245 (d, 24H, J=6.9 Hz). $^{13}$C (75.4 MHz, CDCl$_3$) δ ppm: 298.4, 213.5, 152.2, 149.0, 140.1, 139.0, 129.3, 125.0, 122.3, 122.2, 112.9, 79.10, 67.16, 63.47, 54.59, 53.67, 45.67, 30.69, 28.78, 26.65, 23.36. HRMS (ESI) calcd for C$_{50}$H$_{74}$N$_5$O$_3$Cl$_2$Ru ([M]$^+$) m/z 964.4212. found 964.4242.

Synthesis of Complex 47

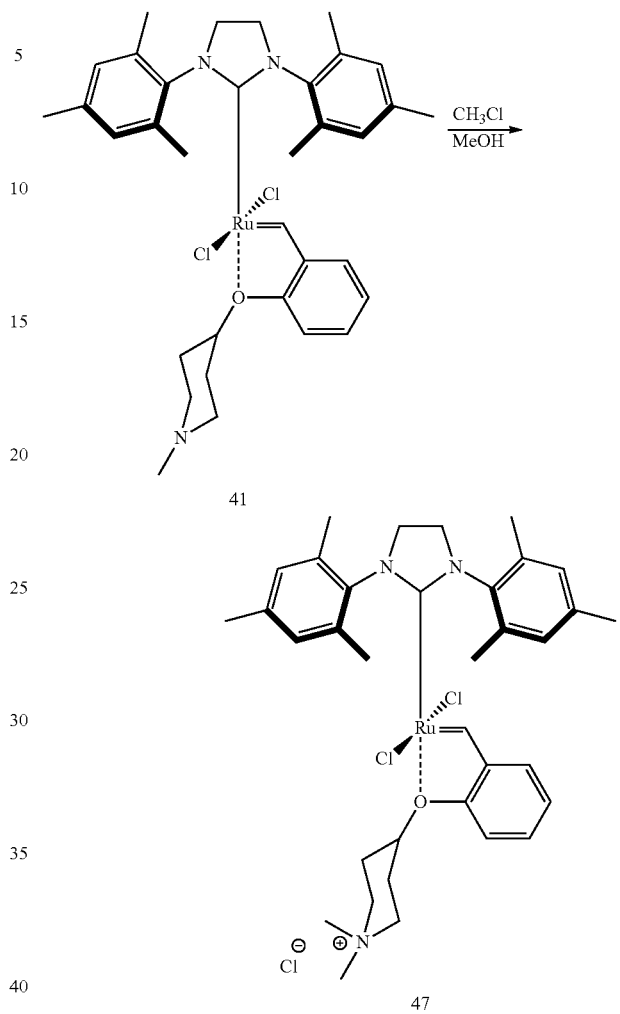

Complex 41 (0.224 g, 0.329 mmol) was placed under argon in pressure flask and dry methanol (3 ml) was added. Mixture was cooled to −30° C. and cold liquid chloromethane (ca 3 ml) was added. Mixture was slowly warmed to room temperature, then placed in oil bath heated to 50° C. and stirred for 60 h. After that time flask was opened carefully to remove chloromethane and mixture was concentrated. Residue was purified by filtration through a short plug of aluminium oxide (neutral, Brockman grade I, ethyl acetate/methanol 19:1). Solvents were evaporated, catalyst was washed with ethyl acetate twice and dried on vacuum to afford complex 47 (0.220 g, 91%) as a green solid.

Water solubility 2 mg/ml.

$^1$H (300 MHz, MeOD) δ ppm: 16.53 (s, 1H), 7.63-7.57 (m, 1H), 7.14-7.10 (m, 5H), 6.98-6.97 (m, 2H), 5.37-5.35 (m, 1H), 4.19 (s, 4H), 4.13-4.05 (m, 2H), 3.44 (s, 3H), 3.38-3.30 (m, 2H), 3.06 (s, 3H), 2.51-2.42 (m, 18H), 2.35-2.23 (m, 4H). $^{13}$C (75.4 MHz, MeOD) δ ppm: 296.6, 208.1, 150.7, 144.4, 139.0, 130.1, 129.6, 129.2, 122.3, 113.1, 72.27, 59.56, 52.98, 51.42, 24.58, 19.98, 18.13. HRMS (ESI) calcd for C$_{35}$H$_{46}$N$_3$OCl$_2$Ru ([M-Cl]$^+$) m/z 696.2061. found 696.2070.

$^1$H (300 MHz, CD$_2$Cl$_2$) δ ppm: 16.66 (s, 1H), 7.64-7.57 (m, 1H), 7.14-7.10 (m, 5H), 6.98-6.97 (m, 2H), 5.37-5.35 (m, 1H), 4.19 (s, 4H), 4.11-4.02 (m, 2H), 3.44 (s, 3H), 3.38-3.34 (m, 2H), 3.06 (s, 3H), 2.51-2.38 (m, 18H), 2.35-2.24 (m, 4H).

Synthesis of Complex 48

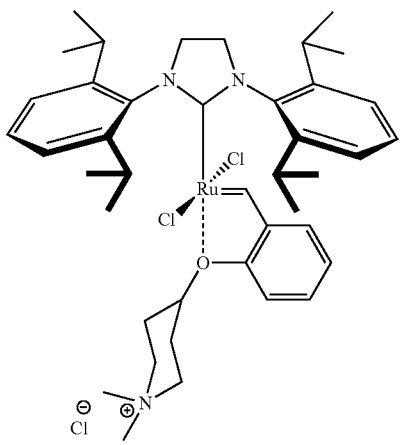

The same procedure as described for complex 47 was employed to afford the catalyst 48 as a green solid in 98% yield.

Insoluble in neat water, excellent solubility in methanol, ethanol and water/alcohol mixture.

0.208 g (98%)—green solid; $^1$H (300 MHz, CDCl$_3$) δ ppm: 16.381 (s, 1H), 7.594-7.264 (m, 7H), 6.986-6.832 (m, 3H), 5.370-5.084 (bs, 1H), 4.200 (s, 4H), 4.000-3.720 (bs, 3H), 3.700-3.250 (bs, 8H), 3.114-2.279 (bs, 3H), 2.543-2.100 (bs, 4H), 1.724-0.724 (m, 24H). $^{13}$C (75.4 MHz, CDCl$_3$) δ ppm: 291.2, 212.0, 151.0, 149.5, 143.3, 136.3, 130.4, 130.1, 124.5, 123.4, 122.9, 113.3, 72.08, 59.52, 54.57, 53.81, 50.71, 28.98, 26.63, 25.03, 23.30. HRMS (ESI) calcd for C$_{41}$H$_{58}$N$_3$OCl$_2$Ru ([M-Cl]$^+$) m/z 780.3000. found 780.3017.

Synthesis of Complex 49

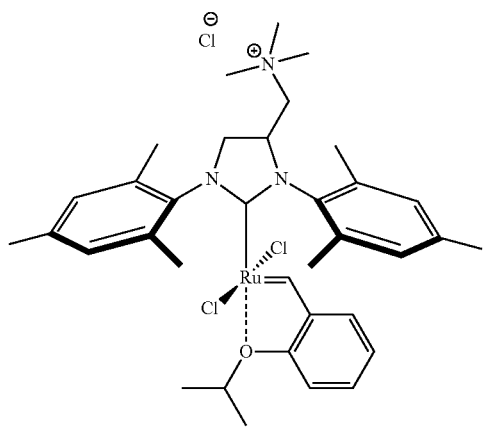

The same procedure as described for complex 47 was employed to afford the catalyst 49 as a green solid in 84% yield.

Water solubility 3 mg/ml.

0.218 g (84%)—green solid; $^1$H (300 MHz, CDCl$_3$) δ ppm: 16.375 (bs, 1H), 7.483-7.506 (m, 2H), 7.030-6.776 (d, 6H), 5.080-5.060 (bs, 1H), 4.875-4.840 (m, 1H), 4.660-4.640 (bs, 1H), 4.416-4.395 (bs, 1H), 4.230-4.180 (bs, 2H), 3.053-3.015 (bs, 9H), 2.393-2.376 (bs, 18H), 1.222-1.216 (m, 6H). $^{13}$C (75.4 MHz, CDCl$_3$) δ ppm: 298.5, 214.5, 152.4, 145.3, 139.8, 139.0, 130.1, 130.0, 129.5, 129.3, 122.9, 122.4, 113.0, 75.70, 45.88, 21.22, 21.11, 8.70. HRMS (ESI) calcd for C$_{36}$H$_{48}$N$_3$OCl$_2$Ru ([M-Cl]$^+$) m/z 698.2218. found 698.2237.

Synthesis of Complex 50

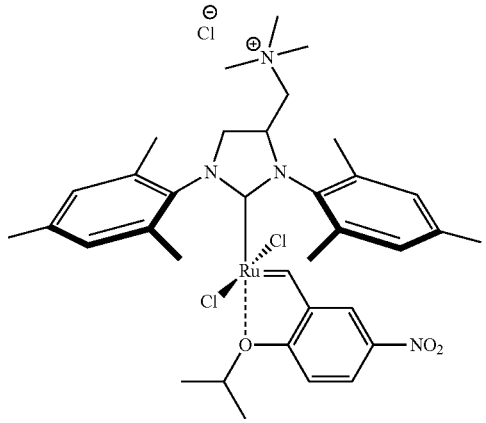

The same procedure as described for complex 47 was employed to afford the catalyst 50 as a green solid in 64% yield.

Water solubility 3 mg/ml.

0.165 g (64%)—green solid; $^1$H (300 MHz, CDCl$_3$) δ ppm: 16.255 (s, 1H), 8.425 (dd, J=1.8 Hz, J=9.0 Hz, 1H), 7.754 (d, J=1.8 Hz, 1H), 7.120-6.884 (m, 5H), 5.350-5.100 (m, 1H), 5.010-4.928 (m, 1H), 4.855-4.750 (m, 1H), 4.600-4.400 (m, 1H), 3.520-3.435 (m, 2H), 3.325 (s, 9H), 2.573-2.186 (m, 18H), 1.276-1.2746 (m, 6H). HRMS (ESI) calcd for C$_{35}$H$_{47}$N$_4$O$_3$Cl$_2$Ru ([M-Cl]$^+$) m/z 743.2069. found 743.2091. $^1$H (300 MHz, CD$_2$Cl$_2$) δ ppm: 16.26 (s, 1H), 8.47 (dd, J=2.4 Hz, J=9.0 Hz, 1H), 7.78 (d, J=2.4 Hz, 1H), 7.13-6.96 (m, 5H), 5.32-5.21 (m, 1H), 5.00 (heptet, J=6.0 Hz, 1H), 4.87-4.81 (m, 1H), 4.62-4.47 (m, 2H), 3.31 (s, 9H), 3.13 (d, J=12.6 Hz, 1H), 2.45 (bs, 18H), 1.28-1.25 (m, 6H). $^{13}$C (75.4 MHz, CD$_2$Cl$_2$) δ ppm: 291.1, 211.1, 156.3, 144.5, 143.1, 140.2, 139.7, 139.6, 130.6, 130.0, 129.5, 124.5, 117.0, 113.0, 78.0, 68.0, 58.6, 21.0, 20.9. IR (KBr) ν 3402, 2977, 2920, 1605, 1575, 1520, 1478, 1381, 1341, 1292, 1134, 1092, 948, 916, 855, 828, 746, 657.

Synthesis of Complex 51

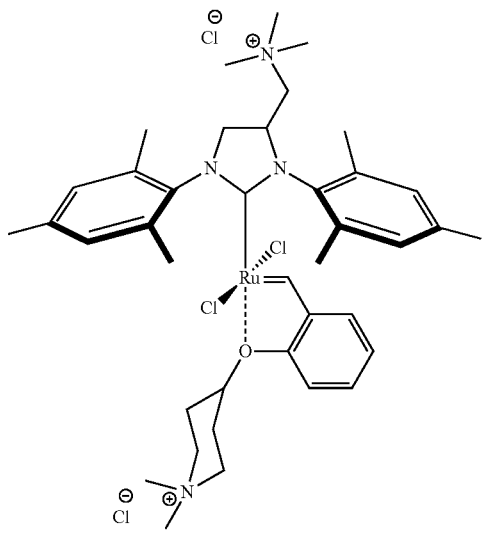

The same procedure as described for complex 47 was employed to afford the catalyst 51 as a green solid in 95% yield.

Water solubility 35 mg/ml.

0.220 g (95%)—green solid; $^1$H (300 MHz, MeOD) δ ppm: 16.404-16.435 (bs, 1H), 7.692-7.641 (m, 1H), 7.203-7.149 (m, 5H), 7.051-7.002 (m, 1H), 6.933-6.908 (m, 1H), 5.239-5.068 (m, 1H), 4.868 (s, 4H), 4.665 (tr, 1H, J=10.2 Hz), 4.370 (tr, 1H, J=10.5 Hz), 4.172-4.062 (m, 1H), 3.459-3.348 (m, 2H), 3.230 (bs, 3H), 3.156 (s, 9H), 3.052 (s, 3H), 2.520-2.473 (m, 18H), 2.432-2.226 (m, 4H). $^{13}$C (75.4 MHz, MeOD) δ ppm: 297.3, 212.8, 150.8, 144.43, 140.1, 139.6, 130.6, 130.5, 130.0, 129.4, 129.3, 123.3, 122.4, 113.2, 72.67, 67.43, 59.98, 58.43, 53.76, 52.89, 24.79, 24.70, 20.01, 13.10. LRMS (ESI) calcd for $C_{39}H_{56}N_4OCl_2Ru$ ($[M-2Cl]^{2+}$) m/z 384.1. found 384.2.

Synthesis of Complex 52

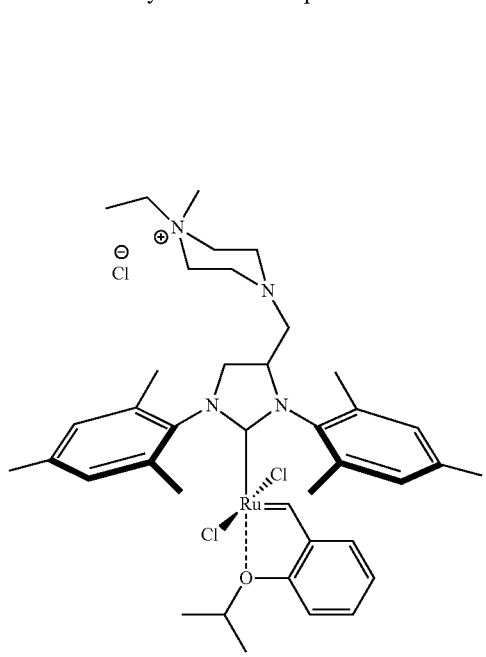

The same procedure as described for complex 47 was employed to afford the catalyst 52 as a green solid in 97% yield.

Water solubility 3 mg/ml.

0.290 g (97%)—green solid; $^1$H (300 MHz, CDCl$_3$) δ ppm 16.44 (s, 1H), 7.60-7.54 (m, 1H), 7.10-7.08 (m, 4H), 6.97-6.84 (m, 3H), 4.89 (heptet, 1H, J=6.0 Hz), 4.70-4.59 (m, 1H), 4.35-4.28 (m, 1H), 3.95-3.88 (m, 1H), 3.78-3.71 (m, 2H), 3.60-3.56 (m, 2H), 3.35-3.22 (m, 5H), 2.86-2.83 (m, 2H), 2.79-2.72 (m, 2H), 2.43-2.36 (m, 18H), 1.35 (t, 3H, J=7.1 Hz), 1.23 (d, 6H, J=6.0 Hz). $^{13}$C (75.4 MHz, CDCl$_3$) δ ppm: 298.4, 214.2, 152.3, 145.3, 139.0, 138.1, 130.0, 129.9, 129.4, 122.8, 122.4, 113.0, 75.05, 60.45, 59.50 59.40, 46.90, 31.01, 22.68, 21.13, 14.16, 7.84. HRMS (ESI) calcd for $C_{39}H_5N_4OCl_2Ru$ ($[M-Cl]^+$) m/z 767.2796. found 767.2802.

$^1$H NMR (600 MHz, CD$_2$CL$_2$) δ ppm: 16.44 (s, 1H), 7.58-7.55 (m, 1H), 7.10-7.07 (m, 4H), 6.96-6.91 (m, 2H) 6.84 (d, 1H, J=7.8 Hz), 4.89 (heptet, 1H, J=6.0 Hz), 4.67-4.62 (m, 1H), 4.31 (pseudot, 1H, J=10.2 Hz), 3.91 (pseudot, 1H, J=9.6 Hz), 3.70-3.67 (m, 2H, NCH$_2$CH$_3$), 3.52 (bs, 2H), 3.29-3.23 (m, 5H), 2.85-2.79 (m, 4H), 2.79-2.74-2.69 (m, 2H), 2.42-2.27 (m, 18H), 1.34 (t, 3H, J=6.6 Hz, NCH$_2$CH$_3$), 1.22 (d, 6H, J=6.0 Hz).

Synthesis of Complex 53

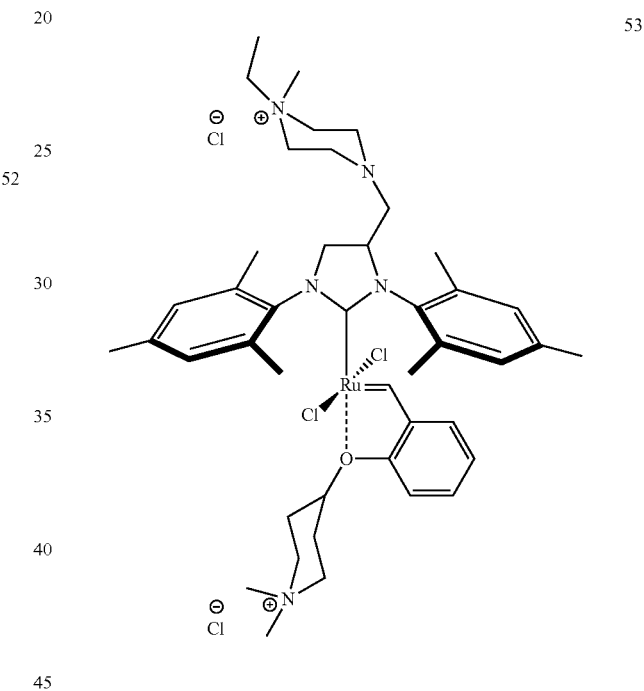

The same procedure as described for complex 47 was employed to afford the catalyst 53 as a green solid in 93% yield.

Water solubility 35 mg/ml.

0.370 g (93%)—green solid: $^1$H (300 MHz, MeOD) δ ppm: 16.590 (s, 1H), 7.670-7.632 (m, 1H), 7.200-7.122 (m, 5H), 7.013 (tr, 1H, J=7.5 Hz), 6.940-6.915 (m, 1H), 5.032 (m, 1H), 4.860 (s, 4H), 4.700-4.860 (m, 1H), 4.383 (tr, 1H, J=10.5 Hz), 4.00-4.020 (m, 1H), 3.442-3.418 (m, 6H), 3.202 (s, 3H), 3.0310-3.019 (m, 6H), 2.871-2.462 (m, 6H), 2.464-2.011 (m, 22H), 1.334 (tr, 3H, J=6.9 Hz). $^{13}$C (75.4 MHz, MeOD) δ ppm: 297.2, 211.0, 150.7, 144.5, 139.5, 139.2, 139.0, 130.3, 129.3, 123.3, 122.4, 113.1, 72.37, 61.23, 59.80, 59.73, 59.56, 53.30, 24.77, 24.62, 27.03, 19.96. LRMS (ESI) calcd for $C_{43}H_{63}N_5OCl_2Ru$ ($[M-2Cl]^{2+}$) m/z 418.7. found 418.6.

Synthesis of Complex 54

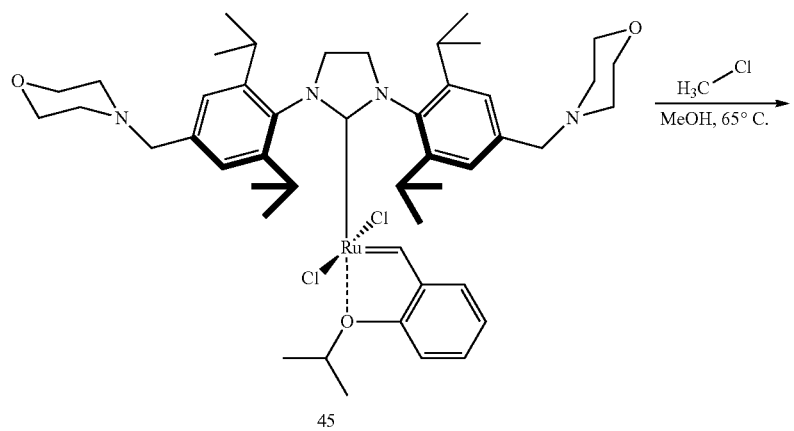

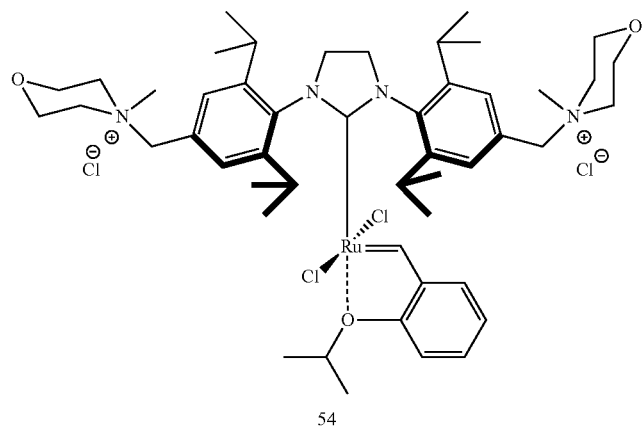

Complex 45 (0.224 g, 0.329 mmol) was placed under argon in pressure flask and dry methanol (3 ml) was added. Mixture was cooled to −30° C. and cold liquid chloromethane (ca 3 ml) was added. Mixture was slowly warmed to room temperature, then placed in oil bath heated to 65° C. and stirred for 72 h. After that time flask was opened carefully to remove chloromethane and mixture was concentrated. The residue was purified by filtration through a short plug of aluminium oxide (neutral, Brockman grade I, ethyl acetate/methanol 19:1). Solvents were evaporated, catalyst was washed with ethyl acetate twice and dried on vacuum to afford complex 54 (0.220 g, 91%) as a green solid.

Water solubility 2 mg/ml.

$^1$H (300 MHz, MeOD) δ ppm: 16.577 (s, 1H), 7.653-7.546 (m, 5H), 7.065-7.021 (m, 1H), 6.924-6.875 (m, 1H), 6.820-6.764 (m, 1H), 5.021 (sep, 1H, J=6.3 Hz), 4.380-4.020 (m, 12H), 3.917-3.884 (m, 3H), 3.734-3.436 (m, 11H), 3.281-3.175 (m, 8H), 1.413 (d, 6H, J=6.6 Hz), 1.373-1.237 (m, 24H). $^{13}$C (75.4 MHz, MeOD) δ ppm: 289.2, 212.6, 152.5, 151.0, 150.6, 149.3, 143.8, 143.7, 139.1, 138.7, 137.6, 130.0, 129.9, 129.4, 129.0, 128.2, 128.0, 126.8, 122.1, 122.0, 121.7, 113.2, 113.1, 74.9, 74.8, 69.2, 65.0, 61.5, 60.2, 59.2, 55.1, 54.7, 54.3, 52.3, 46.5, 29.1, 28.8, 28.5, 25.8, 25.4, 25.0, 22.6, 22.3, 22.0, 21.2, 7.85. LRMS (ESI) calcd for $C_{49}H_{74}N_4O_3Cl_2Ru$ ([M-2Cl]$^{2+}$) m/z 469.2. found 469.2.

Synthesis of Complex 55

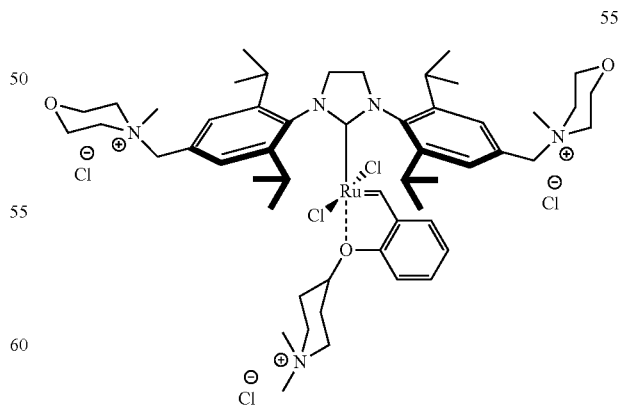

The same procedure as described for complex 54 was employed to afford the catalyst 55 as a green solid in 95% yield.

Water solubility 65 mg/ml.

0.425 g (95%)—green solid; $^1$H (300 MHz, MeOD) δ ppm: 16.534 (s, 1H), 7.711 (s, 4H), 7.661-7.609 (m, 1H), 7.211-7.183 (s, 1H), 7.025-6.975 (m, 1H), 6.881-6.842 (m, 1H), 5.171-5.050 (bs, 1H), 4.970 (s, 2H), 4.874 (s, 4H), 4.229-4.283 (m, 4H), 4.140-4.109 (m, 9H), 3.747-3.582 (m, 9H), 3.508-3.460 (m, 4H), 3.347-3.262 (m, 4H), 3.065-3.043 (m, 3H), 2.348-2.261 (m, 4H), 2.012 (s, 3H), 1.342-1.213 (m, 26H). $^{13}$C (75.4 MHz, MeOD) δ ppm: 287.8, 211.3, 150.7, 150.0 143.2, 138.8, 130.4, 130.3, 129.4, 128.6, 127.5, 123.3, 122.2, 113.3, 72.82, 69.10, 60.3, 60.16, 60.09, 55.39, 54.86, 45.21, 28.91, 25.49, 25.41, 22.46, 22.27, 13.10. LRMS (ESI) calcd for $C_{53}H_{82}N_5O_3Cl_2Ru$ ([M-3Cl]$^{3+}$) m/z 336.1. found 336.1.

Synthesis of Complex 56

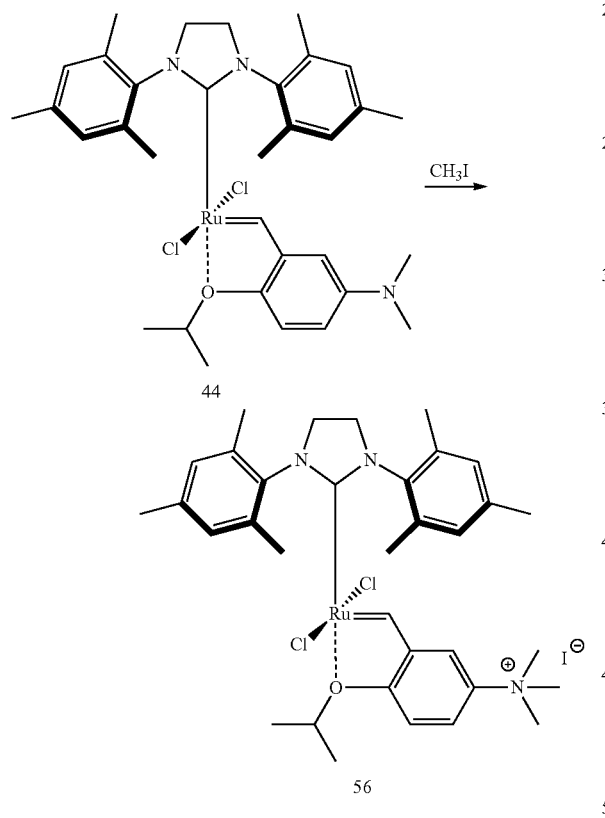

Complex 44 (0.441 g, 0.658 mmol) was placed under argon in a Shlenk flask and iodomethane (8.19 ml, 132 mmol) was added. Mixture was stirred at room temperature for 5 h. Ethyl acetate was added to a reaction mixture and crude product was filtered off. Next complex was washed with ethyl acetate twice then precipitated from dichloromethane/ethyl acetate mixture, filtered and dried on vacuum to afford 56 (491 mg, 92%) as a green solid.

Water solubility 1 mg/ml.

$^1$H (300 MHz, CDCl$_3$) δ ppm: 16.386 (s, 1H), 7.050-7.066 (m, 7H), 4.912 (heptet, 1H, J=6 Hz), 4.204 (s, 4H), 3.892 (s, 9H), 2.448-2.389 (m, 18H), 1.232 (d, 6H, J=6 Hz). $^{13}$C (75.4 MHz, CDCl$_3$) δ ppm: 289.4, 207.9, 152.5, 144.2, 141.9, 139.1, 138.7, 129.5, 122.1, 115.5, 112.1, 57.99, 51.20, 21.58, 21.54, 21.21, 21.04. LRMS (ESI) calcd for $C_{34}H_{46}N_3OCl_2Ru$ ([M-I]$^+$) m/z 684.2. found 684.2.

Synthesis of Complex 57

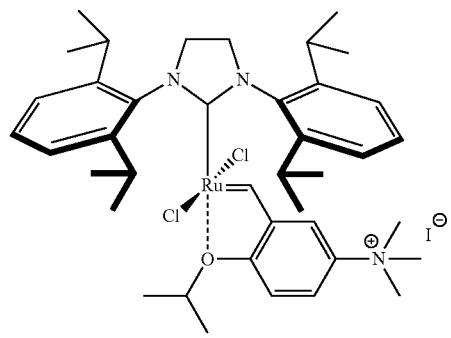

The same procedure as described for complex 56 was employed to afford the catalyst 57 as a green solid in 84% yield.

0.100 g (84%)—green solid; $^1$H (300 MHz, CD$_2$Cl$_2$) δ ppm: 16.181 (s, 1H), 8.491 (dd, 1H, J=9.3 Hz, J=2.4 Hz), 7.589-7.538 (m, 2H), 7.400-7.373 (m, 4H), 7.055 (d, 1H, J=9.3 Hz), 6.889 (d, 1H, J=2.4 Hz), 4.946 (heptet, 1H, J=6.0 Hz), 4.208-4.216 (m, 4H), 3.722-3.875 (bs, 9H), 3.553-3.490 (m, 4H), 1.332 (d, 6H, J=6.0 Hz), 1.265-1.242 (m, 24H). $^{13}$C (75.4 MHz, CD$_2$Cl$_2$) δ ppm: 282.0, 210.1, 152.8, 149.2, 143.7, 141.8, 136.3, 129.9, 124.8, 124.5, 121.2, 115.1, 111.2, 57.86, 54.52, 28.89, 26.62, 23.42, 21.67. HRMS (ESI) calcd for $C_{40}H_{58}N_3OCl_2Ru$ ([M-I]$^+$) m/z 768.3000. found 768.2995.

Synthesis of Complex 58

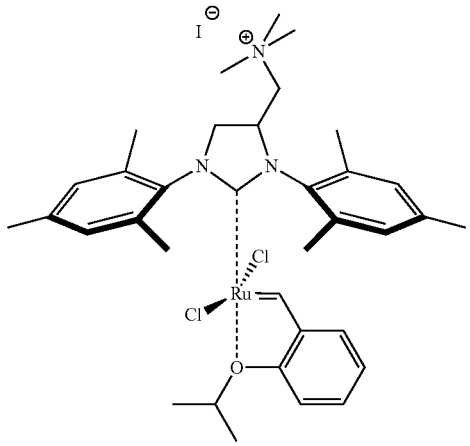

The same procedure as described for complex 56 was employed to afford the catalyst 58 as a green solid in 98% yield.

0.138 g (98%)—green solid; $^1$H (300 MHz, CDCl$_3$) δ ppm: 16.356 (s, 1H), 7.506-7.494 (m, 1H), 7.115-6.757 (m, 7H), 5.220-5.030 (bs, 1H), 4.865-4.820 (m, 1H), 4.704-4.680 (m, 1H), 4.500-4.400 (bs, 1H), 3.393-2.951 (m, 11H), 2.640-2.169 (m, 18H), 1.234-1.190 (m, 6H). $^{13}$C (75.4 MHz, CDCl$_3$) δ ppm: 298.5, 214.4, 152.4, 145.2, 139.9, 139.2, 138.6, 131.6, 130.2, 129.5, 128.7, 128.5, 126.5, 122.8, 122.8, 113.1, 75.27, 67.95, 58.30, 54.31, 22.04, 21.10, 19.10, 14.2. HRMS (ESI) calc for $C_{35}H_{48}N_3OCl_2Ru$ ([M-I]$^+$) m/z 698.2218. found 698.2228.

$^1$H (300 MHz, CD$_2$Cl$_2$) δ ppm: 16.33 (s, 1H), 7.61-7.53 (m, 1H), 7.13-7.05 (m, 4H), 6.94-6.92 (d, J=4.5 Hz, 2H), 6.87-6.84 (d, J=8.4 Hz, 2H), 5.26-5.15 (m, 1H), 4.88 (heptet, J=6.0

Hz, 1H), 4.81-4.74 (m, 1H), 4.63-4.50 (bs, 2H), 3.24 (s, 9H), 3.10 (d, J=12.3 Hz, 1H), 2.43 (bs, 18H), 1.21 (dd, J=2.4 Hz, J=6.0 Hz 6H). $^{13}$C (75.4 MHz, CD$_2$Cl$_2$) δ ppm: 296.9, 214.0, 152.2, 145.1, 139.9, 139.7, 139.3, 130.6, 130.1, 129.5, 129.3, 122.5, 122.4, 113.1, 75.4, 67.7, 58.3, 20.9.

56.98, 46.74, 46.58, 20.91, 7.740. HRMS (ESI) calcd for C$_{39}$H$_{55}$N$_4$OCl$_2$Ru ([M-I]$^+$) m/z 767.2796. found 767.2792.

Synthesis of Complex 59

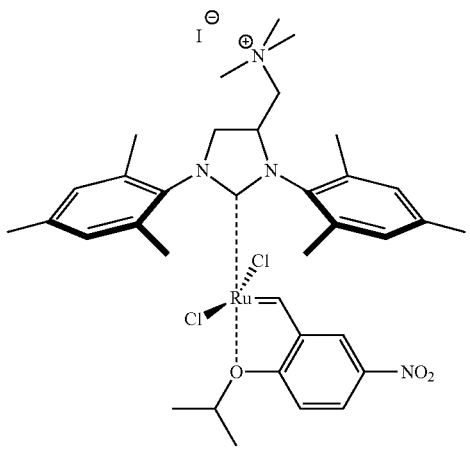

59

The same procedure as described for complex 56 was employed to afford the catalyst 59 as a green solid in 86% yield.

0.045 g (86%)—green solid; LRMS (ESI) calcd for C$_{35}$H$_{47}$Cl$_2$N$_4$O$_3$Ru ([M-I]$^+$) m/z 743.2. found 743.1. IR (KBr) ν 3434, 2980, 2919, 1605, 1576, 1521, 1478, 1421, 1379, 1343, 1344, 1197, 1136, 1094, 1013, 950, 917, 857, 829, 745, 658.

Synthesis of Complex 60

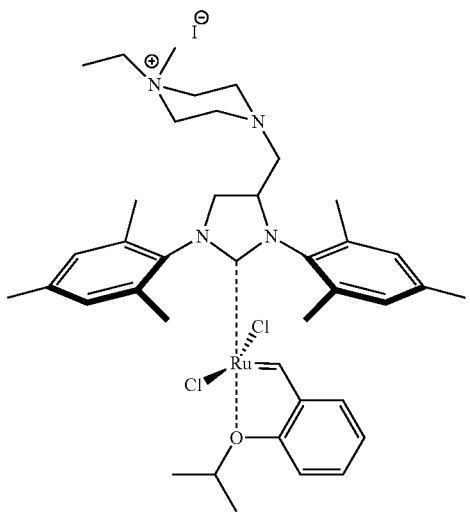

60

The same procedure as described for complex 56 was employed to afford the catalyst 60 as a green solid in 85% yield.

0.385 g (85%)—green solid $^1$H (300 MHz, CD$_2$Cl$_2$) δ ppm: 16.443 (s, 1H), 7.504-7.446 (m, 1H), 7.108-6.741 (m, 7H), 4.893 (heptet, 1H, J=6.0 Hz), 4.677-4.598 (m, 1H), 4.338 (tr, 1H, 10.8 Hz), 3.947-3.882 (m, 1H), 3.676-3.204 (m, 6H), 3.204 (s, 3H), 2.903-2.689 (m, 6H) 2.415-2.440 (m, 18H), 1.321-1.266, (m, 3H), 1.247-1.417 (m, 6H). $^{13}$C (75.4 MHz, CD$_2$Cl$_2$) δ ppm: 296.6, 213.6, 152.0, 145.2, 139.9, 129.9, 129.7, 129.4, 122.4, 122.3, 113.0, 60.72, 60.18, 60.00,

Synthesis of Complex 61

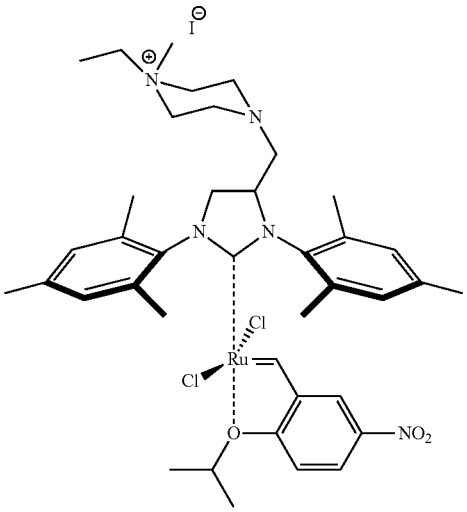

61

The same procedure as described for complex 56 was employed to afford the catalyst 61 as a green solid in 85% yield.

0.180 g (85%)—green solid; $^1$H (300 MHz, CDCl$_3$) δ ppm: 16.360 (s, 1H), 8.452-8.386 (m, 1H), 7.770-7.612 (m, 1H), 7.152-6.876 (m, 5H), 5.001-4.940 (m, 1H) 4.753-4.500 (m, 1H) 4.450-4.200 (m, 1H), 3.931-3.870 (m, 1H), 3.656-3.383 (m, 4H), 3.380-2.990 (m, 5H), 2.850-2.765 (m, 5H) 2.418-2.030 (m, 19H), 1.335-1.270 (m, 9H). $^{13}$C (75.4 MHz, CDCl$_3$) δ ppm: 292.3, 156.4, 144.6, 143.1, 139.4, 139.2, 130.6, 130.2, 129.5, 124.7, 124.4, 117.4, 112.9, 76.7, 67.27, 60.8, 60.3, 60.02, 47.65, 46.83, 31.60, 22.66, 21.83, 21.57, 21.11, 14.13. HRMS (ESI) calcd for C$_{39}$H$_4$N$_5$O$_3$Cl$_2$Ru ([M-I]$^+$) m/z 812.2647. found 812.2655.

Synthesis of Complex 62

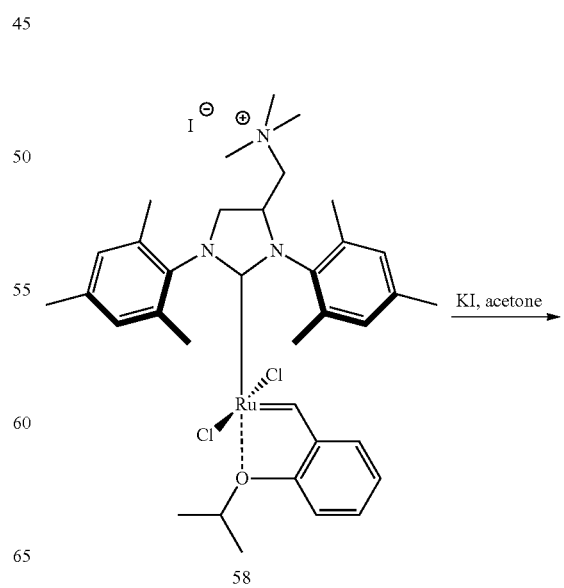

58

-continued

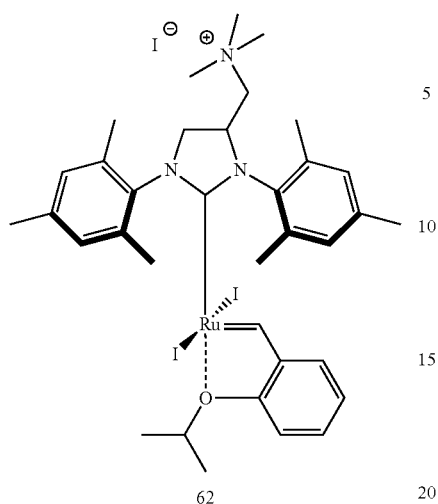

62

Potassium iodide (0.723 g, 4.35 mmol) was added to a solution of complex 58 (0.120 g, 0.145 mmol) in acetone (5 ml). Mixture was stirred for 1 h and then solvent was evaporated. Catalyst was dissolved in dichloromethane (10 ml) and insoluble material was filtered off. Dichloromethane was evaporated to dryness and above procedure was repeated 3 times. Product was dried on vacuum. Complex 62 was obtained as a dark green solid (0.130 g, 89%). Product was obtained as a mixture of rotamers.

$^1$H (300 MHz, CDCl$_3$) δ ppm: 15.488-15.328 (m, 1H), 7.564-7.515 (m, 1H), 7.114-6.816 (m, 7H), 5.090-4.973 (m, 2H), 4.743-4.703 (m, 1H), 4.482-4.395 (m, 1H), 3.357 (s, 9H), 3.200-3.0924 (m, 2H), 2.756-2.166 (m, 18H), 1.502-1.254 (m, 6H). $^{13}$C (75.4 MHz, CDCl$_3$) δ ppm: 299.7, 217.8, 216.8, 153.3, 153.1, 145.3, 144.9, 140.0, 139.9, 139.7, 139.2, 138.4, 138.2, 137.7, 137.5, 136.7, 134.6, 132.8, 131.5, 131.3, 131.1, 130.4, 130.1, 129.6, 123.4, 122.0, 113.5, 75.95, 68.6, 67.88, 67.26, 59.71, 58.3, 57.9, 54.4, 25.53, 25.07, 21.90, 21.8, 21.68, 21.52, 21.4, 21.3, 20.80. HRMS (ESI) calcd for C$_{35}$H$_{48}$N$_3$ORuI$_2$ ([M-I]$^+$) m/z 882.0930. found 882.0958.

Synthesis of Complex 64

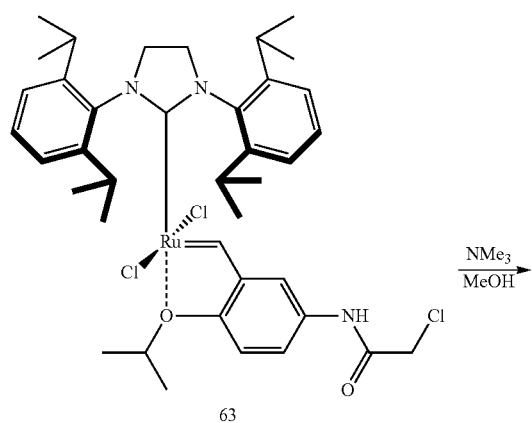

63

-continued

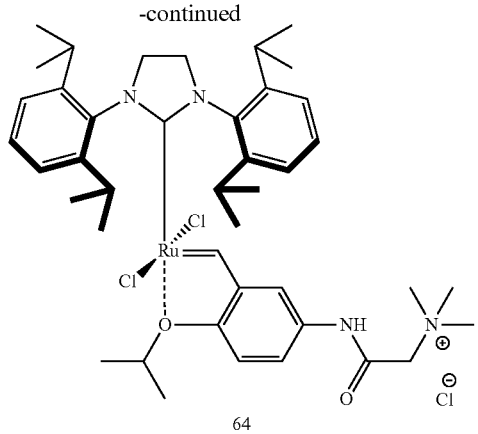

64

Complex 63 (0.224 g, 0.329 mmol) was placed under argon in pressure flask and dry methanol (3 ml) was added. Mixture was cooled to −10° C. and cold trimethylamine (33% wt in methanol, 3 ml) was added. Mixture was slowly warmed to room temperature, then placed in oil bath heated to 50° C. and stirred for 60 h. Reaction mixture was concentrated and the residue was filtered through a short pad of aluminium oxide (neutral, Brockman grade I, ethyl acetate/methanol 19:1). Solvents were evaporated, catalyst was washed with ethyl acetate twice and dried on vacuum to afford 64 (0.220 g, 91%) as a green solid.

$^1$H (300 MHz, CD$_2$Cl$_2$) δ ppm: 16.240 (s, 1H), 11.550-11.350 (bs, 1H) 7.872-7.846 (m, 1H), 7.626 (m, 2H), 7.414-7.389 (m, 5H) 6.808-6.780 (m, 1H), 4.897-4.856 (m, 1H), 4.762-4.600 (m, 2H), 4.202 (s, 4H), 3.594-3.550 (m, 4H), 3.353 (s, 9H), 1.326-1.220 (m, 30H).

Synthesis of Compound 66

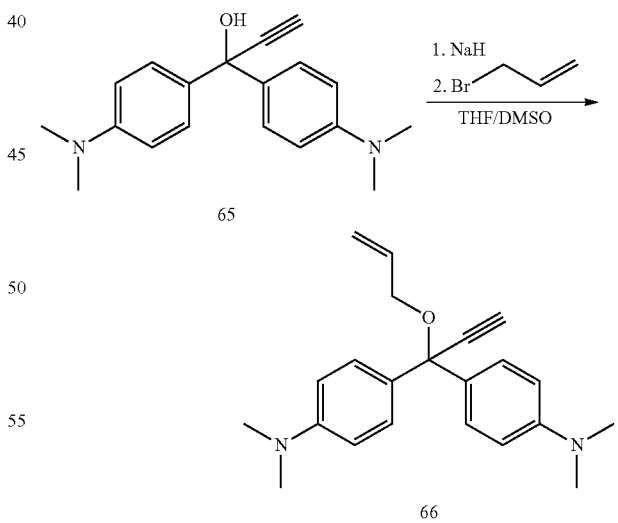

NaH (15 mg, 0.374 mmol) was added at −10° C. to a solution of 65 (100 mg, 0.340 mmol) in THF/DMSO mixture (9/1, 4 ml). Reaction mixture was warmed to room temperature and stirred for 1 h. Then it was cooled down to −10° C. and allyl bromide (0,044 ml, 0.510 mmol) was added in one portion. After that, mixture was stirred at room temperature for 1 h. Solvents were evaporated and crude product was purified by column chromatography (c-hexane/EtOAc/Et₃N 8/2/0.1). Solvents were removed to afford 66 (103 mg, 91%) as a light-yellow oil.

¹H (300 MHz, CDCl₃) δ ppm: 7.422-7.392 (m, 4H), 6.701-6.650 (m, 4H), 6.045-5.935 (m, 1H), 5.389-5.319 (m, 1H), 5.159-5.118 (m, 1H), 4.036-4.008 (m, 2H), 2.936 (s, 12H), 2.827 (s, 1H).

Synthesis of Compound 67

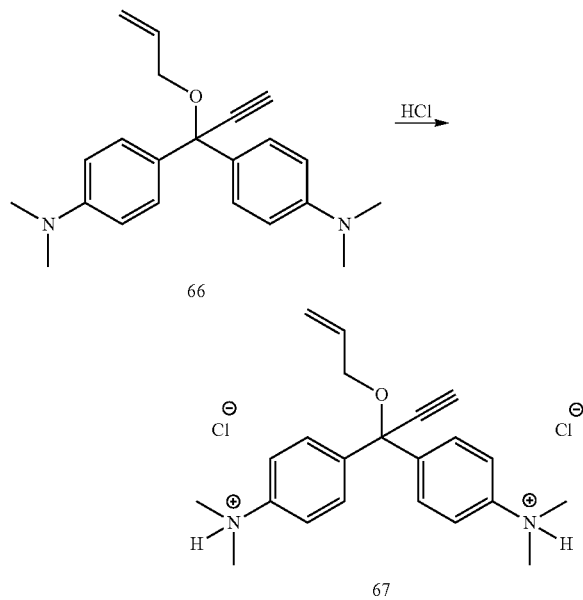

HCl (1M in Et₂O, 0.625 ml) was added at 0° C. to a solution of 66 (102 mg, 0.305 mmol) in Et₂O (4 ml). White solid was filtered, washed with Et₂O (2×5 ml) and dried on vacuum to afford 67 (114 mg, 92%) as a green solid (product changed from white to green during work up).

¹H (300 MHz, D₂O) δ ppm: 7.772-7.742 (m, 4H), 7.533-7.503 (m, 4H), 5.988-5.896 (m, 1H), 5.357-5.163 (m, 2H), 4.027-3.999 (m, 2H), 3.475 (s, 1H), 3.172 (s, 12H).

EXAMPLE 1

Ring Closing Metathesis of 2,2-Diallyl-Malonic Acid Diethyl Ester

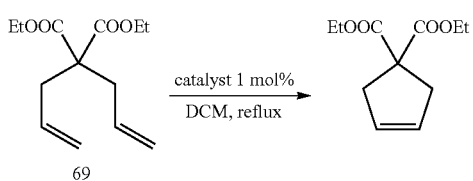

Appropriate amount of catalyst (1 mol %) was added under argon to a solution 69 (165 mg, 0.69 mmol) in dry, degased dichloromethane. Reaction mixture was stirred at reflux, progress of the reaction was monitored using GC method. After completion of the reaction, mixture was filtered through a pad of silica gel. Weight of silica gel used was two hundred times greater than the weight of the catalyst. Product was removed from silica gel with additional amount of dichloromethane. In all cases product was isolated with quantitative yield. GC purity and Ru content (using ICP MS method) was determined.

| Entry | Catalyst | Time [min] | GC purity [%] | Ru [ppm] |
|---|---|---|---|---|
| 1 | B | 30 | 99 | 2180 |
| 2 | 57 | 30 | 95 | 73 |
| 3 | 58 | 240 | 97 | 3.8 |
| 4 | 59 | 60 | 98 | 2.6 |
| 5 | 60 | 240 | 99 | 3.1 |

EXAMPLE 2

Ring Closing Metathesis of 2-Allyl-2-(2-Methyl-Allyl)-Malonic Acid Diethyl Ester

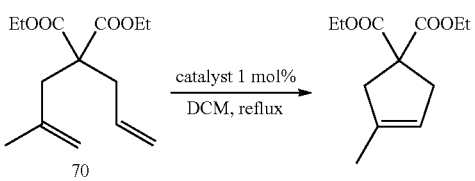 [SMILES: C=CCC(CC(=C)C)(C(=O)OCC)C(=O)OCC ; CCOC(=O)C1(C(=O)OCC)CC=C(C)C1]

Appropriate amount of catalyst (1 mol %) was added under argon to a solution of 70 (196 mg, 0.77 mmol) in dry, degased dichloromethane. Reaction mixture was stirred at reflux, progress of the reaction was monitored using GC method. After completion of the reaction, mixture was filtered through a pad of silica gel. Weight of silica gel used was two hundred times greater than the weight of the catalyst. Product was removed from silica gel with additional amount of dichloromethane. In all cases product was isolated with quantitative yield. GC purity and Ru content (using ICP MS method) was determined.

| Entry | Catalyst | Time [min] | GC purity [%] | Ru [ppm] |
|---|---|---|---|---|
| 1 | A | 120 | 94 | 3640 |
| 2 | A | 120 | 97 | 658[a] |
| 3 | A | 120 | 89 | 293[b] |
| 4 | B | 50 | 98 | 1950 |
| 9 | 50 | 120 | 98 | 11[c] |
| 5 | 57 | 60 | 92 | 55 |
| 6 | 58 | 600 | 91 | 0.89 |
| 7 | 58 | 600 | 91 | 9[d] |
| 8 | 59 | 300 | 97 | 1 |
| 10 | 60 | 600 | 92 | 2.1 |
| 11 | 61 | 300 | 95 | 1.8 |
| 12 | 62 | 600 | 80 | ND |

[a] result obtained with commercially available scavenger: SiliaBond Thiol, using protocol recommended by SILICYCLE
[b] result obtained with commercially available scavenger: SiliaBond DMT, using protocol recommended by SILICYCLE
[c] reaction mixture was washed with water five times
[d] product purification: silica gel was added to the reaction mixture and this was stirred for 10 min; after that reaction mixture was filtered through a Schott funnel.

EXAMPLE 3

Alken-Alkyn Ring Closing Metathesis

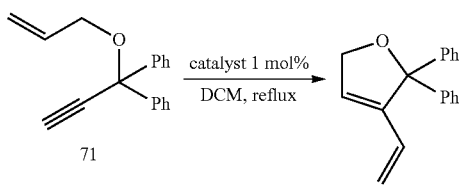 [SMILES: C#CC(OCC=C)(c1ccccc1)c1ccccc1 ; C=CC1=CCOC1(c1ccccc1)c1ccccc1]

Appropriate amount of catalyst (1 mol %) was added under argon to a solution of 71 (196 mg, 0.77 mmol) in dry, degased dichloromethane. Reaction mixture was stirred at reflux, progress of the reaction was monitored using GC method. After completion of the reaction, mixture was filtered through a pad of silica gel. Weight of silica gel used was two hundred times greater than the weight of the catalyst. Product was removed from silica gel with additional amount of dichloromethane. In all cases product was isolated with quantitative yield. GC purity and Ru content (using ICP MS method) was determined.

| Entry | Catalyst | Time [min] | GC purity [%] | Ru [ppm] |
|---|---|---|---|---|
| 1 | B | 15 | >99.5 | 1430 |
| 2 | 57 | 15 | >99.5 | 74 |
| 3 | 58 | 80 | 96.2 | 9.2 |
| 4 | 59 | 30 | >99.5 | 7.8 |
| 5 | 60 | 80 | 97.5 | 3.8 |

EXAMPLE 4

Cross Metathesis

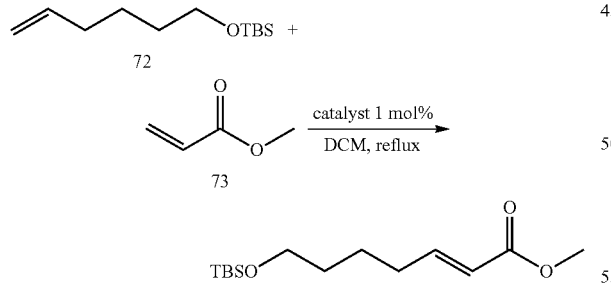

Appropriate amount of catalyst (1 mol %) was added under argon to a solution of 72 and 73 (196 mg, 0.77 mmol) in dry, degased dichloromethane. Reaction mixture was stirred at reflux, progress of the reaction was monitored using GC method. After completion of the reaction, mixture was filtered through a pad of silica gel. Weight of silica gel used was two hundred times greater than the weight of the catalyst. Product was removed from silica gel with additional amount of dichloromethane. GC purity and Ru content (using ICP MS method) was determined.

| Entry | Catalyst | Time [min] | GC purity [%] | E/Z | Yield [%] | Ru [ppm] |
|---|---|---|---|---|---|---|
| 1 | A | 40 | 56.5[c] | 21/1 | 87 | 2550 |
| 2 | A | 40 | 95 | 21/1 | 89 | 1310[a] |
| 3 | A | 40 | 91 | 19/1 | 99 | 109[b] |
| 4 | B | 15 | 99 | 17/1 | 94 | 704 |
| 5 | 49 | 80 | 92 | 16/1 | 93 | 4.2 |
| 6 | 57 | 30 | 95 | 15/1 | 94 | 97 |
| 7 | 58 | 80 | 97 | 18/1 | 96 | 1.7 |
| 8 | 59 | 40 | 98 | 17/1 | 96 | 0.77 |
| 9 | 60 | 80 | 97 | 18/1 | 95 | 10 |
| 10 | 61 | 40 | 97 | 17/1 | 89 | 1.5 |
| 11 | 62 | 260 | 56 | 13/1 | 97 | ND |

[a]results obtained with commercially available scavenger: SiliaBond Thiol, using protocol recommended by SILICYCLE
[b]results obtained with commercially available scavenger: SiliaBond DMT, using protocol recommended by SILICYCLE
[c]conversion >99% (GC)

EXAMPLE 5

Alken-Alkyn Ring Closing Metathesis in Water

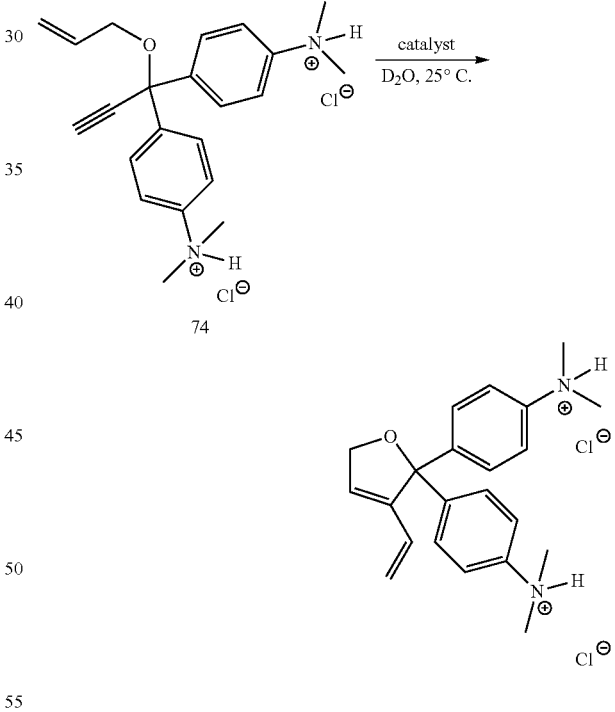

Appropriate amount of catalyst (2.5 or 5 mol %) was added on air to a solution of 74 (61 mg, 0.15 mmol) in $D_2O$ (1.5 ml). Reaction mixture was stirred at 25° C. 0.7 ml of reaction mixture was transferred to an NMR tube. Conversion and product purity was determined using NMR method.

Product: $^1H$ NMR (500 MHz, $D_2O$): δ=3.34 (s, 12H), 4.87 (br s, 2H), 5.26 (d, 1H, J=11 Hz), 5.3 (d, 1H, J=17.5 Hz), 6.34 (dd, 1H. J=18 Hz, J=11.5 Hz), 6.46 (br s, 1H), 7.59-7.61 (m, 4H) 7.65-7.78 (m, 4H); $^{13}C$ NMR (50 MHz, $D_2O$): δ=46.5, 74.0, 94.0, 118.9, 120.5, 126.9, 128.6, 130.1, 141.0, 141.9, 144.4.

| Entry | Catalyst (loading mol %) | Time [h] | Conversion [%] | Purity [%] |
|---|---|---|---|---|
| 1 | 49 (2.5) | 24 | 94 | 72 |
| 2 | 52 (5) | 24 | >98 | 80 |
| 3 | 53 (2.5) | 1.5 | 59 | 98 |
| 4 | 54 (5) | 24 | >98 | 92 |

EXAMPLE 6

Isomerization of Cis-1,4-Butenediol in Water

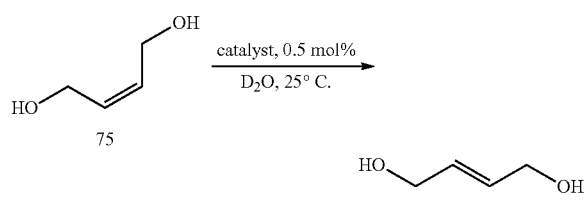

Appropriate amount of catalyst (0.5 mol %) was added on air, at 25° C. to a solution of 75 (12 mg, 0.14 mmol) in D2O (0.7 ml). Reaction mixture was transferred to an NMR tube and conversion and was determined using NMR method.

| Entry | Catalyst | Time [min] | Conversion [%] |
|---|---|---|---|
| 1 | 47 | 8 | 93 |
| 2 | 49 | 65 | 73 |
| 3 | 51 | 39 | 92 |
| 4 | 52 | 64 | 71 |
| 5 | 53 | 10 | 94 |
| 6 | 54 | 64 | 52 |
| 7 | 55 | 16 | 94 |
| 8 | 56 | 64 | 44 |

EXAMPLE 7

Self Metathesis of Allyl Alcohol in Water

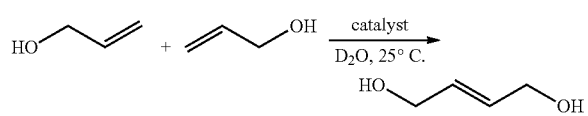

Appropriate amount of catalyst (2.5 or 5 mol %) was added on air to a solution of allyl alcohol (12 mg, 0.2 mmol) in D$_2$O (1 ml). Reaction mixture was stirred at 25° C. 0.7 ml of reaction mixture was transferred to an NMR tube and conversion was determined using NMR method.

| Entry | Catalyst (loading mol %) | Time [h] | Conversion [%] | E/Z |
|---|---|---|---|---|
| 1 | 49 (2.5) | 1.5 | 82 | 9.5/1 |
| 2 | 49 (2.5) | 24 | 78 | 11.9/1 |
| 3 | 49 (5) | 1.5 | 82 | 11.1/1 |
| 4 | 49 (5) | 24 | 89 | — |
| 5 | 51 (2.5) | 1.5 | 54 | 6.7/1 |
| 6 | 51 (2.5) | 24 | 53 | 6.9/1 |
| 7 | 51 (5) | 1.5 | 64 | 6.7/1 |
| 8 | 51 (5) | 24 | 70 | 8.0/1 |
| 9 | 52 (5) | 1.5 | 77 | — |
| 10 | 52 (5) | 24 | 89 | 11.2/1 |
| 11 | 53 (2.5) | 1.5 | 59 | 9.0/1 |
| 12 | 53 (2.5) | 24 | 64 | 8.3/1 |
| 13 | 53 (5) | 1.5 | 53 | 8.2/1 |
| 14 | 53 (5) | 24 | 62 | 8.2/1 |
| 15 | 54 (2.5) | 1.5 | 57 | 7.7/1 |
| 16 | 54 (2.5) | 24 | 60 | 9.4/1 |
| 17 | 54 (5) | 1.5 | 72 | 9.1/1 |
| 18 | 54 (5) | 24 | 86 | 7.4/1 |
| 19 | 55 (5) | 1.5 | 72 | 12.1/1 |
| 20 | 56 (2.5) | 1.5 | 68 | 8.2/1 |
| 21 | 56 (2.5) | 24 | 73 | 10.8/1 |

EXAMPLE 8

Ring Closing Metathesis in Water

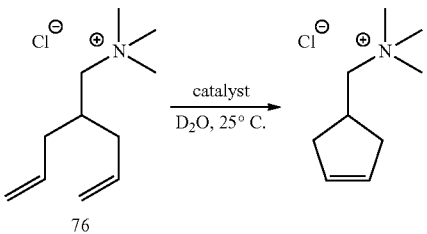

Appropriate amount of catalyst (2.5 or 5 mol %) was added on air to a solution of 76 (41 mg, 0.2 mmol) in D$_2$O (1 ml). Reaction mixture was stirred at 25° C. 0.7 ml of reaction mixture was transferred to an NMR tube and conversion was determined using NMR method.

| Entry | Catalyst (loading mol %) | Time [h] | Conversion [%] |
|---|---|---|---|
| 1 | 49 (2.5) | 2.5 | 97 |
| 2 | 49 (2.5) | 24 | >98 |
| 3 | 51 (2.5) | 2.5 | 95 |
| 4 | 51 (2.5) | 24 | >98 |
| 5 | 52 (2.5) | 2.5 | 96 |
| 6 | 52 (2.5) | 24 | >98 |
| 7 | 53 (2.5) | 2.5 | 88 |
| 8 | 53 (2.5) | 24 | 89 |
| 9 | 54 (2.5) | 2.5 | 86 |
| 10 | 55 (2.5) | 24 | 86 |
| 11 | 55 (5) | 2.5 | >98 |
| 12 | 56 (2.5) | 2.5 | >98 |

EXAMPLE 9

Ring Opening Metathesis Polimeryzation (ROMP)

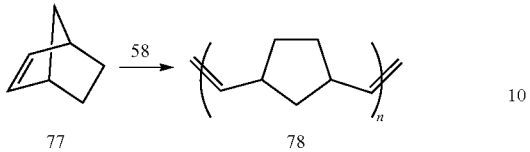

Appropriate amount of catalyst 58 (0.25 mol %) was added under argon to a solution of 77 (318 mg, 3.38 mmol) in dry, degased dichloromethane. Reaction mixture was stirred at room temperature for 10 minutes. Silica gel (318 mg) was added to the reaction mixture and resulted suspension was stirred for 10 minutes. Next, suspension was filtered through a funnel and colorless viscous filtrate was concentrated on rotavapor to dryness to afford 78 (295 mg, 93%) as a white solid. Ruthenium content in the product (8 ppm) was determined by ICP MS method.

As it is shown in examples 1-9, catalysts described herein are highly active and effective in various metathesis transformation, giving the product with low ruthenium contamination. Moreover catalysts described herein efficiently mediate metathesis reactions in water at relatively low loadings.

The invention claimed is:

1. A method of synthesizing a complex, comprising:
subjecting a precursor complex to reaction with an alkylating agent;
wherein the complex has a structure of formula 15

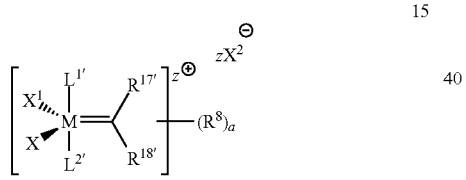

15 wherein $L^{1'}$ and $L^{2'}$ are, independently, inert ligands, wherein at least one of $L^{1'}$ and $L^{2'}$ comprises a quaternary ammonium group or a phosphonium group; and
M is ruthenium or osmium; and
X, $X^1$, and each $X^2$ are, independently, anionic ligands; and
$R^8$ is optionally substituted —$C_{1-20}$ alkyl, optionally substituted —$C_{3-8}$ cycloalkyl, optionally substituted —$C_{2-20}$ alkenyl, or optionally substituted —$C_{2-20}$ alkynyl, wherein each substituent is independently a halogen atom, —$C_{5-10}$ aryl, —C(=O)—$C_{1-6}$ alkyl, —C(=O)—O—$C_{1-6}$ alkyl, —C(=O)—N($C_{1-6}$ alkyl)$_2$, —C(=O)—NH—($C_{1-6}$ alkyl)-O—$C_{1-6}$ alkyl, —C(=O)—$C_{5-10}$ aryl, —C(=O)—O—$C_{5-10}$aryl, —C(=O)—N($C_{5-10}$ aryl)$_2$, or —C(=O)—NH—($C_{5-10}$ aryl)-O—$C_{5-10}$ aryl; and
$R^{17'}$ is H, optionally substituted —$C_{1-20}$ alkyl, optionally substituted —$C_{2-20}$ alkenyl, optionally substituted —$C_{2-20}$ alkynyl, or optionally substituted —$C_{5-10}$ aryl;
$R^{18'}$ is optionally substituted phenyl, optionally substituted vinyl, or optionally substituted —C=C(CH$_3$)$_2$;
$R^{17'}$ and $R^{18'}$ may be optionally linked together to form a cyclic or polycyclic system that is aliphatic or aromatic; or $R^{17'}$ and $R^{18'}$, together with the carbon atom connecting them, can optionally be a 3-phenyl-1H-indene-1-ylide substituent; or
$R^{17'}$, $R^{18'}$ or both $R^{17'}$ and $R^{18'}$ may be optionally linked to $L^1$ or $L^2$ to form a bidentate ligand;
a is 1, 2, 3, 4, 5, 6 or 7;
z is 1, 2, 3, 4, 5, 6 or 7; and
wherein the precursor complex has a structure of formula 10

10

Wherein M is ruthenium or osmium;
X and $X^1$ are each independently anionic ligands; and
$R^{17}$ is H, optionally substituted —$C_{1-20}$ alkyl, optionally substituted —$C_{2-20}$ alkenyl, optionally substituted —$C_{2-20}$ alkynyl, or optionally substituted —$C_{5-10}$ aryl; and
$R^{18}$ is optionally substituted phenyl, optionally substituted vinyl, or optionally substituted —C=C(CH$_3$)$_2$; or
$R^{17}$ and $R^{18}$ may be optionally linked together to form a cyclic or polycyclic system that is aliphatic or aromatic; or
$R^{17}$, $R^{18}$, or both $R^{17}$ and $R^{18}$ may be optionally linked to $L^1$ or $L^2$ to form a bidentate ligand; or
$R^{17}$ and $R^{18}$, together with the carbon atom connecting them, can optionally be a 3-phenyl-1H-indene-1-ylide substituent;
wherein the alkylating reagent has a formula $R^8X^2$, wherein $R^8$ is optionally substituted —$C_{1-20}$ alkyl, optionally substituted—$C_{3-8}$ cycloalkyl, optionally substituted —$C_{2-20}$ alkenyl, optionally substituted —$C_{2-20}$ alkynyl group; wherein each substituent is independently a halogen atom, —$C_{5-10}$ aryl, —C(=O)—$C_{1-6}$ alkyl, —C(=O)—O—$C_{1-6}$ alkyl, —C(=O)—N($C_{1-6}$ alkyl)$_2$, —C(=O)—NH—($C_{1-6}$ alkyl)-O—$C_{1-6}$ alkyl, —C(=O)—$C_{5-10}$ aryl, —C(=O)—O—$C_{5-10}$aryl, —C(=O)—N($C_{5-10}$ aryl)$_2$, or —C(=O)—NH—($C_{5-10}$ aryl)-O—$C_{5-10}$ aryl;
$X^2$ is an anionic ligand; and
wherein $L^1$ is a complex of general formula 9 is defined by formula

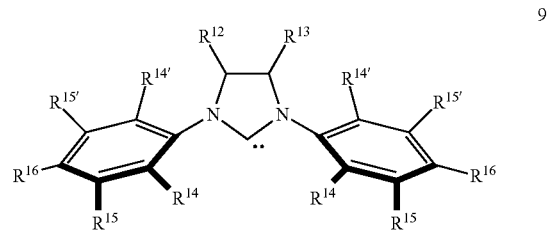

9 wherein $R^{12}$, $R^{13}$, each $R^{14}$, each $R^{14'}$, each $R^{15}$, each $R^{15'}$, and each $R^{16}$ are, independently, H, optionally substituted —$C_{1-6}$ alkyl, optionally substituted —$C_{1-6}$ haloalkyl, optionally substituted —$C_{5-10}$ aryl, optionally substituted —$C_{1-6}$ alkylamino, optionally substituted —$C_{1-6}$ alkylphosphine, or an optionally substituted —$C_{4-10}$ heterocyclic group, wherein each substituent is independently —$C_{1-6}$ alkyl, —$C_{1-6}$ alkylamino or a —$C_{4-10}$ heterocyclic group; and $R^{12}$ and $R^{13}$, $R^{14}$ and $R^{15}$, and $R^{14'}$ and $R^{13'}$ may be optionally linked together to form a substituted or unsubstituted, fused —$C_{4-8}$ carbocyclic ring, or a substituted or unsubstituted, fused aromatic ring; and $L^2$ is an inert ligand, wherein group 9 or $L^2$ contains at least one $X^2$ group, alkylamino group, or alkylphosphine group.

2. A method of synthesizing a complex of formula 17,

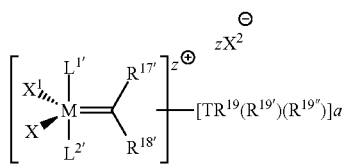

17 wherein $L^{1'}$ are $L^{2'}$ are, independently, an inert ligand, wherein at least one of $L^{1'}$ and $L^{2'}$ comprises a quaternary ammonium or a phosphonium group; and M is ruthenium or osmium;

X, $X^1$, and each $X^2$ are, independently, an anionic ligand;

$R^{17'}$ is H, optionally substituted —$C_{1-20}$ alkyl, optionally substituted —$C_{2-20}$ alkenyl, optionally substituted —$C_{2-20}$ alkynyl, or optionally substituted —$C_{5-10}$ aryl;

$R^{18'}$ is optionally substituted phenyl, optionally substituted vinyl, or optionally substituted —C=C(CH$_3$)$_2$; or $R^{17'}$ and $R^{18'}$ may be optionally linked together to form a cyclic or polycyclic system that is aliphatic or aromatic;

$R^{17'}$ and $R^{18'}$, together with a carbon atom connecting them, can optionally be a 3-phenyl-1H-indene-1-ylide substituent; or $R^{17'}$, $R^{18'}$, or both $R^{17'}$ and $R^{18'}$ may be optionally linked to $L^1$ or $L^2$ to form a bidentate ligand;

a is 1, 2, 3, 4, 5, 6 or 7;

z is 1, 2, 3, 4, 5, 6 or 7;

T is N or P;

$R^9$, $R^{19'}$, $R^{19''}$ are, independently, H, —$C_{1-6}$ alkyl, —$C_{5-10}$ aryl, or a $C_{4-10}$ heterocyclic group; and $X^2$ comes from complex 10;

wherein the method comprises subjecting a compound having a formula $TR^{19}(R^{19'})(R^{19''})$ to reaction with the precursor complex that has a structure of complex 10;

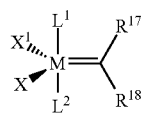

10 wherein M is ruthenium or osmium;

X and $X^1$ are each independently anionic ligands;

$L^1$ and $L^2$ are independently inert ligands, wherein at least one of $L^1$ and $L^2$ comprises an $X^2$ group, an alkylamino group, or an alkylphosphine group;

$R^{17}$ is H, optionally substituted —$C_{1-20}$ alkyl, optionally substituted —$C_{2-20}$ alkenyl, optionally substituted —$C_{2-20}$ alkynyl, or optionally substituted —$C_{5-10}$ aryl; and $R^{18}$ is optionally substituted phenyl, optionally substituted vinyl, or optionally substituted —C=C(CH$_3$)$_2$; or $R^{17}$ and $R^{18}$ may be optionally linked together to form a cyclic or polycyclic system that is aliphatic or aromatic; or $R^{17}$, $R^{18}$, or both $R^{17}$ and $R^{18}$ may be optionally linked to $L^1$ or $L^2$ to form a bidentate ligand; or $R^{17}$ and $R^{18}$, together with the carbon atom connecting them, can optionally be a 3-phenyl-1H-indene-1-ylide substituent; and wherein $L^1$ is a complex of general formula 9 is defined by formula

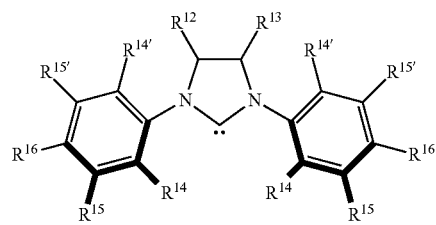

9 wherein $R^{12}$, $R^{13}$, each $R^{14}$, each $R^{14'}$, each $R^{15}$, each $R^{15'}$, and each $R^{16}$ are, independently, H, optionally substituted —$C_{1-6}$ alkyl, optionally substituted —$C_{1-6}$ haloalkyl, optionally substituted —$C_{5-10}$ aryl, optionally substituted —$C_{1-6}$ alkylamino, optionally substituted —$C_{1-6}$ alkylphosphine, or an optionally substituted —$C_{4-10}$ heterocyclic group, wherein each substituent is independently —$C_{1-6}$ alkyl, —$C_{1-6}$ alkylamino or a —$C_{4-10}$ heterocyclic group; and $R^{12}$ and $R^{13}$, $R^{14}$ and $R^{15}$, and $R^{14'}$ and $R^{13'}$ may be optionally linked together to form a substituted or unsubstituted, fused —$C_{4-8}$ carbocyclic ring, or a substituted or unsubstituted, fused aromatic ring; and $L^2$ is an inert ligand, wherein group 9 or $L^2$ contains at least one $X^2$ group, alkylamino group, or alkylphosphine group.

3. The method according to claim 1, wherein a complex of general formula 10 is defined by general formula 14

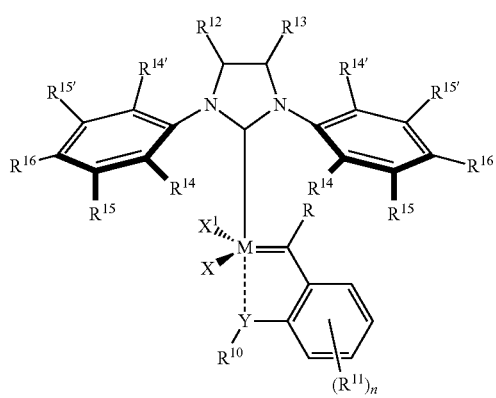

14 wherein M is ruthenium or osmium;

X and $X^1$ are, independently, inert ligands;

Y is O, S, N or P;

R is H, —$C_{1-20}$ alkyl, —$C_{2-20}$ alkenyl, —$C_{2-20}$ alkynyl, or —$C_{3-10}$ aryl;

$R^{10}$ is optionally substituted —$C_{1-20}$ alkyl, optionally substituted —$C_{5-10}$ aryl, optionally substituted —$C_{1-20}$ alkoxy, optionally substituted —$C_{5-10}$ aryloxy, optionally substituted —$C_{1-20}$ alkylamino, optionally substituted —$C_{1-20}$ protonated alkylamino, optionally substituted —$C_{1-20}$ alkylammonium, optionally substituted —$C_{1-12}$ alkylthiol, optionally substituted —CH$_2$C(=O)—$C_{1-6}$ alkyl, optionally substituted —CH$_2$C(=O)—O—$C_{1-6}$ alkyl, optionally substituted —CH$_2$C(=O)—N($C_{1-6}$ alkyl)$_2$, optionally substituted —CH$_2$C(=O)—NH—($C_{1-6}$ alkyl)-O—$C_{1-6}$ alkyl, optionally substituted —CH$_2$C(=O)—C$_{5-10}$ aryl, optionally substituted —CH$_2$C(=O)—O—C$_{5-10}$ aryl, optionally substituted —CH$_2$C(=O)—N(C$_{5-10}$ aryl)$_2$, optionally substituted —CH$_2$C(=O)—NH—(C$_{5-10}$ aryl)-O—C$_{5-10}$ aryl, optionally substituted —C$_{1-20}$ alkylphosphine, optionally substituted —C$_{1-20}$ alkylphosphonium, optionally substituted —C$_{4-10}$ heterocyclic, or an optionally substituted —C$_{4-10}$ quaternized heterocyclic group, wherein each substituent is independently —C$_{1-20}$ alkyl, —C$_{5-10}$ aryl or a —C$_{4-10}$ heterocyclic group;

R$^{11}$ is halogen, optionally substituted —C$_{1-20}$ alkyl, optionally substituted —C$_{1-20}$ haloalkyl, optionally substituted —C$_{2-20}$ alkenyl, optionally substituted —C$_{2-20}$ alkynyl, optionally substituted —C$_{5-10}$ aryl, optionally substituted —C$_{1-20}$ alkoxy, optionally substituted —C$_{2-20}$ alkenyloxy, optionally substituted —C$_{2-20}$ alkynyloxy, optionally substituted —C$_{5-10}$ aryloxy, optionally substituted —C$_{1-20}$ alkoxy carbonyl, optionally substituted —C$_{1-20}$-alkylamino, optionally substituted —C$_{1-20}$ protonated alkylamino, optionally substituted —C$_{1-20}$ alkylammonium, optionally substituted amino, optionally substituted protonated amino, optionally substituted —C$_{4-10}$ heterocyclic, optionally substituted —C$_{4-10}$ quaternized heterocyclic, optionally substituted —C$_{1-20}$ alkylphosphino, optionally substituted —C$_{1-20}$ alkylphosphonium, optionally substituted —C$_{1-20}$ alkylthiol, nitro, carboxyl, optionally substituted amido, optionally substituted sulfonamido, or optionally substituted —C$_{1-20}$ perhaloalkyl, wherein each substituent is independently —C$_{1-20}$ alkyl, —C$_{1-20}$ haloalkyl, —C$_{1-20}$ perhaloalkyl, —C$_{5-10}$ aryl, or a —C$_{4-10}$ heterocyclic group;

n is 0, 1, 2, 3, or 4;

R$^{12}$, R$^{13}$, R$^{14}$, R$^{14'}$, R$^{15}$, R$^{15'}$, R$^{16}$ are independently, H, optionally substituted —C$_{1-6}$ alkyl, optionally substituted —C$_{1-6}$ haloalkyl, optionally substituted —C$_{5-10}$ aryl, optionally substituted —C$_{1-6}$ alkylamino, optionally substituted —C$_{1-6}$ alkylphosphino, -optionally substituted C$_{4-10}$ heterocyclic group, wherein each substituent is independently —C$_{1-6}$ alkyl, —C$_{1-6}$ alkylamino or a —C$_{4-10}$ heterocyclic group;

R$^{12}$ and R$^{13}$, R$^{14}$ and R$^{15}$, and R$^{14'}$ and R$^{15'}$ may be optionally linked together to form a substituted or unsubstituted, fused —C$_{4-8}$ carbocyclic ring, or a substituted or unsubstituted, fused aromatic ring;

and a complex of general formula 15 is defined by general formula 1

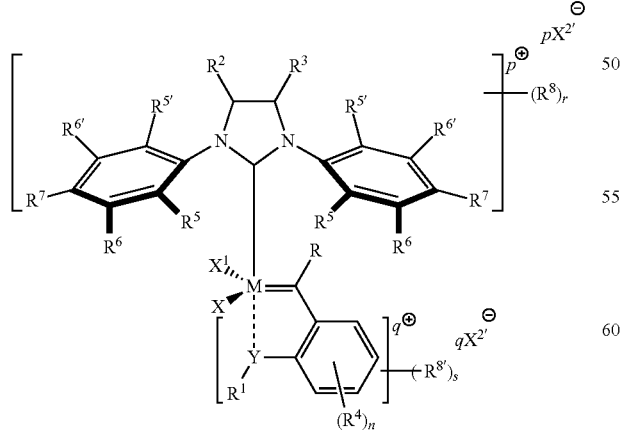

wherein M is ruthenium or osmium;
X, X$^1$, X$^2$ and X$^{2'}$ are, independently, inert ligands;
Y is O, S, N, or P;

R is H, —C$_{1-20}$ alkyl, —C$_{2-20}$ alkenyl, —C$_{2-20}$ alkynyl, or —C$_{5-10}$ aryl;

R$^1$ is optionally substituted —C$_{1-20}$ alkyl, optionally substituted C$_{3-8}$ cycloalkyl, optionally substituted —C$_{2-20}$ alkenyl, optionally substituted —C$_{2-20}$ alkynyl, optionally substituted —C$_{5-10}$ aryl, optionally substituted —C$_{1-20}$ alkoxy, optionally substituted —C$_{2-20}$ alkenyloxy, optionally substituted —C$_{2-20}$ alkynyloxy, optionally substituted —C$_{5-10}$ aryloxy, optionally substituted —C$_{1-20}$ alkoxycarbonyl, optionally substituted —C$_{1-20}$ alkylamino, optionally substituted —C$_{1-20}$ alkylphosphino, -optionally substituted C$_{1-20}$ alkylthiol, optionally substituted —C$_{1-20}$ alkylammonium, optionally substituted —C$_{1-20}$ alkylphosphonium, optionally substituted —C$_{1-20}$ alkylsulfonyl, optionally substituted —C$_{1-20}$ alkylosulfinyl, optionally substituted —CH$_2$C(=O)—C$_{1-6}$ alkyl, optionally substituted —CH$_2$C(=O)—O—C$_{1-6}$ alkyl, optionally substituted —CH$_2$C(=O)—N(C$_{1-6}$ alkyl)$_2$, optionally substituted —CH$_2$C(=O)—NH—(C$_{1-6}$ alkyl)-O—C$_{1-6}$ alkyl, optionally substituted —CH$_2$C(=O)—C$_{5-10}$ aryl, optionally substituted —CH$_2$C(=O)—O—C$_{5-10}$ aryl, optionally substituted —CH$_2$C(=O)—N(C$_{5-10}$ aryl)$_2$, optionally substituted —CH$_2$C(=O)—NH—(C$_{5-10}$ aryl)-O—C$_{5-10}$ aryl, optionally substituted —C$_{4-10}$heterocyclic, or optionally substituted —C$_{4-10}$ quaternized heterocyclic, wherein each substituent is independently —C$_{1-20}$ alkyl, —C$_{5-10}$ aryl, or a —C$_{4-10}$ heterocyclic group;

R$^1$ may be optionally linked to X or X$^1$ to form a tridentate ligand;

R$^2$ and R$^3$ are, independently, H, optionally substituted —C$_{1-6}$ alkyl, optionally substituted —C$_{3-8}$ cycloalkyl, optionally substituted —C$_{5-10}$ aryl, optionally substituted —C$_{1-20}$ alkylamino, optionally substituted —C$_{1-20}$ alkylphosphino, optionally substituted —C$_{1-20}$ alkylammonium, or optionally substituted —C$_{1-20}$ alkylphosphonium, wherein each substituent is independently: —C$_{5-10}$ aryl, —C$_{4-10}$ heterocyclic, or a —C$_{4-10}$ quaternized heterocyclic group, which in turn may be substituted with at least one: nitro, —C$_{1-6}$ alkyl, —C$_{1-6}$ alkoxy, —C$_{5-10}$ aryl group or halogen;

R$^2$ and R$^3$ may be optionally linked together to form a substituted or unsubstituted, fused —C$_{4-8}$ carbocyclic ring, or a substituted or unsubstituted, fused aromatic ring;

R$^4$ is halogen, optionally substituted —C$_{1-20}$ alkyl, optionally substituted —C$_{2-20}$ alkenyl, optionally substituted —C$_{2-20}$ alkynyl, optionally substituted —C$_{5-10}$ aryl, optionally substituted —C$_{1-20}$ alkoxy, optionally substituted —C$_{2-20}$ alkenyloxy, optionally substituted —C$_{2-20}$ alkynyloxy, optionally substituted —C$_{5-10}$ aryloxy, optionally substituted —C$_{1-20}$ alkoxy carbonyl, optionally substituted —C$_{1-20}$ alkylamino, optionally substituted —C$_{1-20}$ protonated alkylamino, optionally substituted amino, optionally substituted protonated amino, optionally substituted —C$_{1-20}$ alkylphosphino, optionally substituted —C$_{1-20}$ alkylthiol, optionally substituted —C$_{1-20}$ alkylammonium, optionally substituted —C$_{1-20}$ alkylphosphonium, optionally substituted —C$_{4-10}$ quaternized heterocyclic, nitro, carboxyl, optionally substituted amido, optionally substituted sulfonamido, or optionally substituted —C$_{1-20}$ perhaloalkyl; wherein each substituent is independently —C$_{1-20}$ alkyl, —C$_{1-20}$ perhaloalkyl, —C$_{5-10}$ aryl, or a —C$_{4-10}$ quaternized heterocyclic group;

n is 0, 1, 2, 3, or 4;

R$^5$, R$^{5'}$, R$^6$, R$^{6'}$, and R$^7$ are, independently, H, optionally substituted —C$_{1-6}$ alkyl, optionally substituted —C$_{1-20}$ alkylamino, optionally substituted —C$_{1-20}$ alkylphosphino, optionally substituted —$C_{1-20}$ alkylammonium, optionally substituted —$C_{1-20}$ alkylphosphonium, optionally substituted —$C_{4-10}$ heterocyclic, optionally substituted —$C_{4-10}$ quaternized heterocyclic group, wherein each substituent is independently a —$C_{4-10}$ quaternized heterocyclic, —$C_{1-6}$ alkyl, or —$C_{5-10}$ aryl, which in turn may be substituted with nitro, —$C_{1-6}$ alkyl, —$C_{1-6}$ alkoxy, —$C_{5-10}$ aryl group or halogen;

$R^5$ and $R^6$, and $R^{5'}$ and $R^{6'}$ may be optionally linked together to form a substituted or unsubstituted, fused —$C_{4-8}$ carbocyclic ring, or a substituted or unsubstituted, fused aromatic ring;

$R^8$ is optionally substituted —$C_{1-20}$ alkyl, optionally substituted —$C_{3-8}$ cycloalkyl, optionally substituted —$C_{2-20}$ alkenyl, or optionally substituted —$C_{2-20}$ alkynyl; wherein each substituent is independently a halogen atom, —$C_{5-10}$ aryl, —C(=O)—$C_{1-6}$ alkyl, —C(=O)—O—$C_{1-6}$ alkyl, —C(=O)—N($C_{1-6}$ alkyl)$_2$, —C(=O)—NH—($C_{1-6}$ alkyl)-O—$C_{1-6}$ alkyl, —C(=O)—$C_{5-10}$ aryl, —C(=O)—O—$C_{5-10}$aryl, —C(=O)—N($C_{5-10}$ aryl)$_2$, or —C(=O)—NH—($C_{5-10}$ aryl)-O—$C_{5-10}$ aryl;

p is 1, 2, 3, 4, or 5;
r is 1, 2, or 3;
$R^{8'}$ is H, —$C_{1-20}$ alkyl, $C_{3-8}$ cycloalkyl, —$C_{2-20}$ alkenyl, or —$C_{2-20}$ alkynyl;
q is 0, 1, 2 or 3;
s is 0, 1, 2, or 3;
wherein at least one substituent among $R^2$, $R^3$, $R^5$, $R^{5'}$, $R^6$, $R^{6'}$, and $R^7$ contains a quaternary onium group;
and the complex obtained in this manner may be optionally subjected to a further reaction with a compound of formula $R^{8'}X^{2'}$, giving a different complex of formula 1, wherein $R^{8'}$ and $X^{2'}$ are as defined above.

4. The method according to claim 3, wherein, in formula 14 M is a ruthenium;
X and $X^1$ are an inert ligand;
Y is O;
$R^{10}$ is optionally substituted —$C_{1-12}$ alkyl, optionally substituted —$C_{1-12}$ haloalkyl, optionally substituted —$C_{5-10}$ aryl, optionally substituted —$C_{1-12}$ alkoxy, optionally substituted —$C_{5-10}$ aryloxy, optionally substituted —$C_{1-12}$ alkoxy carbonyl, optionally substituted —$C_{1-12}$ alkylamino, an optionally substituted —$C_{4-10}$ heterocyclic group, wherein each substituent is independently —$C_{1-12}$ alkyl, —$C_{5-10}$ aryl or a —$C_{4-10}$ heterocyclic group;
$R^{11}$ is halogen, optionally substituted —$C_{1-12}$ alkyl, optionally substituted —$C_{1-12}$ haloalkyl, optionally substituted aryl, optionally substituted —$C_{1-12}$ alkoxy, optionally substituted —$C_{5-10}$ aryloxy, optionally substituted —$C_{1-12}$ alkoxy carbonyl, optionally substituted —$C_{1-12}$ alkylamino, amino, optionally substituted —$C_{1-12}$ alkylphosphino, optionally substituted —$C_{4-10}$ heterocyclic, nitro, carboxyl, optionally substituted amido, optionally substituted sulfonamido group; wherein each substituent is independently —$C_{1-12}$ alkyl, —$C_{1-12}$ haloalkyl, —$C_{1-12}$ perhaloalkyl, —$C_{5-10}$ aryl, or a —$C_{4-10}$ heterocyclic group;
n is 0, 1 or 2; and
$R^{12}$, $R^{13}$, $R^{14}$, $R^{14'}$, $R^{15}$, $R^{15'}$, $R^{16}$ are, independently, H, optionally substituted —$C_{1-6}$ alkyl, optionally substituted —$C_{1-6}$ haloalkyl, optionally substituted —$C_{5-10}$ aryl, optionally substituted —$C_{1-6}$ alkylamino, optionally substituted —$C_{1-6}$ alkylphosphino, optionally substituted —$C_{4-10}$ heterocyclic group, each optionally substituted with —$C_{1-6}$ alkyl or —$C_{4-10}$ heterocyclic group; and
$R^{12}$ and $R^{13}$, $R^{14}$ and $R^{13}$, and $R^{14'}$ and $R^{15'}$ may be optionally linked together to form a substituted or unsubstituted, fused —$C_{4-8}$ carbocyclic ring, or a substituted or unsubstituted, fused aromatic ring.

5. The method according to claim 4, wherein in formula 14 M is ruthenium;
X and $X^1$ are independently Cl, Br or I;
R is H;
$R^{10}$ is an iso-propyl group or a 1-methyl-4-piperidinyl group; $R^{11}$ is a nitro or a —$NMe_2$ group; and
n is 0 or 1.

6. The method according to claim 5, wherein a compound of formula 14 is obtained by reacting a compound of formula 11

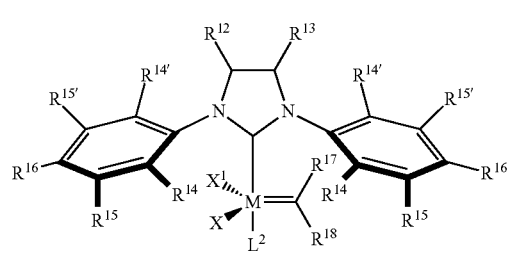

11 wherein all X, $X^1$, $L^2$, $R^{12}$, $R^{13}$, each $R^{14}$, each $R^{14'}$, each $R^{15}$, each $R^{15'}$, each $R^{16}$, $R^{17}$, and $R^{18}$ are as defined above, with an intermediate of formula 2a or 2b,

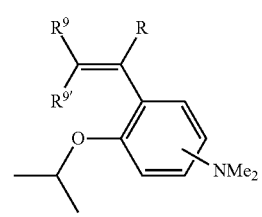

2a

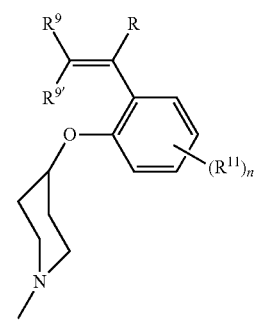

2b wherein R is H;
$R^9$ and $R^{9'}$ are a methyl or ethyl group;
$R^{11}$ is an electron acceptor group; and
n is 0 or 1.

7. The method according to claim 1, wherein, in formula 9, substituents $R^{12}$, $R^{13}$ are, independently, H, —$CH_2NMe_2$ group or

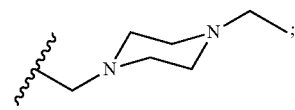 [SMILES: *CN1CCN(CC)CC1]

$R^{14}$ and $R^{14'}$ are a methyl or iso-propyl group;
$R^{15}$ and $R^{15'}$ are H; and $R^{16}$ is H, a methyl group or

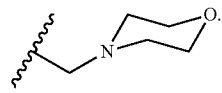 [SMILES: *CN1CCOCC1]

8. The method according to claim 1, wherein the reaction is carried out in $R^8X^2$ as a solvent, wherein $R^8X^2$ is $CH_3Cl$, $CH_3I$, $CH_3Br$, $(CH_3)_2SO_4$ or in an organic solvent comprising methanol, ethanol, ethyl acetate, iso-propanol, tert-butanol, sec-butanol, diethyl ether, n-propyl ether, diisopropyl ether, tert-butyl-methyl ether, cyclopentyl-methyl ether, 1,2-dioxane, 1,3dioxane, 1,4-dioxane, dimethylformamide, tetrahydrofurane, dichloromethane, dichloroethane, trichloromethane, tetrachloromethane, tetrachloroethane, pentane, hexane, heptane, benzene, toluene, xylene, or any mixture thereof.

* * * * *